US012758623B2

(12) United States Patent
Snook et al.

(10) Patent No.: US 12,758,623 B2
(45) Date of Patent: Oct. 13, 2026

(54) ANTI-GUCY2C VACCINE COMPOSITIONS AND METHODS OF USING THEM

(71) Applicant: THOMAS JEFFERSON UNIVERSITY, Philadelphia, PA (US)

(72) Inventors: Adam E Snook, Aston, PA (US); Scott A. Waldman, Philadelphia, PA (US); Trevor R Baybutt, Dresher, PA (US); John C Flickinger, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 279 days.

(21) Appl. No.: 17/775,561

(22) PCT Filed: Nov. 9, 2020

(86) PCT No.: PCT/US2020/059752
§ 371 (c)(1),
(2) Date: May 9, 2022

(87) PCT Pub. No.: WO2022/098372
PCT Pub. Date: May 12, 2022

(65) Prior Publication Data

US 2025/0312429 A1 Oct. 9, 2025

Related U.S. Application Data

(60) Provisional application No. 62/933,361, filed on Nov. 8, 2019, provisional application No. 62/932,499, filed on Nov. 7, 2019.

(51) Int. Cl.

| | |
|---|---|
| ***A61P 35/00*** | (2006.01) |
| ***A61K 9/00*** | (2006.01) |
| ***A61K 35/74*** | (2015.01) |
| ***A61K 39/00*** | (2006.01) |
| ***C12N 1/20*** | (2026.01) |
| ***C12N 15/74*** | (2006.01) |
| ***C12N 15/86*** | (2006.01) |
| ***C12R 1/01*** | (2006.01) |

(52) U.S. Cl.
CPC .... *A61K 39/001154* (2018.08); *A61K 9/0019* (2013.01); *A61K 35/74* (2013.01); *A61P 35/00* (2018.01); *C12N 1/20* (2013.01); *C12N 15/74* (2013.01); *C12N 15/86* (2013.01); *A61K 2039/523* (2013.01); *A61K 2039/5252* (2013.01); *A61K 2039/5256* (2013.01); *C12N 2710/10021* (2013.01); *C12N 2710/10022* (2013.01); *C12N 2710/10034* (2013.01); *C12R 2001/01* (2021.05); *C12Y 406/01002* (2013.01)

(58) Field of Classification Search
CPC ............ A61K 39/001154; A61K 35/74; A61K 2039/52; A61P 35/00; C12R 2001/01
See application file for complete search history.

(56) References Cited

PUBLICATIONS

NCT01972737—Thomas Jefferson University—Phase I Study of AdS-hGCC (Human Guanylyl Cyclase C)-PADRE in Stage I/II Colon Cancer, Oct. 30, 2013. (Year: 2013).*

Yang et al. A novel fiber chimeric conditionally replicative adenovirus-Ad5/F35 for tumor therapy. Cancer biology & therapy, 18, 833-840, 2017. (Year: 2017).*

Snook A. Metastatic colorectal cancer immunotherapy with GUCY2C-expressing Listeria monocytogenes. Project report [online]. Sep. 2018 [retrieved Jan. 12, 2026] Retrieved from the Internet: [URL: https://apps.dtic.mil/sti/citations/AD1062516]. (Year: 2018).*

* cited by examiner

*Primary Examiner* — Elly-Gerald Stoica

(57) ABSTRACT

Compositions comprising a modified adenovirus AD5.F35 which includes coding sequence of soluble GUCY2C extracellular domain sequences are disclosed. Compositions comprising a *Listeria monocytogenes* vector which includes coding sequence of soluble GUCY2C extracellular domain sequences are disclosed. Methods of treating individuals diagnosed with cancer/tumors expressing GUCY2C methods of preventing micro-metastasis are disclosed.

16 Claims, 26 Drawing Sheets

Specification includes a Sequence Listing.

FIGURE 2
REPEAT REGION 1
Pcmv ie
Kozak
BGUCY2C 1-429
PADRE
BGH polyA
pIX
E2B IVa2
E2B 140K DNA polymerase
E2B pTP 75K
L1 52, 55K
L1 pIIIa
L2 pVII
L2 pV
L3 pVI
L3 p
L3 23K viral endoprotease
E2A DNA binding protein
hexon assembly
hexon-associated precursor
E3 12.5K
E3 14.7K
Ad35 fibre
E4 orf 6/7
E4 orf 6
E4 orf 3/4

C

D

ANTI-GUCY2C VACCINE COMPOSITIONS AND METHODS OF USING THEM

STATEMENT OF GOVERNMENT RIGHTS

This invention was made with government support under W81XWH-17-1-0299 awarded by US Department of Defense. The government has certain rights in the invention.

This invention was made with government support under R01 CA170533 awarded by the National Institutes of Health. The government has certain rights in the invention.

INCORPORATION BY REFERENCE OF SEQUENCE LISTING

The sequence listing submitted Jun. 11, 2025, identified as 17775561_Repl_SEQ_LIST_20250611_ST25, created on Jun. 11, 2025, and having a file size of 96,000 bytes, is incorporated by reference herein.

BACKGROUND OF THE INVENTION

Despite improvements and successes in therapy, cancer continues to claim the lives of numerous people world-wide. Improvements in screening provide the opportunity to identify many individuals who have early stage cancer as well as many who do not have cancer but who are genetically predisposed to developing cancer and thus at an elevated risk of developing cancer. Moreover, because of improvements in treatment, there are numerous people who have either had cancer removed or in remission. Such people are at a risk of relapse or recurrence and so are also at an elevated risk of developing cancer.

There is a need for improved methods of treating individuals suffering GUCY2C expressing tumors/cancers. There is a need for compositions useful to treat individuals suffering from GUCY2C expressing cancers. There is a need for improved methods of preventing a recurrence of GUCY2C expressing cancers in individuals who have been treated for such cancers. There is a need for compositions useful to prevent a recurrence of GUCY2C expressing cancers in individuals who have been treated for such cancers. There is a need for improved methods of preventing GUCY2C expressing cancers in individuals, particularly those who have been identified as having a genetic predisposition for such cancers. There is a need for compositions useful for preventing GUCY2C expressing cancers in individuals. There is a need for improved methods of identifying compositions useful to treat and prevent GUCY2C expressing cancers in individuals.

BRIEF DESCRIPTION OF THE SEQUENCE LISTING

Figure 1:
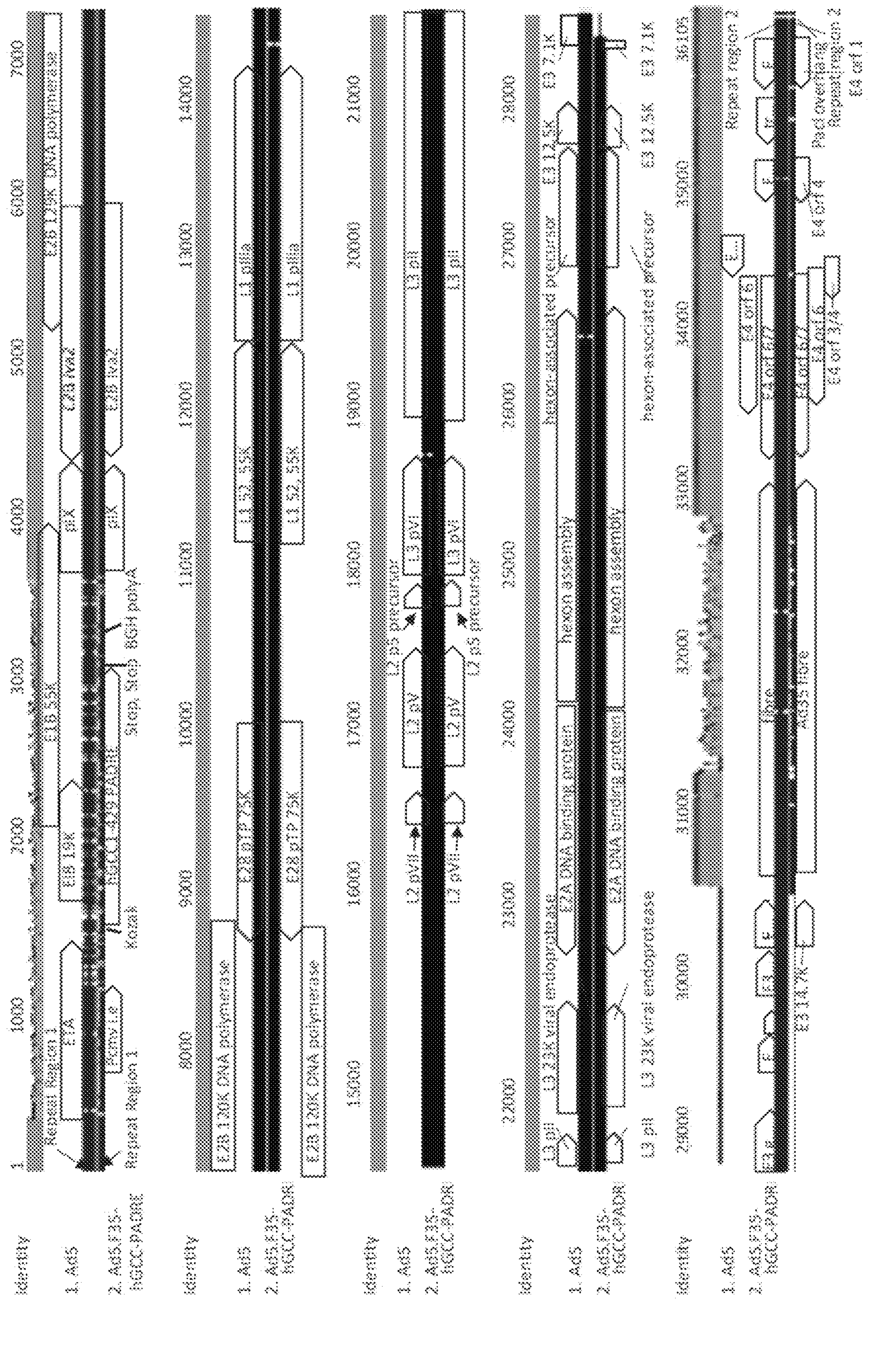
FIG. 1 shows the alignment of Ad5.F35-hGCC-PADRE and Wild Type Ad5. The genome of Ad5.F35-hGCC-PADRE differs from that of Ad5 by 1) replacement of the E1 region (E1A and E1B) with the hGCC-PADRE expression cassette, 2) deletion of most of the E3 region and 3) replacement of the Ad5 fiber with the Ad35 fiber.
Figure 2:
FIG. 2 shows Ad5F35-hGUCY2C-PADRE map.

SEQ ID NO: 1: DNA sequence of Human GUCY2C (Genbank accession number BC136544), incorporated herein by reference.

SEQ ID NO:2: Predicted Amino Acid Sequence of Human GUCY2C.

SEQUENCE ID NO:3: Codon optimized DNA sequence of Human GUCY2C.

SEQUENCE ID NO:4: Predicted Amino Acid Sequence of Human GUCY2C.

SEQ ID NO:5: Codon optimized DNA sequence of soluble human GUCY2C.

SEQ ID NO 6: Soluble human GUCY2C predicted amino acid sequence.

SEQ ID NO: 7: DNA sequence encoding a PADRE.

SEQ ID NO: 8: Predicted amino acid sequence of the PADRE of SEQ NO: 6.

SEQ ID NO:9: Codon optimized DNA sequence of a soluble human GUCY2C fused in frame with DNA sequence encoding a PADRE (C terminal fusion).

SEQ ID NO:10: Predicted amino acid sequence of codon optimized DNA sequence of a soluble human GUCY2C fused in frame with DNA sequence encoding a PADRE (N terminal fusion).

SEQ ID NO. 11: Ad5.F35-hGUCY2C-PADRE vector sequence.

SEQ ID NO:12: T cell epitope present in the 33 kDa C-terminal region of *P. vivax* MSP1.

SEQ ID NO:13: T cell epitope present in circumsporozoite protein of *Plasmodium falciparum.*

SEQ ID NO:14: T cell epitope present in circumsporozoite protein of *Plasmodium falciparum.*

SEQ ID NO:15: T cell epitope present in circumsporozoite protein of *Plasmodium falciparum.*

SEQ ID NO:16: T cell epitope present in circumsporozoite protein of *Plasmodium falciparum.*

SEQ ID NO:17: T cell epitope present in circumsporozoite protein of *Plasmodium falciparum.*

SEQ ID NO:18: T cell epitope present in circumsporozoite protein of *Plasmodium falciparum.*

SEQ ID NO:19: T cell epitope tetanus toxoid $TT_{830-844}$.

SEQ ID NO:20: T cell epitope tetanus toxoid $TT_{947-967}$.

SEQ ID NO:21: T cell epitope tetanus toxoid $TT_{590-603}$.

SEQ ID NO:22: T cell epitope tetanus toxoid $TT_{615-629}$.

SEQ ID NO:23: T cell epitope tetanus toxoid $TT_{639-652}$.

SEQ ID NO:24: T cell epitope tetanus toxoid $TT_{830-843}$.

SEQ ID NO:25: T cell epitope tetanus toxoid $TT_{947-967}$.

SEQ ID NO:26: T cell epitope influenza hemagglutinin residues 306-318.

SEQ ID NO:27: T cell epitope enterovirus 71 VP1 capsid protein residues 66-77.

SEQ ID NO:28: T cell epitope enterovirus 71 VP1 capsid protein residues 145-159.

SEQ ID NO:29: T cell epitope enterovirus 71 VP1 capsid protein residues 247-261 SEQ ID NO:30: T cell epitope EBV $LMP_{1159-175}$.

SEQ ID NO:31: T cell epitope HIV $Gag_{131-15}$.

SEQ ID NO:32: T cell epitope HIV $Gag_{211-230}$.

SEQ ID NO:33: T cell epitope HIV $Gag_{241-260}$.

SEQ ID NO:34: T cell epitope HIV $Gag_{263-277}$.

SEQ ID NO:35: T cell epitope HIV $Gag_{271-290}$.

SEQ ID NO:36: T cell epitope HIV $Gag_{291-310}$.

SEQ ID NO:37: T cell epitope HIV $Gag_{301-320}$.

SEQ ID NO:38: T cell epitope HIV $Gag_{321-340}$.

SEQ ID NO:39: T cell epitope HIV $Gag_{331-350}$.

SEQ ID NO:40: T cell epitope Ad5 hexon protein residues 556 to 580.

SEQ ID NO:41: T cell epitope Ad5 hexon protein residues 56-80.

SEQ ID NO:42: T cell epitope Ad5 hexon protein residues 316-335.

SEQ ID NO:43: T cell epitope Ad5 hexon protein residues 906-930.

DETAILED DESCRIPTION OF THE INVENTION

1.0 Definitions

As used herein, "GUCYC2", "GCC", "human GUCYC2", "human GCC", "GUCYC2 protein", "GCC protein", "human GUCYC2 protein" and "human GCC protein" are used interchangeably herein to refer to human guanylyl cyclase C protein. A nucleic acid sequence that encodes human GUCYC2 is set forth in SEQ ID NO:1 (Genbank accession number BC136544). The human GUCYC2 protein encoded by the longest open reading frame of SEQ ID NO:1 has the amino acid sequence set forth at SEQ ID NO:2 (Genbank accession number AAB19934). A codon optimized sequence that encodes human GUCYC2 has been described by Magee et. al. (Magee M S et al. (2018) Cancer Immunol Res 6:509-516, which is incorporated herein by reference) and is set forth at SEQ ID NO: 3.

The GUCYC2 protein is a cell-surface or membrane-bound receptor protein. The GUCYC2 protein has some generally accepted domains, each of which contributes a separable function to the GUCYC2 molecule. These domains include a signal sequence (also referred to interchangeably as a signal peptide), an extracellular domain, a transmembrane domain, a kinase homology domain and a guanylyl cyclase catalytic domain (the kinase homology domain and the guanylyl cyclase catalytic domain together are sometimes referred to interchangeably as an intracellular or cytoplasmic domain). The domains are described herein from the N-terminus to the C-terminus as they occur when the protein is produced in the cell.

The GUCYC2 signal sequence is present the newly synthesized GUCYC2 protein at the N-terminus. The GUCYC2 signal sequence functions in the translocation of the protein from location where it is initially produced in the cell. The GUCYC2 signal peptide is typically excised for maturation to yield functional mature protein as part of or following protein transport.

The GUCYC2 extracellular domain is the portion of the GUCYC2 protein that is exposed externally on the outside of the cell. The GUCYC2 extracellular domain includes a GUCYC2 the portion of the GUCYC2 protein that bind to the GUCYC2 protein's naturally occurring agonist ligands, guanylin and uroguanylin, as well as naturally occurring and synthetic agonist and antagonist ligands such as, for example, the *E. coli* heat stable enterotoxin ST. The GUCYC2 extracellular domain includes all amino acid residues of the sequence between the GUCYC2 signal sequence and the GUCYC2 transmembrane domain. That is, the GUCYC2 extracellular domain includes all amino acid residues from the first residue after the GUCYC2 signal sequence to the last residue before the GUCYC2 transmembrane domain.

These domains include a signal sequence, an extracellular domain, a transmembrane domain (as a bitopic or single-pass transmembrane protein, there is only a single transmembrane domain), a kinase homology domain and a guanylyl cyclase catalytic domain (the kinase homology domain and the guanylyl cyclase catalytic domain together are sometimes referred to interchangeably as an intracellular or cytoplasmic domain). The domains are described herein from the N-terminus to the C-terminus as they occur when the protein is produced in the cell.

The transmembrane domain is positioned within and spans the cell membrane. The transmembrane domain anchors the GCC protein in the cell membrane.

The kinase homology domain and guanylyl cyclase catalytic domain are positioned in the interior of the cell and function to relay the signal when the receptor is activated by its binding to an agonist ligand. The kinase homology domain is predicted to have tyrosine kinase activity; the guanylyl cyclase catalytic domain is predicted to have guanylyl cyclase activity.

As used herein, a "Ad5.Fib35 adenoviral vector" and a "Ad5.F35 adenoviral vector" are used interchangeably and refer to an adenoviral vector in which the DNA encoding the native Ad5 fiber or shaft and knob portion of the fiber has been replaced by those derived from serotype B adenovirus Ad35.

As used herein, a "replication defective adenoviral vector" means an adenoviral vector deficient in one or more regions of the adenoviral genome that are essential to viral replication (e.g., E1, E2 or E4 or combination thereof), and thus unable to propagate in the absence of trans-complementation (e.g., provided by either complementing cells or a helper virus). Also included within the definition of a "replication defective adenoviral vector" is minimal (or gutless) adenoviral vector which lacks all functional genes including early (E1. E2, E3 and E4) and late genes (L1, L2, L3, L4 and L5) with the exception of cis-acting sequences (see for example Kovesdi et al., Current Opinion in Biotechnology 8 (1997), 583-589; Yeh and Perricaudet, FASEB 11 (1997), 615-623; WO 94/12649; WO 94/28152). The replication-deficient adenoviral vector may be readily engineered by one skilled in the art, taking into consideration the required minimum sequences, and is not limited to these exemplary embodiments. Adenoviral vectors lacking E1, or E1 and E2, or E1 and E3, or E1 and E4, or E1 and E2 and E3, or E1 and E2 and E4, or E1 and E3 and E4, or E1 and E2 and E3 and E4 are all contemplated by this definition. As used herein, the term "gene expression cassette" means a DNA construct that is or can be inserted into an adenoviral backbone capable of driving expression of soluble GUCYC2 or a soluble GUCYC2 fused in frame to a universal CD4+ epitope. Gene expression cassettes generally are constructed to express one or more foreign antigens-of-interest under the control of a given promoter and may include a polyadenylation signal such as for example the BGH polyadenylation signal or those derived from SV40, and/or other elements, such as a Kozak region and/or additional termination signals not already provided by the host vector or the coding region to be expressed. Depending on numerous factors such as the size, composition, or complexity and the expression pattern of the chosen promoter, different promoters may be utilized. The CMV IE promoter is commonly used in a gene expression cassette because it is efficiently expressed in many tissue types. Other promoters might be used in gene expression cassette including, for example, simian virus 40 (SV40) early promoter, an Epstein-Barr virus immediate early promoter, a Rous sarcoma virus promoter, the human hemoglobin promoter, a dendritic cell specific such as promoter CD11c (Masood, R, et al, 2001 int J Mol Med 8: 335-343, Somia, N. V, et al. 1995 Proc Acad Sci USA 92: 7570-7574, which are incorporated herein by reference) as well as muscle specific promoters including the myosin promoter, the muscle creatinine kinase (MCK) promoter, the desmin promoter and the mammalian troponin 1 promoter.

As used herein the term "soluble GUCYC2", "soluble GCC", "soluble human GUCYC2", "soluble human GCC", "soluble GUCYC2 domain", "soluble GCC domain", "soluble human GUCYC2 domain" and "soluble human GCC domain" are used interchangeably and refer to a fragment of human GUCY2C that comprises a GUCY2C extracellular domain or a fragment thereof comprising a sequence from human GUCY2C that is at least 330-423 amino acid residues including the sequence from amino acid residue 54 to amino acid residue 384 of the functional mature GCC protein, and optionally fused with a portion of GUCYC2 transmembrane domain while still permitting extracellular secretion of soluble GUCYC2 untethered to the cell membrane. That is, to the extent any sequence from the GUCYC2 transmembrane domain is included, it is insufficient to function as an anchor. According, when expressed in a cell, the soluble GUCYC2 can be secreted by the cell. It is understood that the secretion of soluble GCC is facilitated by a signal sequence and that a nucleic acid encoding soluble GCC would code for either an endogenous or exogenous signal sequence. A soluble GUCYC2 may be linked to a signal peptide such as a GUCYC2 signal peptide and include additional amino acids.

As used herein, "a secretion signal", "a secretion peptide, "a signal peptide" and "signal sequence" are used interchangeably and meant to refer to an amino acid sequence of a protein which when present results in the transportation and secretion of the protein to the exterior of the cell. Secretion signals are typically cleavable hydrophobic segments of a precursor protein at or near the N terminus of the precursor protein. In the secretion process, such secretion signals are enzymatically removed to result in the secretion of a mature form of the protein, i.e. a form of the protein lacking the secretion signal. In some embodiments, the secretion signal is a GCC secretion signal derived from GCC protein. The GCC secretion signal is the N-terminus signal peptide comprising residues 1 to about residues 21, 22 or 23 of GUCYC2. In some embodiments, the secretion signal is derived for a source different from GUCYC2 (an "exogenous signal sequence") and replaces the endogenous signal sequence. In the case of the former, the coding sequence of the GCC antigen including the signal sequence is used intact. In the case of the latter, a nucleotide sequence encoding the signal sequence from another source is linked to the coding sequence GCC in place of the naturally occurring signal sequence and in frame with the rest of the protein. In such cases, the signal sequence may be any such sequence which is functional in the cells of the individual to whom the genetic construct is administered.

As used herein, "universal CD4+ helper epitope" is peptide sequence that forms a complex with several Major Histocompatibility Complex (MIC) Class 2 human leukocyte antigens (HLA) the complex is then recognized by T cell receptors on CD4+ T cells and are discussed in detail below As used herein, "GUCY2C-expressing tumors" refers to tumors expressing guanylyl cyclase C or "GCC". Such tumor/cancer cells generally originate within the gastrointestinal tract and include but are not limited to tumors/cancer cells of esophageal, gastric, pancreatic, or colorectal origin. Such tumors may be primary or metastatic.

As used herein, the term "colorectal tumor" or "cancer occurring within the colorectal tract" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" or "cancer occurring within the colorectal tract" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain GCC.

As used herein, the terms "stomach cancer" or "gastric cancer" are meant to include the well-accepted medical definition that defines stomach cancer as a medical condition characterized by cancer of cells of the stomach.

As used herein, the term "esophageal cancer" is meant to include the well-accepted medical definition that defines esophageal cancer as a medical condition characterized by cancer of cells of the esophagus.

As used herein, the term "pancreatic cancer" is meant to include the well-accepted medical definition that defines pancreatic cancer as a medical condition characterized by cancer of cells of the pancreas.

As used herein a "primary tumor" is one confined to the original tissue of origin. This is as opposed to a metastatic tumor which has disseminated from the primary tissue of origin to other organs.

As used herein "outside of the colorectal tract" refers to organs not within the colorectal tract.

The deleted adenoviral genes are replaced by a gene expression cassette which drives expression of the foreign transgene. These deleted vectors are usually constructed from plasmids or Ad DNA containing the genetically modified Ad genome, and the vectors are grown up on complementing cell lines such as HEK293, PER.C6, or N52.E6 which retain and express the necessary essential genes.

A functional mature GCC protein is produced when the signal sequence is excised. The functional mature GCC protein typically includes amino acid residues 22-1073 of SEQ ID NO:2, amino acid residues 23-1073 of SEQ ID NO:2 or amino acid residues 24-1073 of SEQ ID NO:2. The mature GCC proteins this comprises the extracellular domain, the transmembrane domain, the kinase homology domain and the guanylyl cyclase catalytic domain.

The extracellular domain of the functional mature GCC protein typically includes about 330-423 amino acid residues including the sequence from amino acid residue 54 to amino acid residue 384 of the functional mature GCC protein. The extracellular domain may include the sequence from amino acid residues 22, 23 or 24 to amino acid residues 420 to 435 of the functional mature GCC protein. The sequence of extracellular domain of the functional mature GCC protein may include the sequence from amino acid residues 22 to amino acid residues 435 of the functional mature GCC protein or a 330-422 amino acid residue fragment of the sequence from amino acid residues 22 to amino acid residues 435 of the functional mature GCC protein that includes the sequence from about amino acid residues 54 to about amino acid residue 384 of the functional mature GCC protein, such as for example the sequence from amino acid residues 22, 23 or 24 to amino acid residues 420 to 435 of the functional mature GCC protein. The extracellular domain of GCC does not have homology with guanylyl cyclases A, B and G which have broad tissue distribution and different ligand specificities.

The transmembrane domain of the functional mature GCC protein typically includes about 16-23 amino acid residues including the sequence from about amino acid residue 436 to about amino acid residue 452 of the functional mature GCC protein. The transmembrane domain may include the sequence from about amino acid residue 431 to about amino acid residue 454 of the functional mature GCC protein or a 16-22 amino acid fragment of the sequence from about amino acid residue 431 to about amino acid residue 454 of the functional mature GCC protein such as for example the sequence from about amino acid residue 436 to about amino acid residue 452 of the functional mature GCC protein or the sequence from about amino acid residue 431 to about amino acid residue 454 of the functional mature GCC protein.

The kinase homology domain of the functional mature GCC protein typically includes about 237-260 amino acid residues including the sequence from about amino acid residue 508 to about amino acid residue 745 of the functional mature GCC protein. The kinase homology domain may include the sequence from about amino acid residue 489 to about amino acid residue 749 of the functional mature GCC protein or a 237-259 amino acid fragment of the sequence from about amino acid residue 489 to about amino acid residue 749 of the functional mature GCC protein such as for example the sequence from about amino acid residue 508 to about amino acid residue 745 of the functional mature GCC protein or the sequence from about amino acid residue 489 to about amino acid residue 749 of the functional mature GCC protein.

The guanylyl cyclase catalytic domain of the functional mature GCC protein typically includes about 186-257 amino acid residues including the sequence from about amino acid residue 816 to about amino acid residue 1002 of the functional mature GCC protein. The guanylyl cyclase catalytic domain may include the sequence from about amino acid residue 750 to about amino acid residue 1007 of the functional mature GCC protein or a 186-256 amino acid fragment of the sequence from about amino acid residue 750 to about amino acid residue 1007 of the functional mature GCC protein such as for example the sequence from about amino acid residue 816 to about amino acid residue 1002 of the functional mature GCC protein or the sequence from about amino acid residue 750 to about amino acid residue 1007 of the functional mature GCC protein.

The soluble GCC of the present invention are preferably expressed as a fusion protein in which soluble GCC and a universal CD4+ T epitope are expressed as a single polypeptide. Thus, the sequence encoding the soluble GCC will preferably be linked to the sequence encoding the universal CD4+ T epitope such that an in frame translational fusion of the two regions results. The universal CD4+ helper epitope may be attached at either the N or C terminus of the soluble GCC. If attached at the N terminus it is inserted downstream of the endogenous or an exogenous signal sequence.

A truncated GUCYC2 which comprises the GCC signal sequence and extracellular domain of the molecule which in the aggregate consists of about the first 429 amino acid residues of GCC fused at the C terminus to a universal CD4+ helper epitope (PADRE) is exemplified herein.

Methods of detecting tumor markers such as GCC are well known in the art. For example, expression may be detected as protein levels or as mRNA levels. Techniques such as qRT-PCR branched oligonucleotide technology, Panomics QuantiGene® 2.0 (Atffymetrix, Inc. Santa Clara, Calif.) Quantitative Gene expression reagents and assays, MassARRAY® (Sequenom, Inc. San Diego, Calif.) Quantitative Gene Expression systems in situ hybridization using detectable probes (such as FISH), dot blots assays, and other RNA quantitative amplification techniques and Northern Blots are useful for measuring mRNA levels and protein mass spectrometry including protein and peptide fractionation coupled with mass spectrometry, immunohistochemistry using detectable binding agents, immunoassays such as ELISA or Western blots, QProteome FFPE Qiagen Valencia Calif., reverse phase protein microarrays are useful for detecting protein markers presence and levels. US Patent Publication No. 20170049869A1 describes RT-PCT methods of detection as applicable to GCC. US Patent Publication No. 20180355062 describes anti-GCC antibody molecules.

2.0 Overview

Prophylactic and therapeutic vaccines for protecting or treating individuals against primary and/or metastatic GUCY2C-expressing tumors are provided. Compositions useful to make such vaccines and methods of making and using the vaccines are provided.

One of the greatest impediments to cancer immunotherapy is the paucity of antigens that are tumor-specific, sufficiently immunogenic, and shared among patients. In lieu of ideal targets, antitumor immune responses are generally directed to tissue-specific rather than tumor-specific proteins. Barriers to using self-antigens include the potential development of concomitant autoimmunity and tolerance, which limits immunotherapeutic efficacy. Attempts to circumvent these limitations have included the use of self-proteins that are expressed in immunologically privileged compartments. Their ectopic expression in tumors outside the restricted compartments provides opportunities for targeted Guanylyl cyclase C (GCC), the receptor for diarrheagenic bacterial heat-stable enterotoxins and the endogenous paracrine hormones guanylin and uroguanylin, is expressed in apical membranes of intestinal epithelial cells, restricting it to mucosal immune compartments. The vaccines of the present invention are useful for prophylactic or therapeutic immunization of human patients with GUCY2C-expressing cancers including esophageal, gastric, pancreatic, and colorectal cancer without inducing autoimmunity.

Some embodiments provide a modified adenovirus vector-based vaccine for cancer, particularly colorectal cancer, and immunotherapy as well as cancer prevention, screening, early detection, diagnosis, treatment, and/or survivorship that affect the general population. The vaccine uses a modified version of a recombinant adenovirus vector in which viral protein F35 is included to replace the corresponding adenovirus protein of adenovirus 5. The modified adenovirus vector may be referred to as Ad5.F35 and comprises coding sequences for fusion protein that includes cancer associated protein sequences, such as portions of a cancer associated protein GUCY2C extracellular domain sequences linked to T cell epitopes. The modified adenovirus vector-based anti-GUCY2C vaccine is used to deliver the colorectal cancer protein to immune cells within the body to educate them against colorectal cancer. Some of these educated immune cells may then be able to search for and kill colorectal cancer hiding in the body. Some of these educated immune cells may then be able to produce or induce production of antibodies that target cells expressing the colorectal cancer protein. Some of these educated immune cells may then be able to induce production of antibodies and immune cells that target cells expressing the colorectal cancer protein.

Some embodiments provide a Listeria vaccine for cancer, particularly colorectal cancer, and immunotherapy as well as cancer prevention, screening, early detection, diagnosis, treatment, and/or survivorship that affect the general population. The vaccine uses a "crippled" version of *Listeria monocytogenes* to deliver a colorectal cancer protein to immune cells within the body to educate them against cells that express the colorectal cancer associated protein. These educated immune cells may then be able to search for and kill cancer that expresses the protein and that are hiding in the body.

Some embodiments provide prime boost method of vaccinating against cancer particularly colorectal cancer cells that express a cancer associated protein such as the colorectal cancer associated protein GUCY2C. A combination of an adenovirus based GUCY2C vaccine with a modified *Listeria monocytogenes* produces immune responses superior to those using either vaccine alone.

Effective immune responses against GUCY2C are useful to treat any cancer that expresses such proteins such as metastatic colorectal cancer, a disease that is typically fatal as well as several other cancers that express the protein GUCY2C such as pancreatic, stomach, and esophageal.

3.0 Adenovirus Based Anti-GUCY2C Vaccines (Ad5-GUCY2C$_{ECD}$T-Cell Epitope)

Adenoviruses represent a widely used viral-vectored platform for vaccine design. We have previously demonstrated that adenovirus (Ad5) and DNA based vaccines against GUCY2C generate GUCY2C-specific T cell responses yielding antitumor immunity. Recombinant adenovirus particles expressing a chimeric protein comprising GCC$_{ECD}$ linked to CD4+ helper epitopes are disclosed in co-pending application Ser. No. 13/120,144, which is incorporated herein by reference. The various GUCY2C$_{ECD}$T-cell epitope constructs described herein may be used with the adenovirus Ad5 vector to produce anti-GUCY2C vaccines.

Most currently used adenovirus vectors for gene expression in humans rely on serotype 5 Ad vectors. Adenovirus infection is initiated by the attachment of Ad 5 to the cell surface via the fiber protein (Shenk, T. 1996 Fields Virology, Volume 2, Fields, B N et al. (Eds), Volume 2, Lippincott-Raven, Philadelphia, PA, 2111-2148). The distal C-terminal domain of the trimeric fiber molecule ends in a "Knob" that binds to a specific cellular receptor, which for Ad5 is the coxsackie adenovirus receptor (CAR) (Bergelson, J M et al. Science, 275, 1320-1323). After binding the cellular internalization interact in an event which is independent of the virus attachment, Arg-Gly-Asp (RGD-motifs) in the penton base with cellular integrins.

Ad5 is a natural human pathogen, producing mild infections in nearly the entire human population (Yu, B., et al. (2012) J Med Virol 84(9): 1408-1414). These natural exposures induce Ad5-specific neutralizing antibodies (NAbs) that limit reinfection or Ad5-based vaccination by preventing infection of host cells, a necessary step in target antigen expression and induction of immune responses (Priddy, F. H., et al. (2008) Clin Infect Dis 46(11): 1769-1781; Schirmbeck, R., et al. (2008) Mol Ther 16(9): 1609-1616; Small, J. C., et al. (2014) J Leukoc Biol 96(5): 821-831).

We have shown that immunization of mice with a human adenovirus type 5 (Ad5) expressing guanylyl cyclase C (GUCY2C) vaccine (Ad5-GUCY2C) elicits immune responses to GUCY2C and immunity against colorectal cancer. (Snook A E, et al. J Natl Cancer Inst. 2008:100(13): 950-6). We have extended that observation to humans in a Phase I clinical trial. Example 1 reports a correlation between Ad5 neutralizing antibody GUCY2C-specific T-cell responses in which responses were significantly greater in Ad5 NAb Low patients. One-time immunization against GUCY2C can in some individuals produce limited antitumor immunity and repeated immunization with Ad5-

GUCY2C can be rendered ineffective due to vaccine-induced Ad5 neutralizing antibodies following administration.

4.0 Modified-Adenovirus Based Vaccines

4.1 Ad5F35 Vectors

Naturally-occurring Ad5 NAbs target the fiber molecule on the surface of Ad5 (Cheng, C., et al. (2010) J Virol 84(1): 630-638). This might suggest that replacement of the fiber molecule in Ad5 with the fiber molecule from the B group adenovirus Ad35 (to which few human subjects have natural immunity) might produce a chimeric Ad5 viral vector (known as Ad5.F35) that is not affected by naturally-occurring Ad5 immunity. Sumida et al. have found that functionally significant Ad5-specific NAbs are directed primarily against the Ad5 hexon protein. (Sumida et al, Journal of Immunology (2005) 174 (11) 7179-7185). Hong et al. have reported significant neutralizing effect with respect to antibodies directed to the penton base. (Hong S. S. et al. J. Virol. 2003; 77: 10366-10375)

Vectors containing B-group Ad fibers, including Ad5.F35 vectors, use CD46 for initial cellular attachment (Gaggar, A., et al. (2003). Nat. Med. 9: 1408-1412). In humans, CD46 is expressed on all nucleated cells at a low level. Although Ad5.F35 vectors efficiently transduce dendritic cells in vitro and potentially in vivo, a number of findings might argue against the utility of these vectors for in vivo vaccination. (i) CD46 signaling (upon binding of CD46 monoclonal antibodies, recombinant complement factor C3b, or measles virus hemagglutinin) can induce immunosuppression (Schneider-Schaulies, S., and ter Meulen, V. (2002). Springer Semin. Immunopathol. 24: 127-148). (ii) Studies of an Ad35 outbreak leading to pneumonia and sepsis revealed a transient neutropenia, which could have been caused directly by Ad35 infection (Sanchez, M. P., et al. (1997). J. Infect. Dis. 176: 760-763). (iii) Measles virus and HHV6, which also use CD46 as a receptor, can cause transient immunosuppression at the level of dendritic cell precursors, bone marrow stromal cells, or CD34+ myeloid progenitors (Manchester, M., et al. (2002). J. Virol. 76: 6636-6642). These considerations have resulted in studies with mixed results. One study noting the factors above, found that that AD5.F35 vaccination to a test antigen (hepatitis B core antigen) did not induce immunosuppression in CD46 transgenic mice and noted that their results might be antigen specific (DiPaolo N, et al. Mol Ther. 2006; 13(4):756-765). A study in primates however found that an Ad5.Fib35 with a measles haemagglutinin vaccine insert had a reduced insert specific humoral and cellular immune response than animals similarly immunized with Ad5 (Ophorst, O. J., et al. (2004). Vaccine 22: 3035-3044).

The present invention comprises a chimeric adenoviral vaccine vector Ad5.F35 comprising: a) an Ad5.F35 vector; and a gene expression cassette comprising: i) a nucleic acid encoding a soluble human GUCY2C domain; ii) a heterologous promoter operatively linked to the nucleic acid encoding the soluble human GUCY2C domain; and iii) a universal CD4+ helper epitope as well as vaccines and methods relying thereon.

The adenoviral vector of the invention can be replication-competent. Preferably, however, the adenoviral vector is replication-deficient in host cells.

EP 1 693 459 A1, WO 2000/073478 A9 and EP 1 322 774 A2, which are each incorporated herein by reference, describe chimeric Ad5.F35 vectors to modify the tropism (cell/tissue targeted by the virus) of Ad5. None describe insensitivity to Ad5 neutralizing immunity.

The construction of chimeric Ad5.Fib35 virus vectors has been described by Shayakhmetov et al. via a twostep PCR approach in which three fragments are amplified: (i) the Ad5 fiber non-translated region and the first 132 bp of the fiber tail domain; (ii) the Ad35 shaft and knob domains; and; (iii) the Ad5E4 region including the Ad5 fiber polyadenylation signal. After purification of the resultant fragments, they are combined and subjected to an additional PCR reaction primed by forward and reverse primers directed to the correct ends of the chimeric fiber. The resultant amplified fragment is then substituted into a donor plasmid by ligation and the substitution of the chimeric fiber is performed by recombination with the vector genome contained within a plasmid in a Rec+*E. coli* strain BJ5183. To produce the corresponding viruses, clones verified to be correct were digested with the restriction enzyme PacI to release the viral genomes and transfected onto 293 cells (Shayakhmetov D M et al. J Virol 2000; 74: 2567-2583). EP1550722B1 describes a similar procedure of direct replacement of the Ad5 fiber sequence in a donor vector and subsequent recombination and amplification.

Numerous strategies have been developed to construct Ad vectors carrying a foreign gene insert. Traditionally, Ad vectors were constructed using two standard methods. The first method is the in vitro ligation method involving the ligation of a DNA fragment obtained by restriction digesting of a plasmid carrying the foreign gene insert flanked by Ad sequences with a DNA fragment representing the rest of Ad genome (Stow ND. J Virol. 1981; 37:171-80). The second method consisted of homologous recombination in permissive cell lines between two plasmids the shuttle plasmid carrying the foreign gene insert flanked by Ad sequences for site-specific insertion and the genomic plasmid carrying almost the entire Ad genome. (Bett A J, et al. Proc Natl Acad Sci USA. 1994; 91:8802-6. These classic methods of vector construction usually have low efficiency and sometimes can be contaminated with the parental virus.

Alternate approaches have been developed to circumvent the limitations of traditional methods. One such strategy is based on the highly efficient homologous recombination machinery of *E. coli* (BJ5183) to generate Ad vectors [16-19]. Homologous recombination between a linearized or intact plasmid containing almost an entire Ad genome and a shuttle plasmid containing an exogenous expression cassette flanked by homologous sequences from the site of insertion in the Ad genome generates an infectious clone with a modification and/or insertion in the desired region. A similar strategy employing homologous recombination in yeasts has been reported [20]. This strategy involves homologous recombination between Ad DNA and the yeast artificial chromosome (YAC) vector containing sequences from the left and the right termini of Ad genome, resulting in the generation of a yeast artificial chromosome containing an infectious copy of Ad genome. Transfection of the excised Ad genome into appropriate cells results in generation of infectious virions.

In order to overcome the low efficiency of homologous recombination in mammalian cells, approaches based on bacteriophage P1 Cre/LoxP recombination system have been developed. (Aoki K, et al. Mol Med. 1999; 5:224-31; Hardy S, et al. J Virol. 1997; 71:1842-9; Ng et al. Hum Gene Ther. 1999; 10:2667-72; Ng et al. Hum Gene Ther. 2000; 11:693-9; Ng et al. J Virol. 2002; 76:4181-9.

Ad vectors are generated as a result of Cre-mediated site-specific recombination between two plasmids after their co-transfection into a suitable cell line expressing Cre recombinase. Frequency of vector generation using Cre/LoxP-based system has been found to be 30 to 100-fold higher compared to the traditional homologous recombination methods.

4.2 GUCY2C$_{ECD}$

A functional mature GCC protein is produced when the signal sequence is excised. The functional mature GCC protein typically includes amino acid residues 22-1073 of SEQ ID NO:2, amino acid residues 23-1073 of SEQ ID NO:2 or amino acid residues 24-1073 of SEQ ID NO:2. The mature GCC proteins comprises the extracellular domain, the transmembrane domain, the kinase homology domain and the guanylyl cyclase catalytic domain.

Vaccines comprise soluble truncated forms of GCC protein which comprise extracellular domain of the functional mature GCC protein, which typically includes about 330-423 amino acid residues including the sequence from amino acid residue 54 to amino acid residue 384 of the functional mature GCC protein. The extracellular domain may include the sequence from amino acid residues 22, 23 or 24 to amino acid residues 420 to 435 of the functional mature GCC protein. The sequence of extracellular domain of the functional mature GCC protein may include the sequence from amino acid residues 22 to amino acid residues 435 of the functional mature GCC protein or a 330-422 amino acid residue fragment of the sequence from amino acid residues 22 to amino acid residues 435 of the functional mature GCC protein that includes the sequence from about amino acid residues 54 to about amino acid residue 384 of the functional mature GCC protein, such as for example the sequence from amino acid residues 22, 23 or 24 to amino acid residues 420 to 435 of the functional mature GCC protein. Constructs may also include sequences from the transmembrane domain provided they are not sufficient to function to prevent the soluble GCC construct from becoming anchored in the cell membrane. The transmembrane domain of the functional mature GCC protein typically includes about 16-23 amino acid residues including the sequence from about amino acid residue 436 to about amino acid residue 452 of the functional mature GCC protein. The transmembrane domain may include the sequence from about amino acid residue 431 to about amino acid residue 454 of the functional mature GCC protein or a 16-22 amino acid fragment of the sequence from about amino acid residue 431 to about amino acid residue 454 of the functional mature GCC protein such as for example the sequence from about amino acid residue 436 to about amino acid residue 452 of the functional mature GCC protein or the sequence from about amino acid residue 431 to about amino acid residue 454 of the functional mature GCC protein. In some preferred embodiments, no transmembrane sequences are included.

4.3 Universal CD4+ Helper Epitopes

To induce improved anti-GUCY2C immune responses, a universal CD4+ helper epitope may be linked to GUCY2C sequences to produce a fusion protein. A universal CD4+ helper epitope is a peptide sequence which is a match for and therefore recognized by multiple HLA types. An example of a universal CD4+ helper epitope is a PADRE (Pan DR epitope peptides).

The PADRE peptides forms complexes with at least 15 of the 16 most common types of HLA-DR. Since humans have at least one DR and PADRE binds to many of its types, PADRE has a high likelihood of being effective in most humans. Universal CD4+ helper epitopes, such as PADRE and others are disclosed in U.S. Pat. No. 5,736,142 issued Apr. 7, 1998 to Sette, et al.; U.S. Pat. No. 6,413,935 issued Jul. 2, 2002 to Sette, et al.; and U.S. Pat. No. 7,202,351 issued Apr. 10, 2007 to Sette, et al and WO1995007707A1.

The universal HLA-DR epitope PADRE (KXVAAW-TLKA) has been described.

(Alexander, J, et al. J. Immunol, 2000 Feb. 1, 164(3): 1625-33; Agadjanyan et al. J Immunol 2005; 174:1580-6).

When PADRE is fused to a protein antigen several investigators have used the peptide sequence AKFVAAW-TLKAAA expressed in frame with the antigen of interest.

Wei J. et al. Cancer Biother Radiopharm 2008, 23:121-8;

Bargieri D Y et al. Mem Inst Oswaldo Cruz 2007, 102:313-7;

The T cell epitope present in the 33 kDa C-terminal region of *P. vivax* MSP1 DYDVVYLKPLAGMYK (SEQ ID NO:12) has also been found to elicit a strong immune response in non-human primates with different class II HLA haplotypes (Rosa et. al. Microbes Infect 2006, 8:2130-7;

Sinigaglia et al., Nature 336, 778-780 (1988) describes *Plasmodium falciparum* peptides derived from the circumsporozoite protein recognized by T cells in association with many different MHC class II molecules in mouse and man. Peptides derived from residue positions 378-398 DIEKKI-AKMEKASSVFNVVNS (SEQ ID NO:13), and N and C deletions thereof for example IEKKIAKME-KASSVFNVVNS (SEQ ID NO:14). EKKIAKME-KASSVFNVVNS (SEQ ID NO 15). DIEKKIAKME-KASSVFNVVN (SEQ ID NO:16), DIEKKIAKMEKASSVFNVV (SEQ ID NO:17), DIEKKI-AKMEKASSVFNV (SEQ ID NO:18) elicited strong responses.

Provided herein are examples of different proteins and different peptides which are examples of proteins which contain such CD4+ T cell epitopes. These proteins and peptides are intended to be non-limiting examples of CD4+ T cell epitopes.

In some embodiments, the CD4+ T cell epitope may be derived from tetanus toxin for example $TT_{830-844}$ QYIKAN-SKFIGITEL (SEQ ID NO:19), and $TT_{947-967}$ FNNFTVSFWLRVPKVSASHLE (SEQ ID NO:20) Panina-Bordignon et al., Eur. J. Immunol. 19, 2237-2242 (1989); Renard V, J Immunol 2003; 171:1588-95; $TT_{590-603}$ TKIYSYFPSVISKV (SEQ ID NO:21), $TT_{615-629}$ VRDI-IDDFTNESSQK (SEQ ID NO:22), $TT_{639-652}$ VSTIVPYIGPALNI (SEQ ID NO:23), $TT_{830-843}$ QYIKAN-SKFIGITE (SEQ ID NO:24) and $TT_{947-967}$ FNNFTVSFWLRVPKVSASHLE (SEQ ID NO:25) Ben-Mohamed et al. Hum Immunol 2000; 61:764-79;

In some embodiments, the CD4+ T cell epitope may be derived from Influenza hemagglutinin for example influenza hemagglutinin residues 306-318 PKYVKQNTLKLAT (SEQ ID NO:26). (Busch et al., Int. Immunol. 2, 443-451 (1990); Mom et al. BMC Immunol 2005; 6:24).

In some embodiments, the CD4+ T cell epitope may be derived from Hepatitis B surface antigen (HBsAg) (Litjens et al. J Immunol Methods 2008; 330:1-11).

In some embodiments, the CD4+ T cell epitope may be derived from outer membrane proteins (OMPs) of bacterial pathogens (such as Anaplasma marginals) (Macmillan H, Norimine J, Brayton K A, Palmer G H, Brown W C. Physical linkage of naturally complexed bacterial outer membrane proteins enhances immunogenicity. Infect Immun 2008; 76:1223-9).

In some embodiments, the CD4+ T cell epitope may be derived from the VP1 capsid protein from enterovirus 71 (EV71) strain 41 for example residues 66-77 IETRCVLNSHSTAET (SEQ ID NO:27), residues 145-159 EVVPQLLQYMFVPPG (SEQ ID NO:28), and residues 247-261 LVVRIYMRMKHVRAW (SEQ ID NO:29). (Wei Foo et al. Viral Immunol 2008).

In some embodiments, the CD4+ T cell epitope may be derived from EBV BMLF1 (Schlienger K, Craighead N, Lee K P, Levine B L, June C H. Efficient priming of protein antigen-specific human CD4(+) T cells by monocyte-derived dendritic cells. Blood 2000; 96:3490-8; Neidhart J, Allen K O, Barlow D L, Carpenter M, Shaw D R, Triozzi P L, Conry R M. Immunization of colorectal cancer patients with recombinant baculovirus-derived KSA (Ep-CAM) formulated with monophosphoryl lipid A in liposomal emulsion, with and without granulocyte-macrophage colony-stimulating factor. Vaccine 2004; 22:773-80; Piriou E R, van Dort K, Nanlohy N M, van Oers M H, Miedema F, van Baarle D. Novel method for detection of virus-specific CD4+ T cells indicates a decreased EBV-specific CD4+ T cell response in untreated HIV-infected subjects. Eur J Immunol 2005; 35:796-805; Heller K N, Upshaw J, Seyoum B, Zebroski H, Munz C. Distinct memory CD4+ T-cell subsets mediate immune recognition of Epstein Barr virus nuclear antigen 1 in healthy virus carriers. Blood 2007; 109:1138-46).

In some embodiments, the CD4+ T cell epitope may be derived from EBV LMPI for example $LMP_{1159-175}$ YLQQNWWTLLVDLLWLL (SEQ ID NO:30) Kobayashi et al. Cancer Res 2008; 68:901-8).

In some embodiments, the CD4+ T cell epitope may be derived from HIV Gag p24 for example $Gag_{131-15}$ NYPIVQNIQGQMVHQAISPR (SEQ ID NO:31), $Gag_{211-230}$ EWDRVHPVHAGPIAPGQMRE (SEQ ID NO:32), $Gag_{241-260}$ STLQEQIGWMTNNPPIPVGE (SEQ ID NO:33), $Gag_{263-277}$ KRWIILGLNKIVRMY (SEQ ID NO:34), $Gag_{271-290}$ NKIVRMYSPTSILDIRQGPK (SEQ ID NO:35), $Gag_{291-310}$ EPFRDYVDRFYKTLRAEQAS (SEQ ID NO:36), $Gag_{301-320}$ YKTLRAEQASQEVKNWMTET (SEQ ID NO:37), $Gag_{321-340}$ LLVQNANPDCKTILKALGPA (SEQ ID NO:38), $Gag_{331-350}$ KTILKALGPAATLEEMMTAC (SEQ ID NO:39), (Pajot et al. Eur J Immunol 2007; 37:2635-44).

In some embodiments, the CD4+ T cell epitope may be derived from Adenovirus 5 hexon protein for example the residues found at position 556 to 580 VPFHIQVPQKFFAIKNLLLLPGSYT (SEQ ID NO:40), residues 56-80 VTTDRSQRLTLRFIPVDREDTAYSY (SEQ ID NO:41), residues 316-335 GQQSMPNRPNYIAFRDNFIG (SEQ ID NO:42) and residues 906-930 EVDPMDEPTLLYVLFEVFDVVRVHRPHR (SEQ ID NO:43) (Leen et al. J Virol 2008; 82:546-54). In all There are >30 identified CD4+ T cell epitopes for multiple MHC-II haplotypes.

In some embodiments, the CD4+ T cell epitope may be derived from Vaccinia virus proteins for example the F17R protein residues at residues 21 through 29 (YLVLKAVKV) and the A10L protein residues at residues 20-28 FRIVSTVLP. (Calvo-Calle et al. PLoS Pathog 2007; 3:1511-29) Calvo-Calle identified >25 CD4+ T cell epitopes for multiple MHC-II haplotypes from 24 different vaccinia proteins.

In some embodiments, the CD4+ T cell epitopes are derived from *Mycobacterium tuberculosis* heat shock protein (Liu D W. Tsao Y P, Kung J T, Ding Y A, Sytwu H K, Xiao X, Chen S L. Recombinant adeno-associated virus expressing human papillomavirus type 16 E7 peptide DNA fused with heat shock protein DNA as a potential vaccine for cervical cancer. J Virol 2000; 74:2888-94.)

In some embodiments, the CD4+ T cell epitopes are derived from the Fc portion of IgG (You Z, Huang X F, Hester J, Rollins L, Rooney C, Chen S Y. Induction of vigorous helper and cytotoxic T cell as well as B cell responses by dendritic cells expressing a modified antigen targeting receptor-mediated internalization pathway. J Immunol 2000; 165:4581-91).

In some embodiments, the CD4+ T cell epitopes are derived from lysosomal targeting signal of the human LAMP-1 protein (Su Z, Vieweg J. Weizer A Z, Dahm P, Yancey D, Turaga V, Higgins J, Boczkowski D, Gilboa E, Dannull J. Enhanced induction of telomerase-specific CD4 (+) T cells using dendritic cells transfected with RNA encoding a chimeric gene product. Cancer Res 2002: 62:5041-8).

A sample of HLA haplotypes as well as representative CD4+ T cell epitopes for the indicated HLA molecule include, but are not limited to, the following:

HLA-DR*1101—Tetanus Toxoid peptide residues 829-844. Hemagglutinin peptide residues 306-318 (Moro M, Cecconi V, Martinoli C, Dallegno E, Giabbai B, Degano M, Glaichenhaus N, Protti M P, Dellabona P, Casorati G. Generation of functional HLA-DR*1101 tetramers receptive for loading with pathogen- or tumour-derived synthetic peptides. BMC Immunol 2005; 6:24.)

HLA-DRB1*0101 (DR1)—Tetanus Toxoid peptide residues 639-652, 830-843 or 947-967 and 14 other tetanus toxoid peptides (BenMohamed L, Krishnan R, Longmate J, Auge C, Low L, Primus J, Diamond D J. Induction of CTL response by a minimal epitope vaccine in HLA A*0201/DR 1 transgenic mice: dependence on HLA class II restricted T(H) response. Hum Immunol 2000; 61:764-79; and James E A, Bui J, Berger D, Huston L, Roti M, Kwok W Long mate. Tetramer-guided epitope mapping reveals broad, individualized repertoires of tetanus toxin-specific CD4+ T cells and suggests HLA-based differences in epitope recognition. Int Immunol 2007; 19:1291-301).

HLA-DRB1*0301—EV71 VP1 residues 145-159 or 247-261 and 5 different tetanus toxoid peptides (Wei Foo D G, Macary P A, Alonso S, Poh C L. Identification of Human CD4(+) T-Cell Epitopes on the VP1 Capsid Protein of Enterovirus 71. Viral Immunol 2008; and James E A, Bui J, Berger D, Huston L, Roti M. Kwok W Pooh. Tetramer-guided epitope mapping reveals broad, individualized repertoires of tetanus toxin-specific CD4+ T cells and suggests HLA-based differences in epitope recognition. Int Immunol 2007; 19:1291-301).

HLA-DRB1*0405—EV71 VP1 residues 145-159 or 247-261 (Wei Foo D G, Macary P A, Alonso S, Poh C L. Identification of Human CD4(+) T-Cell Epitopes on the VP1 Capsid Protein of Enterovirus 71. Viral Immunol 2008).

HLA-DRB1*1301—EV71 VP1 residues 145-159 or 247-261 (Wei Foo D G, Macary P A, Alonso S, Poh C L. Identification of Human CD4(+) T-Cell Epitopes on the VP 1 Capsid Protein of Enterovirus 71. Viral Immunol 2008).

HLA-DR9—Epstein Barr virus (EBV) latent membrane protein 1 (LMP1) residues 159-175 (Kobayashi H, Nagato T, Takahara M, Sato K, Kimura S, Aoki N, Azumi M, Tateno M, Harabuchi Y, Celis E. Induction of EBV-latent membrane protein 1-specific MHC class II-restricted T-cell responses against natural killer lymphoma cells. Cancer Res 2008; 68:901-8).

HLA-DR53 EBV LMP1 residues 159-175 (Kobayashi H, Nagato T, Takahara M, Sato K. Kimura S, Aoki N. Azumi M, Tateno M, Harabuchi Y, Celis E. Induction of EBV-latent membrane protein 1-specific MHC class II-restricted T-cell responses against natural killer lymphoma cells. Cancer Res 2008; 68:901-8).

HLA-DR15 EBV LMP1 residues 159-175 (Kobayashi H. Nagato T. Takahara M, Sato K, Kimura S, Aoki N, Azumi M, Tateno M, Harabuchi Y, Celis E. Induction of EBV-latent membrane protein 1-specific MHC class II-restricted T-cell responses against natural killer lymphoma cells. Cancer Res 2008: 68:901-8).

HLA-DRB1*0401—15 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301).

HLA-DRB1*0701—9 different Tetanus Toxoid peptides (James E A. Bui J, Berger D. Huston L, Rod M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301).

HLA-DRB1*1501—7 different Tetanus Toxoid peptides (James E A, Bui J. Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301).

HLA-DRB5*0101—8 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301).

4.4 AD5.F35-GUCY2C Vaccine Constructs

As used herein AD5.F35-GUCY2C, AD5.F35-GUCY2C$_{ECD}$, AD5.F35-GUCY2C-universal T cell epitope, AD5.F35-GUCY2C$_{ECD}$-universal T cell epitope, are used interchangeably to refer to Ad5.F35 adenovirus vectors with the genetic insert encoding GUCY2C$_{ECD}$ linked to a universal T cell epitope such that infection with the vaccine results in the GUCY2C$_{ECD}$ linked to a universal T cell epitope fusion protein being expressed and secreted by infected cells. In preferred embodiments the universal T cell epitope of the AD5.F35-GUCY2C vaccine is the universal T cell epitope PADRE. Thus, preferred embodiments may be referred to, interchangeably as AD5.F35-GUCY2C-PADRE and AD5.F35-GUCY2C$_{ECD}$-PADRE. All references to methods of using AD5.F35-GUCY2C vaccine are intended to describe the general AD5.F35-GUCY2C vaccines and the AD5.F35-GUCY2C$_{ECD}$-PADRE vaccine in particular.

4.5 Treatment Methods Using AD5.F35-GUCY2C Vaccine

Aspects of the invention include methods of treating individuals who have a cancer/tumor expressing GUCY2C. The treatment is provided systemically. By treating such an individual with a vaccine as set forth herein, an immune response that specifically targets the cancer cells expressing GUCY2C can be induced in the peripheral compartments of the individual's immune system. The vaccines treat primary or metastatic disease including identified metastatic disease as well as any undetected metastasis, such as micrometastasis.

The vaccines provide an adjuvant therapeutic treatment with the ordinary treatment provided upon diagnosis of cancer involving mucosal tissue. As discussed in this application supra one skilled in the art can diagnose a cancer or tumor as expressing GUCY2C. Detection of metastatic disease can be performed using routine methodologies although some minute level of cancer may be undetectable at the time of initial diagnosis of cancer. Typical modes of therapy include surgery, chemotherapy or radiation therapy, or various combinations. Vaccines targeting GUCY2C provide an additional weapon with the advantage of not attacking normal tissue but selectively detecting and eliminating cancer cells originating from immunologically protected compartments expressing GUCY2C.

Accordingly, in some embodiments, an individual is diagnosed as having cancer and the cancer is identified as expressing GUCY2C. A AD5.F35-GUCY2C vaccine expressing soluble GUCY2C linked to a CD4+ helper epitope is administered to the patient alone or as part of a treatment regimen which includes surgery, and/or radiation treatment and/or administration of other anti-cancer agents.

4.6 Prophylactic Methods Using AD5.F35-GUCY2C Vaccine

The vaccines may also be used prophylactically in individuals who are at risk of developing as GUCY2C cancers/tumors. Previous diagnosis with primary disease which has been removed or in remission places the individual at higher risk.

Individuals who are at risk of developing as mucosal tissue cancer may be administered vaccines in order to induce an immune response which will eliminate cancer cells prior to the individual having detectable disease. In some embodiments, such individuals may also be identified for CD4+ helper epitope type. A vaccine administered to the individual which contains the protein or genetic code for the mucosally restricted antigen and one or more CD4+ helper epitopes which are recognized by the individual. However, it may be more practical to utilize a universal CD4+ helper epitope such as PADRE.

4.7 Vaccine Compositions, Formulations, Doses and Regimens

Vaccines according to some embodiments comprise a pharmaceutically acceptable carrier in combination with the active agent which may be, a nucleic acid molecule, a vector comprising a nucleic acid molecule such as a virus, a protein or cells. Pharmaceutical formulations are well known and pharmaceutical compositions comprising such active agents may be routinely formulated by one having ordinary skill in the art. Suitable pharmaceutical carriers are described in Remington's Pharmaceutical Sciences, a standard reference text in this field. The present invention relates to an injectable pharmaceutical composition that comprises a pharmaceutically acceptable carrier and the active agent. The composition is preferably sterile and pyrogen free.

In some embodiments, for example, the active agent can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the immunogen in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon the nature of the active agent and known factors such as the pharmacodynamic characteristics of the particular agent, and its mode and route of administration; age, health, and weight of the recipient: nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

The following examples are provided as exemplary embodiments only and are not intended to limit the scope of the invention.

5.0 *Listeria monocytogenes* Vector-Based Vaccines

Figure 11:
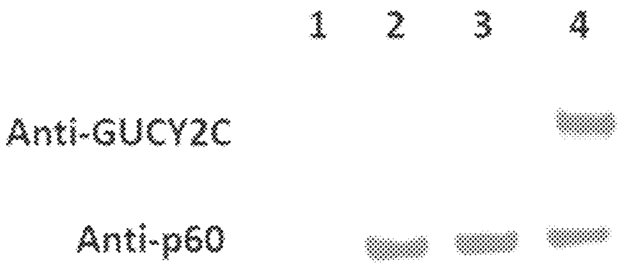
FIG. 11. Recombinant Lm-GUCY2C secretes GUCY2C inside infected J774.A1 macrophages. J774A.1 cells were plated into a 6 well plate and allowed to form monolayers. Macrophages were than infected with $4\times10^7$ CFU of control Lm or Lm-GUCY2C and incubated at 37° C. for one hour. One hour post-infection, media was aspirated, cells washed 1× with PBS and fresh media containing 10 ug/mL gentamicin was added to remove extracellular Lm. Infected macrophages were incubated for 7 additional hours at 37° C. Lysates from infected cells were then prepared and stained using antibodies against GUCY2C or the Lm antigen p60. Lane 1: uninfected J774A.1 cells. Lanes 2: J77A.1 infected with control Lm. Lane 3: J774A.1 infected with Lm-ActA-GUCY2C. Lane 4: J774A.1 infected with Lm-ActA-Syn18x5-GUCY2C.
Figure 12:
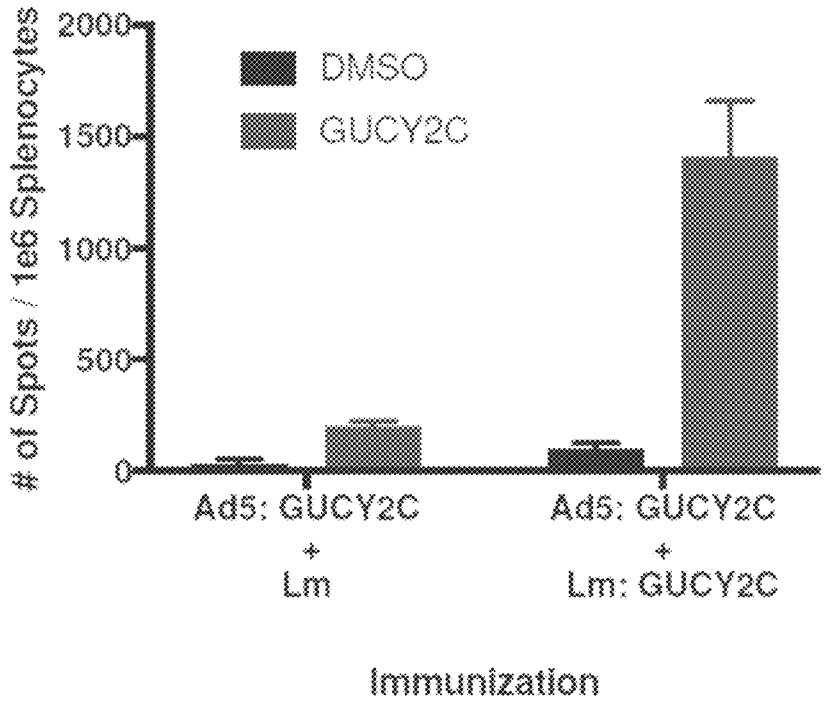
FIG. 12. Recombinant Lm-GUCY2C enhances GUCY2C-specific CD8+ T cell responses following Ad5-GUCY2C-S1 vaccination. BALB/c mice were immunized intramuscularly with 1×108 plaque forming units (PFU) of Ad5-GUCY2C-S1 on day 0. On day 21, mice were immunized with 1×107 colony forming units (CFU) of control Lm or recombinant Lm expressing GUCY2C [Lm-ActA-Syn18x5-GUCY2C ("Lm-GUCY2C")]. On day 27, GUCY2C-specific T cells were quantified by IFN-ELISpot, with DMSO serving as a negative control.
Figure 13:
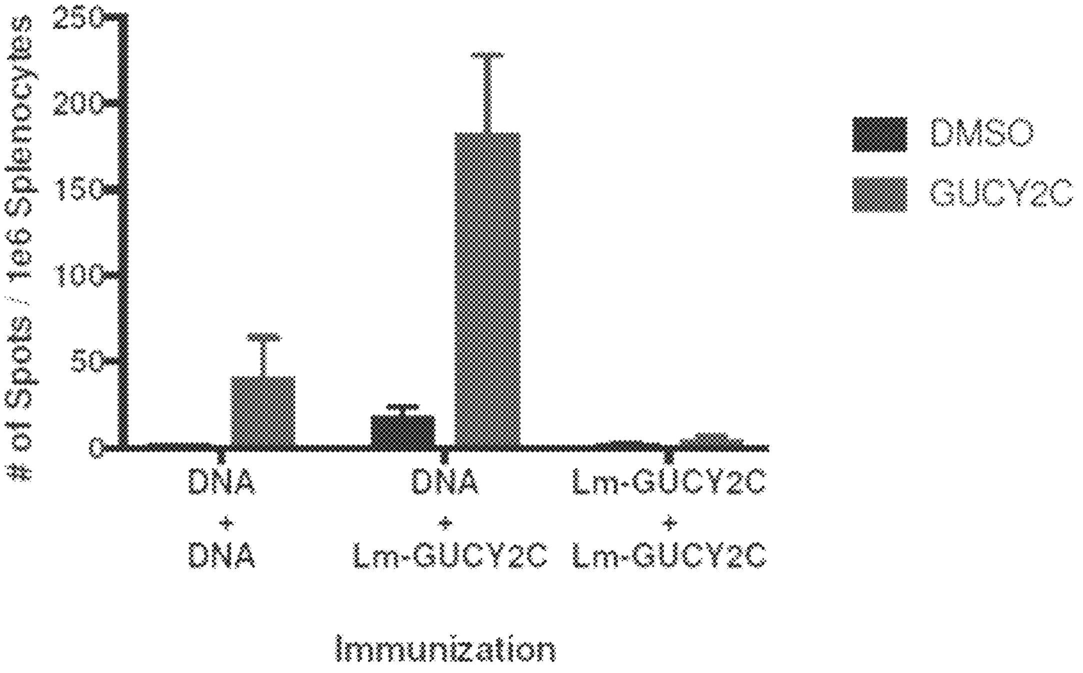
FIG. 13. Recombinant Lm-GUCY2C boosts GUCY2C-specific CD8+ T cell responses following DNA-GUCY2C vaccination. BALB/c mice were primed by DNA or Lm-GUCY2C (Lm-ActA-Syn18x5-GUCY2C) vaccination on day 0 and boosted with DNA or Lm-GUCY2C (Lm-ActA-Syn18x5-GUCY2C) vaccination on day 21. For DNA vaccinations, 50 ug of DNA plasmid encoding GUCY2C protein was injected intramuscularly into each leg and electroporated by 10 pulses (Field strength=100v/cm, pulse length=20 ms, pulse interval=1 s). For Lm vaccinations, 1×107 CFU of Lm-ActA-Syn18x5-GUCY2C was administered intraperitoneally. On day 27, GUCY2C-specific T cells were quantified by IFNγ ELISpot, with DMSO serving as a negative control.

We have developed a recombinant strain of *Listeria monocytogenes* (Lm) expressing GUCY2C (Lm-GUCY2C) and demonstrated its ability to secrete GUCY2C inside infected macrophages (FIG. 11), and boost GUCY2C-specific T cell responses following Ad5 (FIG. 12) or DNA vaccination (FIG. 13). These Lm-GUCY2C-based vaccination regimens are expected to induce robust antitumor efficacy in patients with GUCY2C-expressing cancers, including but not limited to, colorectal, gastric, esophageal, pancreatic, and salivary. Several different variations of "Lm-GUCY2C" are disclosed:

1. Lm-LLO-GUCY2C:
   a. Employs a strong Lm promoter, such as hly [listeriolysin O; (LLO)]; iap [p60; p60], acta [actin-assembly inducing protein; (actA)]; or other PrfA-dependent promoters.
   b. Employs GUCY2C extracellular domain (amino acids ~23 to ~429) fused to the C-terminus of LLO (amino acids ~1 to ~420) to promote cytosolic secretion.
2. Lm-ActA-GUCY2C:
   a. Employs a strong Lm promoter, such as hly [listeriolysin O; (LLO)]; iap [p60; p60], acta [actin-assembly inducing protein; (actA)]; or other PrfA-dependent promoters.
   b. Employs GUCY2C extracellular domain (amino acids ~23 to ~429) fused to the C-terminus of a modified form of ActA known as ActAN100* (described in US Patent US20180030457A1 which is incorporated herein by reference)
3. Lm-ActA-Syn18x5-GUCY2C:
   a. Employs a strong Lm promoter, such as hly [listeriolysin O; (LLO)]; iap [p60; p60], acta [actin-assembly inducing protein; (actA)]; or other PrfA-dependent promoters.
   b. Employs a fusion protein consisting of GUCY2C extracellular domain (amino acids ~23 to ~429) at the C-terminus connected to the Syn18x5 sequence to enhance fusion protein expression (US Patent US20180030457A1) and a modified form of ActA known as ActAN100* at the N-terminus (described in US Patent US20180030457A1) to promote cytosolic secretion.
4. Other variations of Lm-GUCY2C that include a promoter driving expression of GUCY2C proteins/peptides alone or fused to other proteins are also possible and disclosed.

In some embodiments, these may employ various Lm stain "backbones" including, but not limited to, 1. The ΔactA/ΔinLB version of the wild-type 10403S *Listeria monocytogenes* strain (U.S. Pat. Nos. 7,691,393; 7,695,725, which are incorporated herein by reference)
2. The killed but metabolically active (KBMA) version derived from the above ΔactA/ΔinLB version but also containing uvrA and uvrB genetic deletions.
3. The dal dat ΔactA version of the wild-type 10403S *Listeria monocytogenes* strain.
4. The prfA-deficient *Listeria monocytogenes* strain XFL-7.

In some embodiments, the Lm vector comprises any one of several difference GUCY2C inserts such as those described in section 4.2 above. In some preferred embodiments coding sequences for GUCY2C$_{ECD}$ free of universal epitopes linked thereto are inserted into an Lm vector. In some embodiments, GUCY2C inserts such as those described in section 4.2 may be linked to the universal T cell epitopes described in section 4.3. As used herein Lm-GUCY2C, Lm-GUCY2CEC, Lm-GUCY2C-universal T cell epitope and Lm-GUCY2C$_{ECD}$-universal T cell epitope, are used interchangeably to refer to Lm vectors with the genetic insert encoding GUCY2C$_{ECD}$ linked to a universal T cell epitope such that infection with the vaccine results in the GUCY2C$_{ECD}$ linked to a universal T cell epitope fusion protein being expressed and secreted by infected cells. In some embodiments containing a universal T cell epitope, the universal T cell epitope PADRE. Lm-GUCY2C-PADRE and Lm-GUCY2C$_{ECD}$-PADRE are used interchangeably to refer to such embodiments which comprise PADRE.

6.0 Treatment Methods Using AD5.F35-GUCY2C Vaccine, Lm-GUCY2C Vaccine or a Combination of AD5.F35-GUCY2C Vaccine and Lm-GUCY2C Vaccine Aspects of the invention include methods of treating individuals who have a cancer/tumor expressing GUCY2C. The treatment is provided systemically. By treating such an individual with a vaccine as set forth herein, an immune response that specifically targets the cancer cells expressing GUCY2C can be induced in the peripheral compartments of the individual's immune system. The vaccines treat primary or metastatic disease including identified metastatic disease as well as any undetected metastasis, such as micrometastasis.

The vaccines provide an adjuvant therapeutic treatment with the ordinary treatment provided upon diagnosis of cancer involving mucosal tissue. As discussed in this application supra one skilled in the art can diagnose a cancer or tumor as expressing GUCY2C. Detection of metastatic disease can be performed using routine methodologies although some minute level of cancer may be undetectable at the time of initial diagnosis of cancer. Typical modes of therapy include surgery, chemotherapy or radiation therapy, or various combinations. Vaccines targeting GUCY2C provide an additional weapon with the advantage of not attacking normal tissue but selectively detecting and eliminating cancer cells originating from immunologically protected compartments expressing GUCY2C.

In some embodiments, an individual is diagnosed as having cancer and the cancer is identified as expressing GUCY2C. A AD5.F35-GUCY2C vaccine expressing soluble GUCY2C linked to a CD4+ helper epitope is administered to the patient alone or as part of a treatment regimen which includes surgery, and/or radiation treatment and/or administration of other anti-cancer agents.

In some embodiments, an individual is diagnosed as having cancer and the cancer is identified as expressing GUCY2C. An Lm-GUCY2C vaccine expressing soluble GUCY2C is administered to the patient alone or as part of a treatment regimen which includes surgery, and/or radiation treatment and/or administration of other anti-cancer agents.

In some embodiments, an individual is diagnosed as having cancer and the cancer is identified as expressing GUCY2C. A prime-boost method is undertaken using both an adenovirus vector-based anti-GUCY2C vaccine and an Lm vector-based anti-GUCY2C vaccine sequentially in combination. In some embodiments, the individual is administered an adenovirus vector that expresses a soluble from of GUCY2C first and subsequently an Lm vector-based anti-GUCY2C vaccine. In some such embodiments, the individual is preferably administered an AD5.F35-GUCY2C vaccine first and subsequently an Lm GUCY2C vaccine but the vaccine may be delivered in reverse order. The shortest interval between the first vaccination and the second is about 2-4 weeks. The preferred interval is about 4-6 weeks. The interval may be between up to 12 months. The vaccine combination therapy may be administered in combination with surgery, and/or radiation treatment and/or administration of other anti-cancer agents.

7.0 Prophylactic Methods Using AD5.F35-GUCY2C Vaccine, Lm-GUCY2C Vaccine or a Combination of AD5.F35-GUCY2C Vaccine and Lm-GUCY2C Vaccine The vaccines may also be used prophylactically in individuals who are at risk of developing as GUCY2C cancers/tumors. Previous diagnosis with primary disease which has been removed or in remission places the individual at higher risk.

Individuals who are at risk of developing cancer that express GUCY2C may be administered vaccines in order to induce an immune response which will eliminate cancer cells prior to the individual having detectable disease.

8.0 Vaccine Compositions, Formulations, Doses and Regimens

Vaccines according to some embodiments comprise a pharmaceutically acceptable carrier in combination with the active agent which may be an adenovirus vector or an Lm vector. Pharmaceutical formulations are well known and pharmaceutical compositions comprising such active agents may be routinely formulated by one having ordinary skill in the art. Suitable pharmaceutical carriers are described in Remington's Pharmaceutical Sciences, a standard reference text in this field. The present invention relates to an injectable pharmaceutical composition that comprises a pharmaceutically acceptable carrier and the active agent. The composition is preferably sterile and pyrogen free.

In some embodiments, for example, the active agent can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the immunizing agent in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon the nature of the active agent and known factors such as the pharmacodynamic characteristics of the particular agent, and its mode and route of administration; age, health, and weight of the recipient: nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

The following examples are provided as exemplary embodiments only and are not intended to limit the scope of the invention.

The following examples are provided as exemplary embodiments only and are not intended to limit the scope of the invention.

EXAMPLES

Example 1

Figure 3:
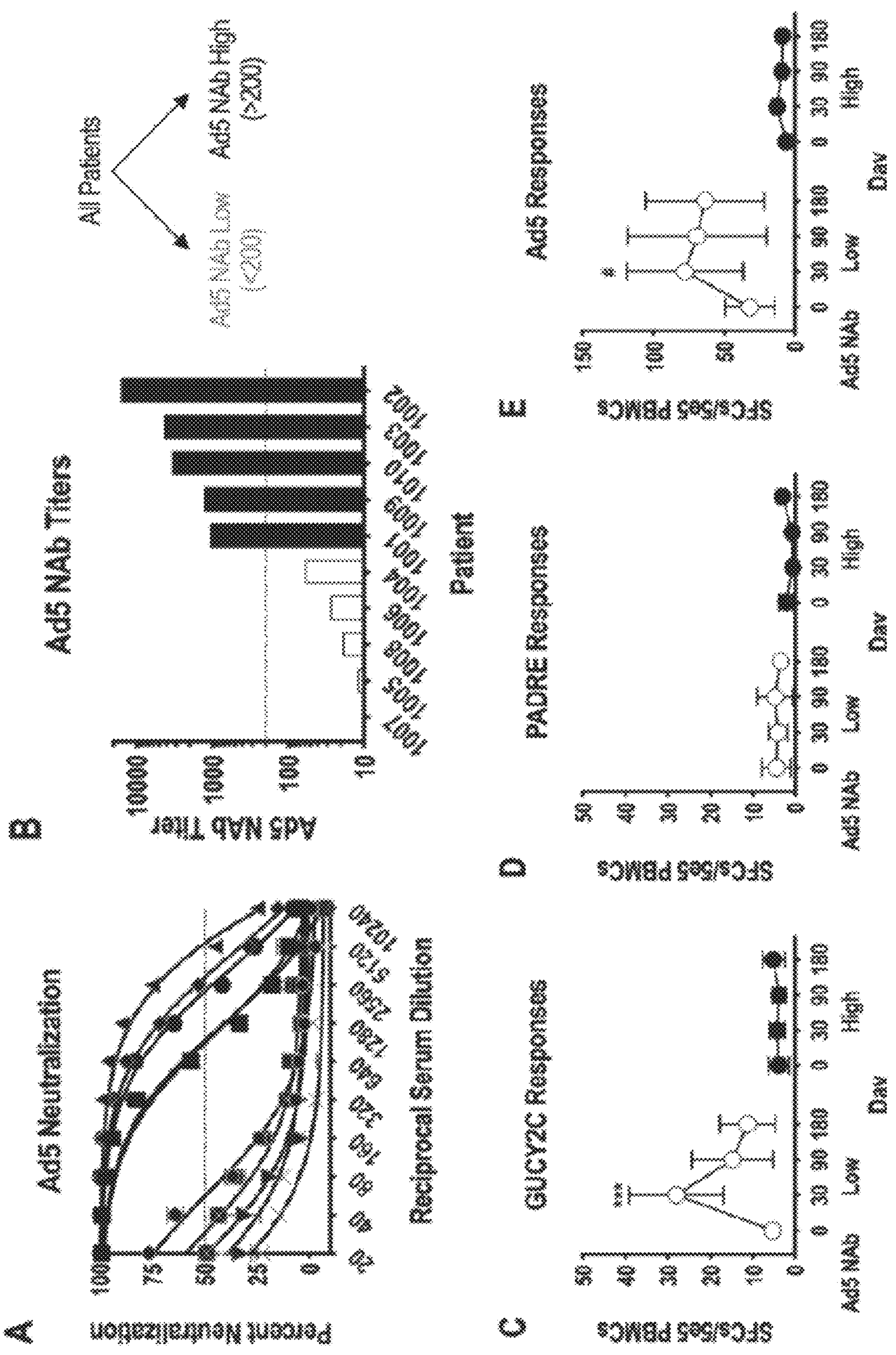
FIG. 3 panels A-E refer to Ad5 neutralizing Abs limit GUCY2C responses in humans. Patient serum samples collected prior to vaccination (day 0) where analyzed for Ad5 neutralizing antibodies (NAbs) employing an in vitro Ad5-GFP reporter virus inhibition assay (A). The Ad5 NAb titer was calculated as the dilution of serum that produced 50% inhibition of GFP reporter expression. (B) Patients were rank-ordered by Ad5 NAb titers and patients with titers <200 where designated as Ad5 NAb Low, while those with titers >200 where designated Ab5 NAb High (dotted line indicates a titer of 200). (C-E) Antigen-specific responses to GUCY2C (C), PADRE (D), and Ad5 (E) were compared in Ad5 NAb Low and High patient populations by iFNγ-ELISpot.
Figure 4:
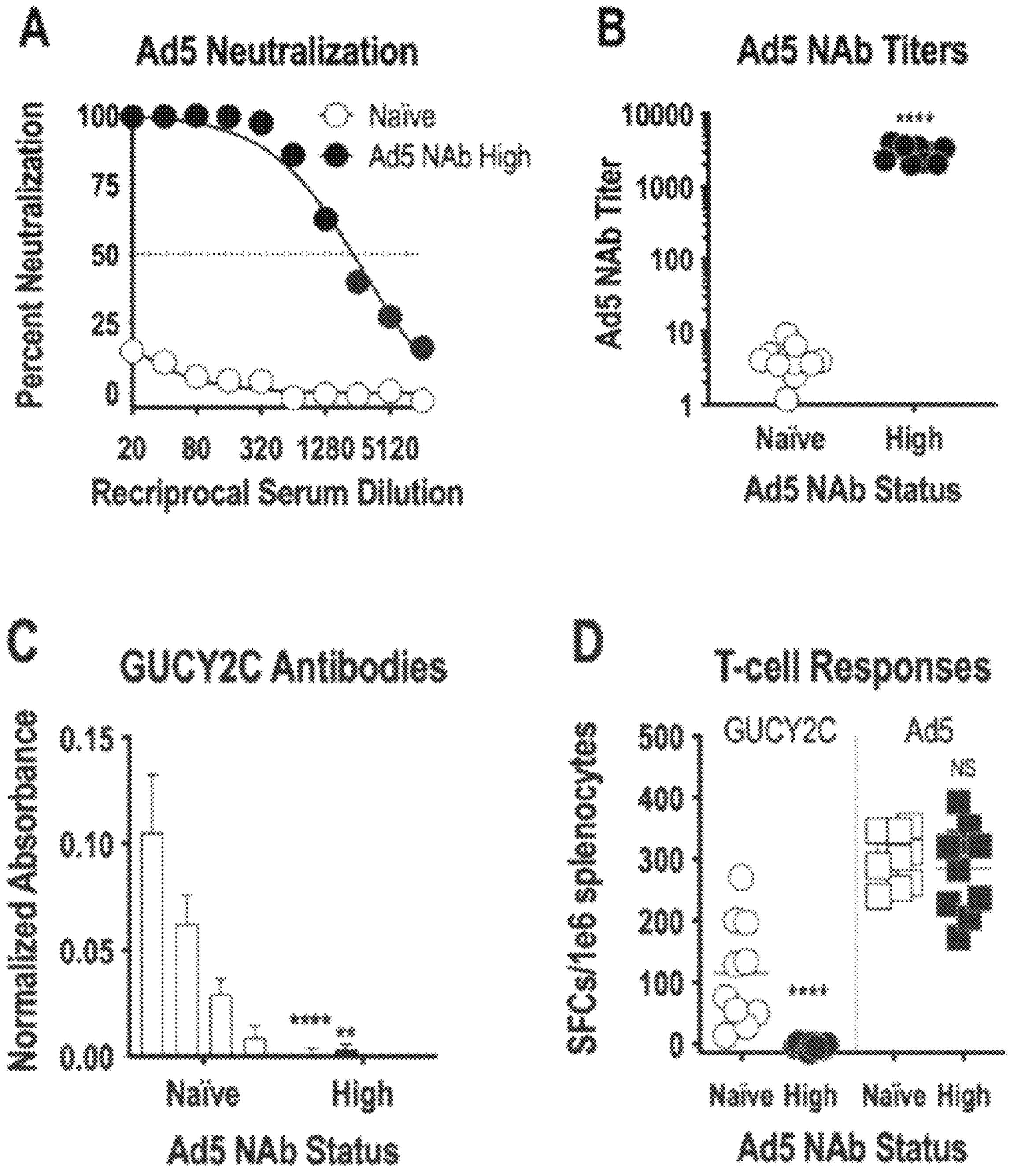
FIG. 4 panels A-D refer to Ad5 neutralizing antibodies limit GUCY2C responses in mice. BALB/c mice were naive or preconditioned by immunizing 2 times with $10^8$ IFU control Ad5 to induce High Ad5 neutralizing antibody (NAb) titers (n=10 mice/group). (A and B) two weeks after preconditioning, serum was collected and Ad5 NAb titers (B) were determined using an in vitro assay to quantify inhibition of A549 cell infection by an Ad5-GFP reporter virus in the presence of serum titrations (A). The Ad5 NAb titer was calculated as the dilution of serum that produced 50% inhibition of GFP reporter expression. (C and D) mice were then immunized with 108 IFU of Ad5-mGUCY2C-S1 expressing mouse GUCY2C fused to the $CD4^+$ T-helper cell epitope S1. GUCY2C-specific antibody (C) and $CD8^+$ T-cell responses (D) were quantified two weeks later by ELISA and IFNγ-ELISpot, respectively. NS=not significant, * P<0.05, * P<0.001, ** P<0.0001 Two-way ANOVA.

Phase 1 clinical trial patients receiving Ad5-GUCY2C-PADRE, had Ad5 neutralizing antibody (NAb) titers ranged from <10 to >10,000. An obvious pattern emerged in which half of the patients had titers well below 200 (Ad5 NAb Low) and the other half had titers well above 200 (Ad5 NAb High). Separating patients into Ad5 NAb Low and High cohorts revealed a relationship between Ad5 NAb titer and GUCY2C-specific T-cell responses in which responses were significantly greater in Ad5 NAb Low patients. (FIG. 3). Together, these data are in agreement with our animal data (FIG. 4) demonstrating that pre-existing Ad5 NAb eliminates efficacy of Ad5-GUCY2C-PADRE, despite the administration of high doses, and in contrast to other vaccines (Priddy, F. H., et al. (2008). Clin Infect Dis 46(11): 1769-1781). Additional results are shown at Table 1:

TABLE 1

Ad5-hGCC-PADRE is Limited by Ad5 nAbs

| Patient | Ad5 nAb Titer | Ad5 nAb Status | GCC-specific T-cell Response at Day 30 (SFCs/5 × $10^5$ PBMCs) | Significance |
|---|---|---|---|---|
| 1007* | 9.649 | Low | 43.25 | P < 0.001 |
| 1005 | 12.04 | Low | 10.50 | P = NS |
| 1008 | 18.76 | Low | 63.83 | P < 0.001 |
| 1006 | 27.21 | Low | 6.00 | P = NS |
| 1004 | 59.51 | Low | 19.50 | P < 0.001 |
| 1001 | 1074 | High | 0.00 | P = NS |
| 1009 | 1309 | High | 2.17 | P = NS |
| 1010 | 3355 | High | 8.17 | P < 0.001 |
| 1003 | 4379 | High | 2.00 | P = NS |
| 1002 | 15951 | High | 8.67 | P = NS |

*Only patient that produced a GCC-specific antibody response

Figure 5:
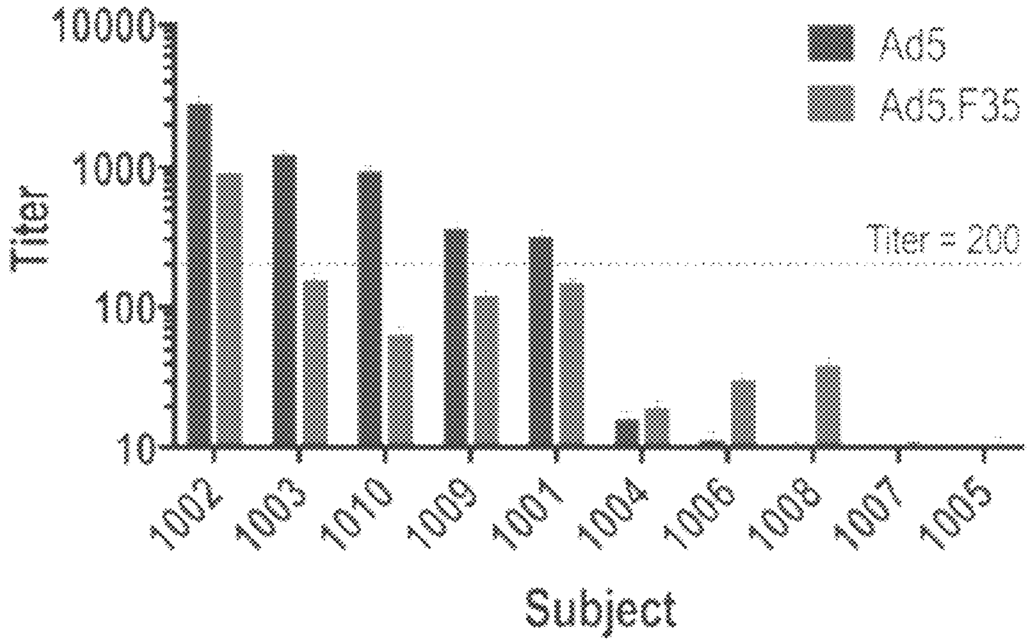
FIG. 5 refers to Ad5 and Ad5.F35 NAb Titers in Phase 1 Subjects. Pre-vaccination serum samples from the Phase 1 study subjects were tested for Ad5 or Ad5.F35 neutralizing antibody (NAb) titers using an Ad5-GFP or Ad5.F35-GFP reporter virus inhibition bioassay. Titers were calculated as the dilution of serum producing 50% inhibition by non-linear regression. Values indicate the computed titers and standard deviation for each subject. The dashed line indicates a titer of 200, the standard threshold for "high" neutralizing titers. All subjects possessed less neutralizing immunity for Ad5.F35 than Ad5. Importantly, while 5/10 subjects possessed "high" Ad5 NAb titers, only 1 subject possessed "high" Ad5.F35 NAb titers.

Ad5 NAbs are common in most human populations, including ~40% in the US (Nwanegbo, E., et al. (2004) Clin Diagn Lab Immunol 11(2): 351-357; Barouch, D. H., et al. (2011) Vaccine 29(32): 5203-5209), reducing the immunogenicity of Ad5-based vaccines (Priddy, F. H., et al. (2008). Clin Infect Dis 46(11): 1769-1781). Importantly, most naturally-occurring Ad5 NAbs target the fiber molecule on the surface of Ad5 (Cheng, C., et al. (2010) J Virol 84(1): 630-638). In contrast to Ad5, the seroprevalence of Ad35-specific antibodies in most countries is very low (<10%; Nwanegbo, E., et al. (2004) Clin Diagn Lab Immunol 11(2): 351-357.; Barouch, D. H., et al. (2011) Vaccine 29(32): 5203-5209). Together, these observations suggest that replacement of the fiber molecule in Ad5 with the fiber molecule from Ad35 will produce a chimeric Ad5 viral vector (known as Ad5.F35) that is not affected by naturally-occurring Ad5 immunity. Indeed, while 50% of subjects in the Ad5-GUCY2C-PADRE Phase 1 study possessed high Ad5 NAbs (titer >200), only 1/10 subjects possess high Ad5.F35 NAbs (FIG. 5). Thus, Ad5.F35-GUCY2C-PADRE is expected to overcome Ad5-specific preexisting immune which was not achieved by dose escalation as predicted by the published literature (Priddy, F. H., et al. (2008). Clin Infect Dis 46(11): 1769-1781).

Example 2

To produce Ad5.F35-hGCC-PADRE, an hGCC-PADRE coding sequence was synthesized to produce a mammalian codon-optimized sequence set forth at SEQ ID NO: 3 to increase efficiency of hGCC-PADRE mRNA translation into protein. This construct was subcloned into an Ad5.F35 vector to produce Ad5.F35-hGCC-PADRE.

Overall, the structure of Ad5.F35-hGCC-PADRE is identical to wild type Ad5 (GenBank: AY339865.1), with three exceptions. First, the hGCC-PADRE expression cassette replaced the E1A and E1B regions of Ad5 (nucleotides 455-3512), rendering Ad5.F35-hGCC-PADRE replication incompetent. Second, Ad5.F35-hGCC-PADRE possesses a large deletion of the E3 region (nucleotides 28586-30464). The E3 region possess several proteins with immunosuppressive functions. All of these E3 proteins are deleted in Ad5.F35-hGCC-PADRE.

Finally, the Ad5 fiber has been replaced with the Ad35 fiber, to minimize neutralization of the vector by pre-existing antibodies to Ad5 in patients.

Ad5.F35-hGCC-PADRE DNA Construct Generation

The hGCC-PADRE coding sequence was synthesized to possess a Kozak sequence (GCCGCCACC) immediately 5' of the initiating ATG and two stop codons immediately after the PADRE sequence. The hGCC-PADRE construct was subclones into the pShuttle vector and then recombined into the Ad5.F35 vector. The Ad5.F35 possesses the human Ad5 sequences encoding all elements required to produce replication-incompetent adenovirus including left and right inverted terminal repeats (ITRs), encapsulation signal for packaging, E2 and E4 regions and late genes. The plasmid lacks the E1 and E3 proteins and replaces the fiber with Ad35 fiber.

Preparation, Structure, and Composition of the Ad5.F35-hGCC-PADRE

A master virus bank of the adenoviral vector Ad5.F35-hGCC-PADRE was produced under GMP conditions in the Vector Production Facility (VPF) of the Center for Cell and Gene Therapy (CAGT), Baylor College of Medicine in Houston, Texas.

Recombinant adenoviral vector was produced in HEK293 cells, which possess the E1 genes needed for viral replication. Viable Ad5.F35-hGCC-PADRE virus was formed and collected. The virus underwent two rounds of plaque purification in HEK293 cells. Individual plaques were tested for the presence of hGCC-PADRE DNA, sequenced for hGCC-PADRE cassette accuracy and tested for their ability to produce hGCC-PADRE protein upon infecting cells in vitro. Plaque-purified vector was then expanded in HEK293 cells in tissue culture flask and further amplified used 10-layer cell culture chambers (cell factories). After large-scale amplification, Ad5.F35-hGCC-PADRE was purified by banding in CsCl. The Ad5.F35-hGCC-PADRE Master Virus Bank (MVB) was fully sequenced. A portion of the MVB was vialed for subject administration as part of this trial.

Example 3

Vaccination Protocol

The Ad5.F35-hGCC-PADRE vaccine to be used is composed of a recombinant, replication-deficient E1/E3-deleted Ad5.F35 virus possessing a GCC-PADRE expression cassette. This vaccine vector employs recombinant human type 5 adenovirus (rAd5), The rAd5 possesses deletions of the early E1 and E3 regions of the vector, enabling insertion of the GCC-PADRE cassette. E1/E3 deletion renders the virus replication-incompetent increasing safety associated with its clinical use.

Ad5.F35-hGCC-PADRE: $10^{11}$, $10^{12}$, or $5\times10^{12}$ viral particles formulated in TG buffer (20 mM Tris-HCl, pH 8.0, 25 mM NaCl, 2.5% glycerol) is administered intramuscularly to human patients with selected solid tumors (colorectal, pancreatic, gastric, or esophageal) who are at risk of relapse post definitive surgery and standard adjuvant therapy. Dosages are administered three (3) times. The dosage interval is four (4) weeks apart.

Subjects cellular (T-cell) response to Ad5.F35-hGCC-PADRE and humoral immunologic response to GCC are evaluated at 5, 9 and 14 weeks following the first vaccination. The effect of preexisting neutralizing antibody to Ad5 is reduced from that previously observed.

Example 4

A Phase 2A, Dose-Finding Study of Ad5.F35-hGCC-PADRE Vaccine in Adults with Gastrointestinal Adenocarcinomas at Risk of Relapse Post Definitive Surgery and Standard Therapy This is an open-label, dose-finding, Phase 2A study of Ad5.F35-hGCC-PADRE as a vaccine for gastrointestinal (GI) malignancies (pancreatic, colorectal, esophageal, and gastric adenocarcinomas) who have received surgical resection and standard adjuvant therapy. Patients will be given multiple administrations of Ad5.F35-hGCC-PADRE intramuscularly at 1 of 3 dose levels. Treatment-related toxicity and development of immune responses to GCC will be evaluated at Weeks 5, 9, and 13 after the initial vaccination (Week 1). Primary safety endpoints will examine adverse events (AEs), injection-site reactions and clinically-significant changes in safety laboratory tests. Primary efficacy endpoints include the development of GCC-specific T-cell responses at different dose levels (1011, 1012, and 5×1012 virus particles or vp).

Objectives

The primary objectives of the study are as follows.

1) Evaluate the safety and tolerability of sequential Ad5.F35-hGCC-PADRE vaccine administration, delivered intramuscularly (IM) at three dose levels (1011, 1012, and 5×1012 vp) four weeks apart in subjects with high-risk colorectal, pancreatic, gastric, or esophageal adenocarcinomas with no evidence of disease after surgery and standard therapy.
2) Evaluate the cellular (T-cell) responses to Ad5.F35-hGCC-PADRE at three different dose levels (1011, 1012, and 5×1012 vp) administered intramuscularly (IM) as three sequential doses four weeks apart in subjects with high-risk colorectal, pancreatic, gastric, or esophageal adenocarcinomas with no evidence of disease after surgery and standard therapy.

In observed, objectives include the following:

1) Evaluate the humoral (antibody) responses to Ad5.F35-hGCC-PADRE at three different dose levels (1011, 1012, and 5×1012 vp) administered IM as three sequential doses four weeks apart in subjects with high-risk colorectal, pancreatic, gastric, or esophageal adenocarcinomas with no evidence of disease after surgery and standard therapy
2) Evaluate the association of neutralizing antibodies to Ad5 with immunologic response
3) Evaluate the correlation of the immune response to the GCC protein expression in tumors to assess immune tolerance
4) Evaluate disease-free survival (DFS)
5) Evaluate overall survival (OS), where feasible Population The target final sample size is 72 subjects with evaluable response data. A maximum of 81 subjects with 01 adenocarcinomas satisfying all eligibility criteria will be enrolled. We expect to enroll approximately three patients per month. A futility analysis will be performed in each arm after 15 patients have completed treatment with possible discontinuation of arms at that point. Thus, the minimum sample size is 45.

Protocol

Ad5.F35-hGCC-PADRE: 1011, 1012, or 5×1012 viral particles formulated in TG buffer (20 mM Tris-HCl, pH 8.0, 25 mM NaCl, 2.5% glycerol) and administered intramuscularly.

A minimum of 45 and a maximum of 81 subjects will be enrolled in this study. Subjects will be randomized to one of three treatment arms with stratification according to the tumor type and surgical resection margin (RO or negative resection margin Vs. R1 or positive resection margin). Treatment Arm A will receive three 1011 vp vaccine doses four weeks apart. Treatment Arm B will receive three 1012 vp vaccine doses four weeks apart. Treatment Arm C will receive three 5×1012 vp vaccine doses four weeks apart. Subjects will be randomized to each treatment arm and will initiate treatment concurrently with continuous monitoring of adverse events.

Following completion of the 13-week study evaluation for immune response and safety, subjects will be followed-up by phone or optional clinic visit for subsequent cancer-related therapies, DFS rate for at least 24 months of follow-up, recurrence or death whichever occurs first.

The duration of the treatment cycles (i.e., three doses) will be nine weeks. Subjects will be considered in the treatment period until four weeks after their final study dose, after which they will be in follow-up until death, early discontinuation, or completion of follow-up. Subjects will be followed for the duration of the study until all subjects have reached at least 24 months of follow-up or death. At the conclusion of the study, all remaining subjects will be offered enrollment in a long-term follow-up protocol.

INTRODUCTION

Background Information

The study is open to subjects with solid tumors of the gastrointestinal (GI) tract who are at high risk of recurrence post definitive surgery and/or standard therapy. The subject population includes individuals with colorectal, pancreatic, gastric, or esophageal adenocarcinomas who meet the study eligibility criteria.

Epidemiology and Current Treatment of Pancreatic, Colorectal, Esophageal, and Gastric Cancer Pancreatic, colorectal, gastric, and esophageal cancer each represent an ongoing major burden of cancer in the United States, despite improvement in detection and treatment. In each case, significant numbers of patients undergo surgical resection and standard therapy with an attempt at cure, but only a fraction (variable by disease histology, stage, and other factors) remain in remission. Adjuvant therapy in the form of chemotherapy and/or radiation therapy in these cases improves overall clinical outcome; however, especially for patients with high-risk features, there is significant room for further improvement.

GI malignancies were responsible for 26% of cancer-related deaths in the United States in 2016. Colorectal carcinomas were the fourth most common and second most lethal cancer whereas pancreatic, esophageal and gastric cancers had the third-, tenth- and sixteenth-highest estimated cancer-related death rate in the US in 2016. The 5-year relative survival rate for GI malignancies varies with disease stage. In general, pancreatic adenocarcinomas have the worst five-year survival rate (7%) for all stages while it is 2% for Stage 4 disease (distant metastasis), 11% for regionally spread disease and 27% for localized disease. The majority of exocrine pancreatic adenocarcinomas (>80%) are not diagnosed until the development of locoregional or distant metastasis when they are no longer amenable to surgical resection and have an estimated median survival of 3 to 6 months.[2] Pancreatic adenocarcinomas that are surgically resected have an estimated median survival of 18 months, whereas only 20% of patients survive at 5 years.

For patients with localized pancreatic, colorectal, gastric, and esophageal cancer who are nevertheless considered high risk for relapse, the mainstay of therapy could involve surgery, chemotherapy, and radiation. Adjunct therapy with monoclonal antibodies is also used in colorectal and esophageal cancers. Having established utility in patients with melanoma, prostate, and non-small cell lung cancers, immune therapies are increasingly being investigated in difference settings as a means of reducing risk of relapse.

This study aims to evaluate a novel vaccine immunotherapy delivered intramuscularly (IM) sequentially at three dose levels to identify the dose that is well tolerated and most suited to induce cellular immune response. The ultimate therapeutic goal of this vaccine is to reduce the risk of relapse in subjects with 01 adenocarcinoma, at a later stage of clinical development.

Pancreatic Adenocarcinoma and Available Therapy

Of the estimated 46,000 Americans diagnosed with pancreatic adenocarcinoma in 2014.5 approximately 20% are considered resectable. After recovery from surgery, the primary modality for adjuvant therapy is chemotherapy, such as gemcitabine with capecitabine or 5-fluorouracil with irinotecan and oxaliplatin (modified FOLFIRNOX)8. It is well established that chemotherapy is superior to best supportive care, with hazard ratios of about 0.60 and reduction of mortality by about one-third.9 Compared to a 21.4% disease-free survival rate at 3-years in the gemcitabine alone group, the modified FOLFIRINOX regimen improved 3-year disease-free survival to 39.7% while also improving overall survival rate to 63.4% compared to 48.6% in the gemcitabine alone group8. Regardless of surgery and adjuvant therapy, however, at least 80% of patients relapse and eventually die. Survival is related to pathological features, pre-operative functional status, operative results, and adjuvant therapy. According to the American Cancer Society, for all stages of pancreatic cancer combined, the one-year relative survival rate is 20%, with a five-year survival rate of 6%. If a surgical resection can be performed, the average survival rate is 18-20 months. The overall five-year survival rate is about 10% but can reach 20-25% in cases when the tumor is completely removed and when the cancer has not spread to lymph nodes.

Colorectal Cancer and Available Therapy

Of the estimated 132,000 Americans diagnosed with colorectal cancer (CRC) annually, approximately two-thirds will receive surgical resection. Five-year survival rates depend on the nature and stage of cancer, but is in the range of 25-70%.

When CRC is diagnosed at an early stage, in many cases surgery alone can be curative. In later stages, a cure is still considered possible with surgery and often chemotherapy in the form of fluorouracil, fluoropyrimidine, capecitabine, or oxaliplatin are used as adjuvant therapy. Two studies found 10-15% three-year survival gain when receiving post-surgery adjuvant therapy, while other studies have also found some beneficial gains from adjuvant treatment.

Recent improvement in both surgical and adjuvant treatment as well as early diagnosis has increased three-year DFS in patients who receive surgical resection. Targeted therapies in the form of monoclonal antibodies against VEGF and EGFR are also available for patients with advanced disease4, but cure rates remain low with high relapse rates. Two anti-PD-1 checkpoint immunotherapies—nivolumab (Opdivo®) and pembrolizumab (Keytruda®)—have also been approved for colorectal cancer patients with advanced, relapsed tumors that are characterized by high microsatellite instability (MSI-hi), but the overall response rate with these therapies remains low.

Gastric Cancer and Available Therapy

An estimated 25,000 Americans are diagnosed with gastric cancer annually. The majority of patients with early-stage cancer have surgically-resectable disease—in localized distal gastric cancer, more than 50% of patients can be cured. However, early-stage disease accounts for only 10-20% of all cases diagnosed in the United States. The OS rate at 5 years ranges from almost no survival for patients with disseminated disease to approximately 50% survival for patients with localized distal gastric cancers with resectable regional disease. Although the clinical benefits of adjuvant therapy have been debated, recent studies are indicating potential benefits. In one study, adjuvant-treated patients received capecitabine and oxaliplatin, with a hazard ratio of 0.58 and had an improved five-year DFS. Another study using adjuvant fluoropyrimidine found the treated group to exhibit 10% increased survival rates compared to surgery-only within the first year. Current treatment with or without adjuvant therapy leads to an average five-year survival rate of 10-15% in patients with proximal gastric cancer and more than 50% cancer relapse among resected patients, suggesting inadequate effectiveness of current therapeutic regimens. Additionally, pembrolizumab (Keytruda®), an anti-PD-1 checkpoint immunotherapy, was recently approved for patients with advanced, PD-L1-positive stomach cancer, though response rates are modest.

Esophageal Cancer and Available Therapy

According to the National Cancer Institute (Cancer.gov), an estimated 16,940 persons will be diagnosed with and 15,690 persons will die of cancer of esophagus in 2017. Approximately, one-half have resectable tumors. On average, 18.8% of patients survive five years after diagnosis, however 5-year survival rate precipitously declines to 4.6% in patients with distant disease. While esophagectomy remains the cornerstone treatment of clinically-localized esophageal carcinoma, the nature of the disease attributes to the failure of surgery alone. In squamous cell carcinomas of the esophagus, neoadjuvant cisplatin was not found to offer an improvement in survival, while neoadjuvant cisplatin and fluorouracil increased 5-year DFS by 10%. In contrast, neoadjuvant chemotherapy (carboplatin & paclitaxel) and radiotherapy in adenocarcinomas of the esophagus had a median OS of 49.4 months, compared with 24 months in the surgery-alone group. Other studies have also found beneficial effects of neoadjuvant chemotherapy with epirubicin, 5-fluorouracil and/or cisplatin in patients with adenocarcinoma of the stomach or gastroesophageal junction. In addition, antibody therapies have emerged in the treatment of esophageal cancer, targeting HER2 in the small number of esophageal cancers overexpressing HER2 and targeting the VEGF pathway to inhibit angiogenesis4. A recent meta-analysis of 13 randomized controlled trials of neoadjuvant chemoradiotherapy compared to surgery alone, showed a pooled hazards ratio of 0.78; corresponding to an absolute survival benefit at 2 years of 8.7% and a number needed to treat of 11. The effects of neoadjuvant therapy in esophageal cancer are generally beneficial compared to best supportive care, however the relapse remains high and many patients eventually die. Like gastric cancer, pembrolizumab (Keytruda®), an anti-PD-1 checkpoint immunotherapy, was recently approved for patients with PD-L1-positive cancer of the gastroesophageal junction, though response rates are modest. Given the incidence rate and prognosis of this disease, effective adjuvants with minimal side effects are needed to improve disease outcome.

Rationale for the Proposed Study

Guanylyl Cyclase C (GCC) as a Tumor-Associated Antigen in Colon Cancer

Guanylyl cyclase C (GCC or GUCY2C), one of a family of homologous proteins synthesizing cyclic GMP (cGMP), is specifically expressed by intestinal epithelial cells. GCC is the receptor for the paracrine hormones guanylin and uroguanylin and the diarrheagenic bacterial heat-stable enterotoxins (STs), whose interaction with the extracellular domain activates the cytoplasmic catalytic domain, inducing cGMP accumulation. While catalytic domains across family members share ~50% homology, the extracellular domain of GCC exhibits <20% homology, creating an antigenically-unique structure. GCC has been detected in >500 samples of normal intestine, but not in >1,000 extra-gastrointestinal tissues. Moreover, in intestinal epithelial cells, GCC is specifically localized in apical brush border membranes, "outside" the mucosal barrier. This anatomical and functional compartmentalization suggests that, normally, GCC is mucosally-restricted, confirmed by radioligand imaging and biodistribution and immunological studies. Of significance, GCC protein (>200 specimens) and/or mRNA (>900 specimens) were detected in nearly all primary and metastatic human colorectal tumors, with uniform expression by tumor cells, regardless of anatomical location or grade, but not in any extra-GI tumors (>200). Further, GCC is over-expressed by >80% of colorectal tumors. Stringency of expression by intestinal cells and universal over-expression by metastases is underscored by the utility of GCC as a marker for staging pN0 patients.

GCC in Pancreatic, Gastric and Esophageal Cancers

GCC is normally expressed in intestinal epithelial cells and expression is retained during neoplastic transformation of the colorectum both in the regional and metastatic setting. In addition, GCC is found to be expressed in approximately ~60% of pancreatic, gastric, and esophageal cancers. Disruption of epithelial tight junctions, cell polarity and apical localization of GCC makes it a desired target for systemic agents in tumor tissues while leaving normal tissues unaffected.

The Ad5.F35-hGCC-PADRE Vaccine

Preclinical Studies Using Ad5-hGCC-PADRE

In preclinical studies, we have demonstrated that Ad5 vector vaccines incorporating mouse GCC produce GCC-specific immune responses (antibodies and cytotoxic T cells) in mice. These responses are durable, lasting months after immunization. In addition, GCC-specific cytotoxic T cells induced by the vaccine are capable of killing GCC-expressing CRC cells in vitro. Mice with GCC-expressing metastatic colorectal tumors growing in lungs or liver are protected by GCC vaccination: GCC vaccination reduces (or eliminates) the number of detectable metastatic tumors and greatly improves animal survival. Importantly, these immune responses selectively target metastatic CRC, but do not target normal intestinal tissue expressing GCC, nor do they cause intestinal pathology. Thus, GCC-targeted vaccination induces GCC-specific immune responses that can prevent/treat metastatic CRC in murine models, but do so without causing adverse effects. This targeted treatment is anticipated to be highly advantageous clinically compared to established cancer therapies, which have poor efficacy and cause considerable off-target toxicities.

Ad5-hGCC-PADRE Vaccine Clinical Data to Date

The Ad5-hGCC-PADRE vaccine was initially evaluated in humans in an open-label, single arm, single dose feasibility study to determine the safety and immunogenicity of Ad5-hGCC-PADRE in early-stage colorectal cancer patients (ClinicalTrials.gov NCT1972737). Subjects received a single intramuscular injection of 10 particles of Ad5-hGCC-PADRE.

Safety Data

Subjects in the study were assessed for acute events in the clinic every 10 minutes for 30 minutes after injection and by telephone on Days 3 and 8 following vaccination. Patients also returned to the clinic 30, 90, and 180 days after vaccination for safety assessment. Adverse events were graded according to the CTCAE version 5.0. Among the ten subjects who received Ad5-hGCC-PADRE, 10 (100%) experienced an AE. The most frequently reported vaccine-related AEs were chills/rigor (20%), injection-site pain/swelling (20%), dizziness (10%), diaphoresis (10%), aches (10%) and fever (10%). There were no serious adverse events (SAEs) and no subject died during the study.

All AEs were Grade 1 and no Grade 3/4 toxicities occurred at any time during the 6-month follow-up period after vaccination. Moreover, laboratory assessments performed on Days 30, 90, and 180, including CBC with differential, comprehensive chemistry panel, and antinuclear antibody (ANA) titers, revealed no clinically-relevant changes. Based upon reported clinical experience with similar therapies, mild Grade 1/2 toxicities such as injection-site pain and fever are anticipated following a viral vector immunization and were observed in several patients. Importantly, no adverse events related to toxicity in GCC-expressing tissues were observed. GCC is a self-protein expressed on the luminal surface of small and large intestinal epithelia, as well as anorexigenic hypothalamic neurons. However, consistent with mechanisms controlling immune compartmentalization and preclinical studies of GCC vaccination there was no evidence of Ad5-hGCC-PADRE-induced autoimmunity in GCC-expressing intestinal or brain tissue.

Immunogenicity Data

In preclinical studies, immunization with Ad5-hGCC-PADRE induced time- and dose-dependent GCC-specific T-cell and B-cell responses and antitumor immunity mediated by $CD8^+$ T cells. In the clinical study, GCC-specific immune responses were quantified after Ad5-hGCC-PADRE administration by ELISA and IFNγ-ELISpot to quantify antibody and T-cell responses, respectively. T-cell responses to PADRE and Ad5 also were quantified by IFNγ-ELISpot. Immune responses in the patients typically followed one of four patterns:

1) no pre-vaccine antibody responses to GCC or T-cell immunity to GCC, PADRE, or Ad5 and Ad5-hGCC-PADRE vaccination induced no responses targeted toward any of the antigens
2) no pre-vaccination responses, while vaccination induced Ad5-specific T-cell responses, but not GCC-specific or PADRE-specific responses
3) Ad5-hGCC-PADRE vaccination induced GCC-specific T-cell responses. No PADRE-specific T-cell response or GCC-specific antibody response, similar to animal studies in which GCC-specific antibody responses require responses to exogenous $CD4^+$ "helper" T-cell epitopes, reflecting GCC-specific $CD4^+$ T-cell tolerance.
4) Vaccine-induced responses by all three arms of adaptive immunity: PADRE-specific $CD4^+$ T-cell response, GCC-specific antibody response, and GCC-specific $CD8^+$ T-cell response Ad5 nAbs Limit Ad5-hGCC-PADRE Immunogenicity Ad5 is a natural human pathogen, producing mild infections in nearly the entire human population. These natural exposures induce Ad5-specific neutralizing antibodies (nAbs) that prevent reinfection or Ad5-based vaccination by preventing infection of host cells, a necessary step in target antigen expression and induction of immune responses. Ad5 nAbs were quantified in patient serum collected prior to Ad5-hGCC-PADRE vaccination (Day 0) using an Ad5-GFP reporter virus inhibition bioassay. Titers ranged from <10 to >10,000 and an obvious pattern emerged in which half of the patients had titers well below 200 (Ad5 nAb Low) and the other half had titers well above 200 (Ad5 nAb High;). Separating patients into Ad5 nAb Low and High cohorts revealed a relationship between Ad5 nAb titer and GCC-specific T-cell responses in which responses were significantly greater in Ad5 nAb Low patients. PADRE-specific T-cell responses which were generally low, showed no relationship to pre-treatment Ad5 nAb titer. Similar to GCC-specific T-cell responses, Ad5-specific T-cell responses were also limited by Ad5 nAb in the Ad5 nAb High group. Together, these data are in agreement with nonclinical data77 demonstrating that pre-existing Ad5 nAb immunity eliminates Ad5-hGCC-PADRE viral particles in vivo prior to entry into host cells, preventing subsequent gene expression and induction of host immune responses.

Ad5.F35-hGCC-Padre Rationale

Ad5 nAbs are common in most human populations, including ~40% in the US (Nwanegbo, E., et al. (2004) Clin Diagn Lab Immunol 11(2): 351-357.; Barouch, D. H., et al. (2011) Vaccine 29(32): 5203-5209), reducing the immunogenicity of Ad5-based vaccines (Priddy, F. H., et al. (2008). Clin Infect Dis 46(11): 1769-1781). Importantly, most naturally-occurring Ad5 nAbs target the fiber molecule on the surface of Ad5 (Cheng, C., et al. (2010) J Virol 84(1): 630-638). In contrast to Ad5, the seroprevalence of Ad35-specific antibodies in most countries is very low (<10%, Nwanegbo, E., et al. (2004) Clin Diagn Lab Immunol 11(2): 351-357; Barouch, D. H., et al. (2011) Vaccine 29(32): 5203-5209). Together, these observations suggest that replacement of the fiber molecule in Ad5 with the fiber molecule from Ad35 will produce a chimeric Ad5 viral vector (known as Ad5.F35) that is not affected by naturally-occurring Ad5 immunity. Indeed, in a cohort of 12 patients with pre-existing Ad5 nAbs, serum from eight patients (67%), was incapable of neutralizing chimeric Ad5.F35 in vitro. Moreover, while 50% of subjects in the Phase 1 study of Ad5-hGCC-PADRE possessed high Ad5 nAbs (titer >200), only 1/10 subjects possess high Ad5.F35 nAbs (FIG. 5). Thus, Ad5.F35 is advantageous compared to Ad5 by reducing the expected seroprevalence of Ad5.F35 nAbs to <25%, without additional safety risk. Ad5.F35-GUCY2C-PADRE is expected to overcome Ad5-specific preexisting immune which was not achieved by dose escalation as predicted by the published literature (Priddy, F. H., et al. (2008). Clin Infect Dis 46(11): 1769-1781).

The similarity between Ad5 and Ad5.F35 vectors in their immunogenicity, safety, and biodistribution profiles is supported by published nonclinical studies. Indeed, there is some indication that the safety profile may be better with Ad5.F35. While the Ad5.F35 transduction of muscle (the vaccination site) is comparable to Ad5, liver (1000×), spleen (3×), kidney (100×), heart (10×) and lung (100×) demonstrate significantly lower transduction efficiencies with Ad5.F35 than Ad5. In the context of the lower tropism of Ad5.F35 for liver, Ad5.F35 produced significantly lower elevations in serum proinflammatory cytokines and liver enzymes, suggesting that Ad5.F35 viruses have a better safety profile than Ad5 vectors. Moreover, Ad5.F35 vectors are significantly less sensitive to Ad5 nAbs than Ad5 vectors, increasing the magnitude of target-antigen-specific immune responses in animals with high Ad5 nAb titers (>200). Thus, Ad5.F35 vectors display better biodistribution, safety, and efficacy in the context of Ad5 nAbs than Ad5 vectors. Together, these data suggest that neutralizing immunity to Ad5.F35-hGCC-PADRE will be significantly lower in patients, increasing the rate and magnitude of GCC-specific T-cell responses in human subjects. In that context, we have modified the vaccine by replacing the Ad5 fiber molecule with the Ad35 fiber molecule, producing the chimeric viral vector Ad5.F35. This study will examine the safety, immunogenicity, and pre-existing nAbs resistance of Ad5.F35-hGCC-PADRE in patients with GI malignancies.

Ad5.F35-hGCC-PADRE Design

The Ad5.F35-hGCC-PADRE vaccine is composed of a recombinant, replication-deficient E1/E3-deleted Ad5.F35 virus possessing a GCC-PADRE expression cassette. This vaccine vector employs recombinant human type 5 adenovirus (rAd5), a stable non-enveloped icosahedral virus with a linear double-stranded DNA genome of ~38 kb, encoding >30 proteins. The rAd5 possesses deletions of the early E1 and E3 regions of the vector, enabling insertion of the GCC-PADRE cassette. E1/E3 deletion renders the virus replication-incompetent, increasing safety associated with its clinical use.

The GCC-PADRE cassette is composed of the human cytomegalovirus (HCMV) immediate-early promoter driving expression of a fusion product that consists of the extracellular domain of human GCC (residues 1-430) and the CD4+ T-cell epitope PADRE. In vivo, the Ad5.F35-hGCC-PADRE vector induces expression of the GCC-PADRE immunogen by infected cells, inducing an immune response against GCC and PADRE. PADRE is included in the vaccine to provide $CD4^+$ T-cell "help" to GCC-specific B and CD8+ T cells, producing superior immunity and antitumor efficacy in preclinical models compared to GCC vaccination without PADRE.

Ad5.F35-hGCC-PADRE Dose Rationale

Although the results from our Phase 1 study confirm the immunological response to Ad5-hGCC-PADRE vaccine, this was suppressed by the Ad5 neutralizing antibodies. Given the high prevalence of natural Ad5 exposure in the human population and consequential development of neutralizing antibodies which are found in as high as ~40% of patients, the current study will determine if sequential dose administrations, higher dose levels, and/or modification of the Ad5 backbone (Ad5 to Ad5.F35) overcome this barrier. This approach is supported by results with other Ad5 vaccines, in which higher dose levels could overcome high pre-existing Ad5 nAb titers to produce cellular immune responses.

The doses selected for this study are based on previous human experience with Ad5-hGCC-PADRE vaccine as well as other Ad5-based vaccine clinical trials. The $1\times10^{11}$ viral particles (vp) dose has been tested as a single administration in the previous Phase 1 clinical trial and was safe and tolerable. The current study examines repeat administration of $1\times10^{11}$ vp Ad5.F35-hGCC-PADRE administered intramuscularly (IM) four weeks apart for a total of three injections. Moreover, the study also explores two additional dose levels, also administered three times at four-week intervals. Together, the doses are $1\times10^{11}$ vp, $1\times10^{12}$ vp, and $5\times10^{12}$ vp. The maximum dose of $5\times10^{2}$ vp is approximately the highest dose achievable, given limitations on vaccine solubility.

Although the higher dose regimens ($1\times10^{12}$ and $5\times10^{12}$) of Ad5.F35-hGCC-PADRE employed in this Phase 2A study have not been previously tested in humans, other adenovirus-based vaccines have been administered at similar dose levels and were well tolerated. Similarly, repeat administration of the GCC-PADRE vectors has not been evaluated clinically but other studies have employed repeated administrations of adenovirus-based vaccines using comparable dose levels and were well tolerated.

Study Description

An investigational product is defined as a pharmaceutical form of an active ingredient being tested or used as a reference in the study. Ad5.F35-hGCC-PADRE, the active investigational product to be used in this study, is a replication-deficient adenovirus vaccine against human GCC protein formulated in TG buffer for intramuscular injection.

| Arm | Product | Concentration | Dosage Form & Route of Administration | Dose (mL) |
|---|---|---|---|---|
| A | Ad5.F35-hGCC-PADRE | $10^{11}$ vp/mL | Sterile TG buffer for IM immunization | 1.2 |
| B | Ad5.F35-hGCC-PADRE | $10^{12}$ vp/mL | Sterile TG buffer for IM immunization | 1.2 |
| C | Ad5.F35-hGCC-PADRE | $5\times10^{12}$ vp/mL | Sterile TG buffer for IM immunization | 1.2 |

Characteristics of Ad5.F35-hGCC-PADRE

Virus: Adenoviridae; non-enveloped, icosahedral virions, 70-90 nm diameter, double-stranded, linear DNA genome. Wild-type virus is lytic, while the E1/E3-deleted version in the vaccine is non-replicating.

Pathogenicity: Ad5.F35-hGCC-PADRE is a replication-deficient adenovirus, thus the risk from productive infection is low. The symptoms of wild-type adenoviral infection are fever, rhinitis, pharyngitis, cough and conjunctivitis. Adenoviruses can produce a strong immune response. Adenoviruses do not integrate into the host-cell genome, and Ad5.F35-hGCC-PADRE does not have any additional features that promote integration. The transgene expressed by Ad5.F35-hGCC-PADRE, produces a secreted GCC-PADRE fusion protein against which immune responses are generated. These responses are expected to have antitumor activity in patients.

Ad5.F35-hGCC-PADRE is an opalescent suspension of recombinant adenovirus type 5 particles that may contain visible particulates of protein origin in a liquid composed of Ad5.F35-hGCC-PADRE viral particles formulated in TG buffer (20 mM Tris-HCl, pH 8.0, 25 mM NaCl, 2.5% glycerol). The vaccine is supplied at the required concentration in vials containing 1.2 mL of a clear colorless sterile solution. Ad5.F35-hGCC-PADRE must be stored below −70° C., protected from light. No vials shall be thawed unless they are being dispensed. Freeze-thaw cycles diminish the vaccine potency and must be avoided.

Example 5

The ability of adenovirus serotype 5 (Ad5) to mediate gene transfer and induce potent immune responses has made it a popular vector for experimental vaccines against cancer and infectious diseases. Indeed, there have been more than 400 clinical trials using the Ad5 vector, with most trials focused on developing cancer treatments. However, on natural infection, the host immune system develops neutralizing antibodies (NAbs) to the Ad5 capsid, limiting viral spread and blocking reinfection. Because Ad5 infections are endemic in many human populations, pre-existing NAbs present in >70% of the worldwide population limit Ad5-based vaccine strategies. These considerations highlight the need for improved vectors for use in vaccines targeting cancer and pathogen-associated antigens that can create therapeutic immune responses in the greatest number of patients. Importantly, while the adenovirus capsid is composed of hexon, penton, and fiber proteins, NAbs elicited by natural Ad5 infection in humans are directed primarily to the Ad5 fiber, suggesting that strategies to circumvent pre-existing immunity to this element may improve Ad5-based vaccines.

We sought to overcome pre-existing Ad5 NAbs by replacing the Ad5 fiber with that of a rare adenovirus serotype. Ad35 (international seroprevalence ~10%), to improve antitumor immunity in mouse models expressing the gastrointestinal (GI) cancer antigen guanylyl cyclase C (GUCY2C). Preclinical models demonstrated that an Ad5-based GUCY2C-directed vaccine (Ad5-GUCY2C-S1) elicited CD8+ T-cell and antibody responses without autoimmunity. Further, Ad5-GUCY2C-S1 vaccination of mice induced long-term T-cell-mediated protection against metastatic colorectal cancer in lung and liver. Moreover, those results were recapitulated in a recent first-in-human phase I clinical trial (NCT01972737) demonstrating that a humanized version of the vaccine (Ad5-GUCY2C-PADRE) safely induced GUCY2C-specific CD8+ T-cell responses in patients with colorectal cancer following conventional therapies. However, patients possessing high pre-existing titers of NAbs against Ad5 failed to generate GUCY2C-specific immunity following Ad5-GUCY2C-PADRE vaccination. To overcome Ad5 NAbs, we generated a chimeric Ad5 vector possessing the fiber of Ad35 (Ad5.F35) with equivalent safety and antitumor activity to Ad5 and resistance to Ad5 NAbs in mice and humans. This chimeric vaccine can be translated to patients with GI cancer to safely induce GUCY2C-specific immunity not only in those patients with low Ad5 immunity but also in those with high pre-existing Ad5 NAbs.

Materials and Methods

Adenovirus Vectors

Adenovirus containing mouse extracellular domain ($GUCY2C_{1-429}$) with the influenza $HA_{107-119}$ CD4+ T-cell epitope known as site 1 (S1) was described previously (Ad5-GUCY2C-S1). Here, GUCY2C-S1 was cloned into pShuttle and subcloned into the E1 region of previously generated replication-deficient chimeric adenovirus (Ad5.F35) in which the Ad5 fiber was replaced by the Ad35 fiber to generate Ad5.F35-GUCY2C-S1. All adenovirus vaccines used in this study were produced in HEK293 cells and purified by cesium chloride ultracentrifugation under Good Laboratory Practices by the Baylor College of Medicine in the Cell and Gene Therapy Vector Development Lab and certified to be negative for replication-competent adenovirus, mycoplasma, and host cell DNA contamination. In vitro GUCY2C-expression experiments (dose-response and time-course) were carried out in A549 (American Type Culture Collection (ATCC)) cells. Virus was added to the cultures at the indicated doses and culture supernatants were collected at the indicated time points. Relative GUCY2C levels were quantified in supernatants by western blot using 2 μg/mL MS7 mouse anti-GUCY2C monoclonal antibody and 0.1 μg/mL horseradish peroxidase-conjugated goat anti-mouse secondary antibody (Jackson Immuno).

Mice and Immunizations

Eight-week old male and female BALB/cJ mice were purchased from the Jackson Laboratory for experiments. Animal protocols were approved by the Thomas Jefferson University Institutional Animal Care and Use Committee (Protocol 02092). For immunizations, mice received $10^{10}$ or $10^{11}$ vp of Ad5-GUCY2C-S1, Ad5.F35-GUCY2C-S1, or Ad5.F35-GFP (control) administered as two 50 μL intramuscular injections, one in each hind limb, using a 0.5 mL insulin syringe.

Quantifying T-Cell Responses by ELISpot

ELISpot assays were performed using a mouse interferon-γ (IFN-γ) single color ELISpot kit (Cellular Technology) according to the manufacturer's protocol. Briefly, 96-well plates were coated with IFN-γ capture antibody overnight at 4° C. The next day, plates were washed with phosphate-buffered saline (PBS) and splenocytes from immunized mice were plated at 500,000 cells/well with no peptide or 10 μg/mL $GUCY2C_{254-262}$ peptide in 0.1% dimethyl sulfoxide (DMSO) in CTL-TEST medium (Cellular Technology) for 24 hours at 37° C. For T-cell avidity studies, splenocytes were plated at 600,000-800,000 cells/well with decreasing concentrations of $GUCY2C_{254-262}$ peptide (10 μg/mL to 56 μg/mL) normalized to 106 cells/well. After incubation, cells were removed, and development reagents were added to detect IFN-γ-producing spot-forming cells. The number of spot-forming cells per well was determined using the SmartCount and Autogate functions of an ImmunoSpot S6 Universal Analyzer (Cellular Technology). GUCY2C-specific responses were calculated by subtracting mean spot counts of 0.1% DMSO wells from peptide-stimulated wells.

Tumor Studies

GUCY2C-expressing mouse (BALB/c) CT26 colorectal cancer cells were used for in vivo tumor studies. Luciferase-expressing cells were generated by transduction with lentiviral supernatants produced by 293FT cells (Invitrogen) with pLenti4-V5-GW-luciferase. For tumor experiments, BALB/cJ mice were immunized with 1010 vp of Ad5-GUCY2C-S1, Ad5.F35-GUCY2C-S1, or PBS (control) 7 days before delivering $5\times10^5$ CT26 cells into tail veins. Tumor burden was quantified weekly by subcutaneous injection of 3.75 mg of D-luciferin potassium salt (Gold Biotechnologies) in PBS followed by an 8 min incubation and imaging with a 10 s exposure using a Caliper IVIS Lumina XR imaging station (PerkinElmer). Total radiance (photons/second) was measured using Living Image In Vivo Imaging Software (PerkinElmer).

Antibody Neutralization Assay

Serum samples were obtained previously from patients before immunization with Ad5-GUCY2C-PADRE (NCT01972737) approved by the Thomas Jefferson University Institutional Review Board. Neutralizing antibody titers against Ad5 and Ad5.F35 vectors were quantified. Briefly, dilutions of heat-inactivated serum samples were added to 96-well tissue culture plates containing $10^5$ A549 cells (ATCC) and infected with $10^8$ vp of GFP-expressing Ad5 or Ad5.F35 virus (Ad5-CMV-eGFP or Ad5.F35-CMV-eGFP, respectively; Baylor Vector Development Lab). Following a 41-hour incubation at 37° C., eGFP fluorescence (490 nm excitation, 510 nm emission) was quantified using a POLARstar Optimate plate reader (BMG Labtech). Sample fluorescence was normalized to control wells containing cells and virus (0% neutralization) or wells containing cells alone (100% neutralization). Titers were quantified using non-linear regression as the serum dilution producing 50% neutralization (Prism v8, GraphPad Software).

Ad5 Neutralizing Immunity Studies

To induce anti-Ad5 immunity, mice were exposed intranasally to $10^{10}$ Ad5-GFP once or twice at a 4-week interval. Thirty days after the last exposure, Ad5 NAbs were quantified in sera as described above and mice were immunized intramuscularly with $10^{11}$ vp of Ad5-GUCY2C-S1 or Ad5.F35-GUCY2C-S 1.

Biodistribution and Toxicology Study

BALB/cJ mice were immunized intramuscularly with a single dose of $10^{11}$ vp of Ad5.F35-GUCY2C-S1, three doses of $10^{11}$ vp of Ad5.F35-GUCY2C-S1 at 28-day intervals, or PBS (control). Animals were monitored for adverse events once daily with additional evaluations on the day of dosing (5 min, 1 hour, and 3 hours after dosing). On days 14 and 90, designated animals were sacrificed and brain, salivary glands, stomach, small intestine, colon, heart, lungs, kidneys, liver, and injection site were harvested and weighed for histopathological analysis by a blinded pathologist (pathology evaluation was performed by IDEXX BioAnalytics) and detection of viral DNA by quantitative PCR (qPCR) using the previously described assay for the GUCY2C transgene. Also, spleens were collected for histopathological analysis and detection of viral DNA as described above, as well as quantification of GUCY2C-specific T-cell responses by IFN-γ ELISpot as described above.

Statistical Analysis

Statistical analyses were conducted using GraphPad Prism Software v8. Statistical significance was considered as follows: ns=p >0.05, * p<0.05, p<0.01, *p<0.001, and ****p<0.0001. Cohort sizes were powered based on prior studies with β=0.2 and α=0.05. For multiple comparisons of survival outcomes, significance thresholds were corrected using the Bonferroni method. To identify vaccine-induced T-cell responders and non-responders, a modified distribution-free resampling approach was employed and positive T-cell responses were defined as 2× compared with DMSO and >20-specific spots/$10^6$ cells. To determine the impact of gender and number of vaccinations on responses, log-transformed vaccine response magnitude was compared in mice of different genders, cohorts, and treatment regimens for up to three-way interactions, with stepwise backward variable selection by Akaike information criterion using R package MASS.

Results

Ad5-GUCY2C-S1 and Ad5.F35-GUCY2C-S1 Vectors

Figure 6:
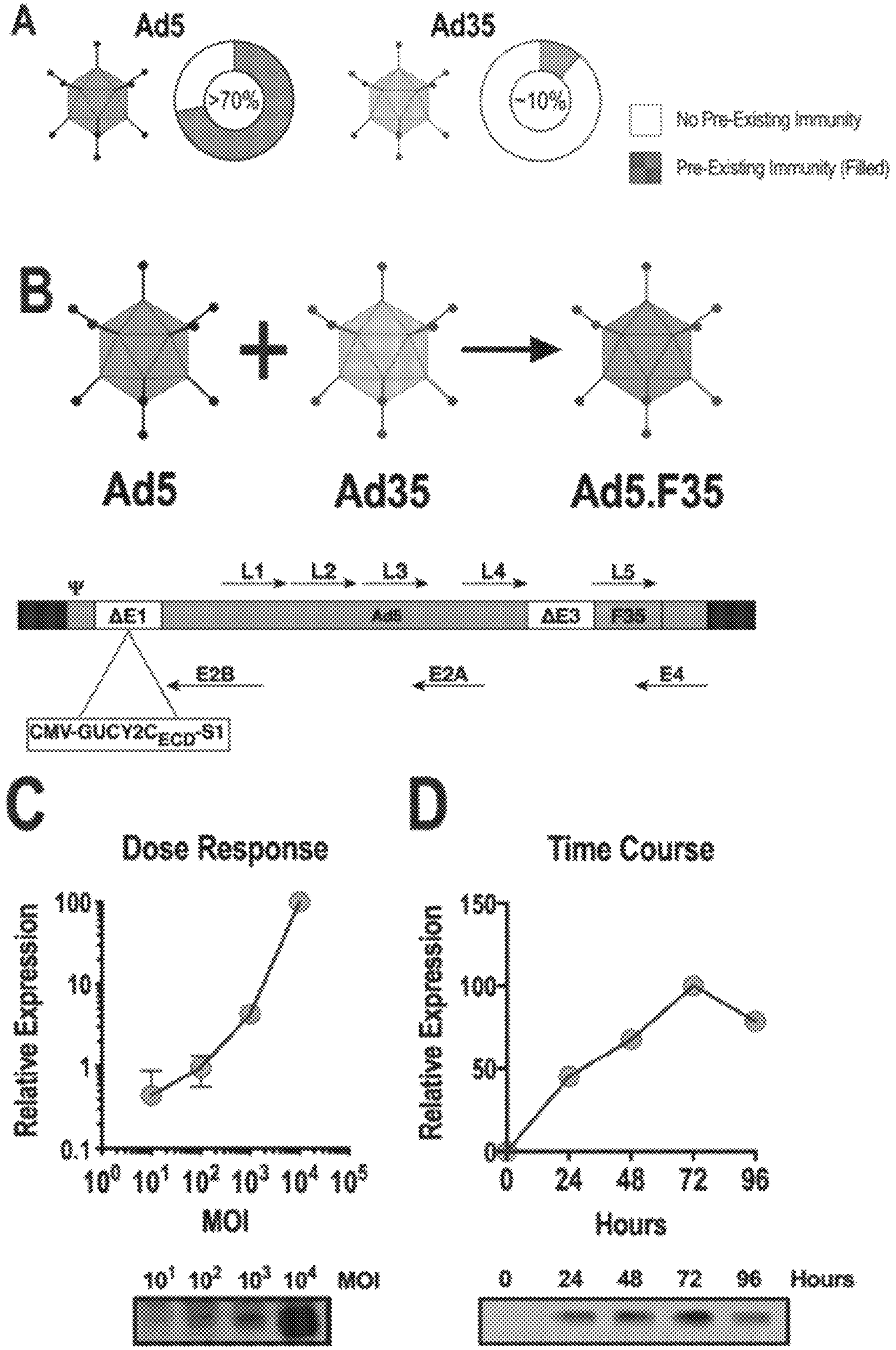
FIG. 6 panels A-D Construction of Ad5.F35-GUCY2C-S1 and antigen expression. (A) Reported international sero-prevalence of Ad5 and Ad35.12 (B) The L5 gene encoding the fiber protein from Ad5 was replaced with the L5 gene from Ad35, producing the chimeric adenoviral vector Ad5.F35. Recombinant Ad5.F35-GUCY2C-S1 was produced by inserting mouse GUCY2C-S1 into the E1 region of E1/E3 deleted Ad5.F35. (C and D) The human alveolar basal epithelial cell line, A549, was transduced in duplicate with Ad5.F35-GUCY2C-S1 at a multiplicity of infection (MOI) from 0 to 10,000 for 48 hours (C) or at an MOI of 10,000 for 0, 24, 48, and 72 hours (D). Supernatants from infected cells were analyzed for GUCY2C-S1 protein expression by immunoblot. Protein expression was quantified by densitometry and plotted relative to uninfected cells. Error bars indicate mean±SEM. Ad5, adenovirus serotype 5.

While Ad5 seroprevalence worldwide exceeds 70% (>90% in some regions), Ad35 is ~10% and associated with lower titers FIG. 6 panel A. Thus, we constructed a chimeric adenovirus (Ad5.F35) composed of Ad5 in which the fiber was replaced by the Ad35 fiber and evaluated its ability to induce GUCY2C-specific immunity and resist Ad5-specific immunity in humans and mice. Ad5-GUCY2C-S1 is a replication-deficient human Ad5 expressing the mouse GUCY2C extracellular domain fused to the 1-Ed-restricted CD4+ epitope known as site 1 at its C-terminus. To generate Ad5.F35-GUCY2C-S1, the Ad5 fiber (L5) was replaced with the Ad35 fiber (FIG. 6 panel B). Replication-deficient Ad5-GUCY2C-S1 and Ad5.F35-GUCY2C-S1 generated in HEK293 cells produced dose-dependent (FIG. 6 panel C) and time-dependent (FIG. 6 panel D) expression of GUCY2C-S1 protein in A549 human alveolar basal epithelial cells in vitro.

Ad5.F35-GUCY2C-S1 Induces GUCY2C-Specific Antitumor Immunity

Figure 7:
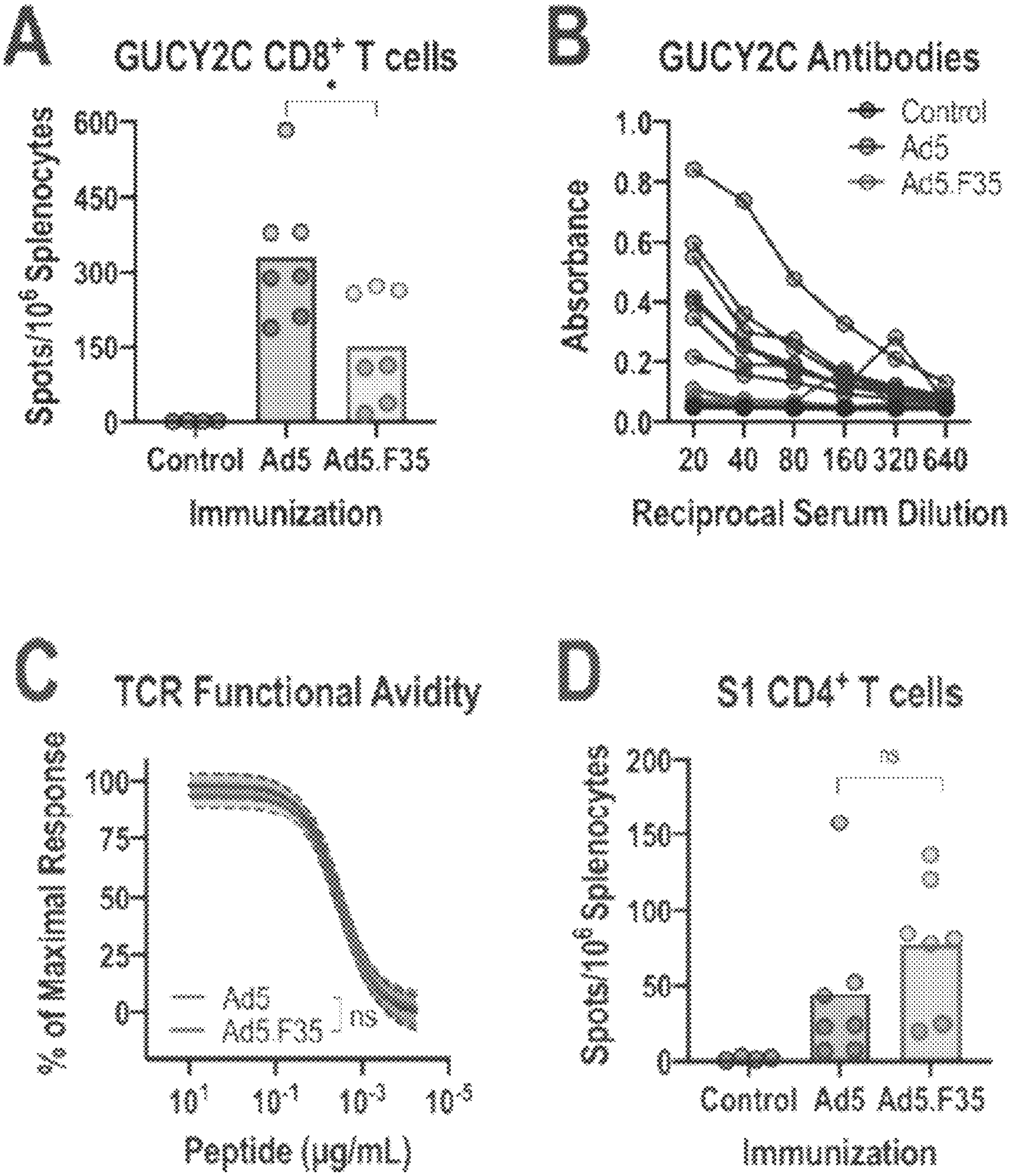
FIG. 7 panels A-D. Construction of Ad5.F35-GUCY2C-S1 and antigen expression. (A) Reported international sero-prevalence of Ad5 and Ad35.12 (B) The L5 gene encoding the fiber protein from Ad5 was replaced with the L5 gene from Ad35, producing the chimeric adenoviral vector Ad5.F35. Recombinant Ad5.F35-GUCY2C-S1 was produced by inserting mouse GUCY2C-S1 into the E1 region of E1/E3 deleted Ad5.F35. (C and D) The human alveolar basal epithelial cell line, A549, was transduced in duplicate with Ad5.F35-GUCY2C-S1 at a multiplicity of infection (MOI) from 0 to 10,000 for 48 hours (C) or at an MOI of 10,000 for 0, 24, 48, and 72 hours (D). Supernatants from infected cells were analyzed for GUCY2C-S1 protein expression by immunoblot. Protein expression was quantified by densitometry and plotted relative to uninfected cells. Error bars indicate mean±SEM. Ad5, adenovirus serotype 5.

Following in vitro validation of GUCY2C expression by Ad5.F35-GUCY2C-S1, we confirmed its ability to induce GUCY2C-specific immune responses after vaccination in vivo. BALB/c mice immunized intramuscularly with $10^{10}$ vp of Ad5.F35-GUCY2C-S1 produced 54% lower GUCY2C-specific $CD8^+$ T-cell responses (FIG. 7 panel A), and no GUCY2C-specific antibody responses (FIG. 7 panel B) compared with Ad5-GUCY2C-S1. Importantly, Ad5 and Ad5.F35 vaccines produced GUCY2C-specific $CD8^+$ T cells of comparable avidity FIG. 7 panel C), a critical determinant of the antitumor efficacy of GUCY2C-targeted vaccines. In contrast, GUCY2C-specific antibody responses have no detectable antitumor activity. Similarly. Ad5 and Ad5.F35 vaccines produced comparable S1-specific $CD4^+$ T-cell responses (FIG. 7 panel D).

Figure 8:
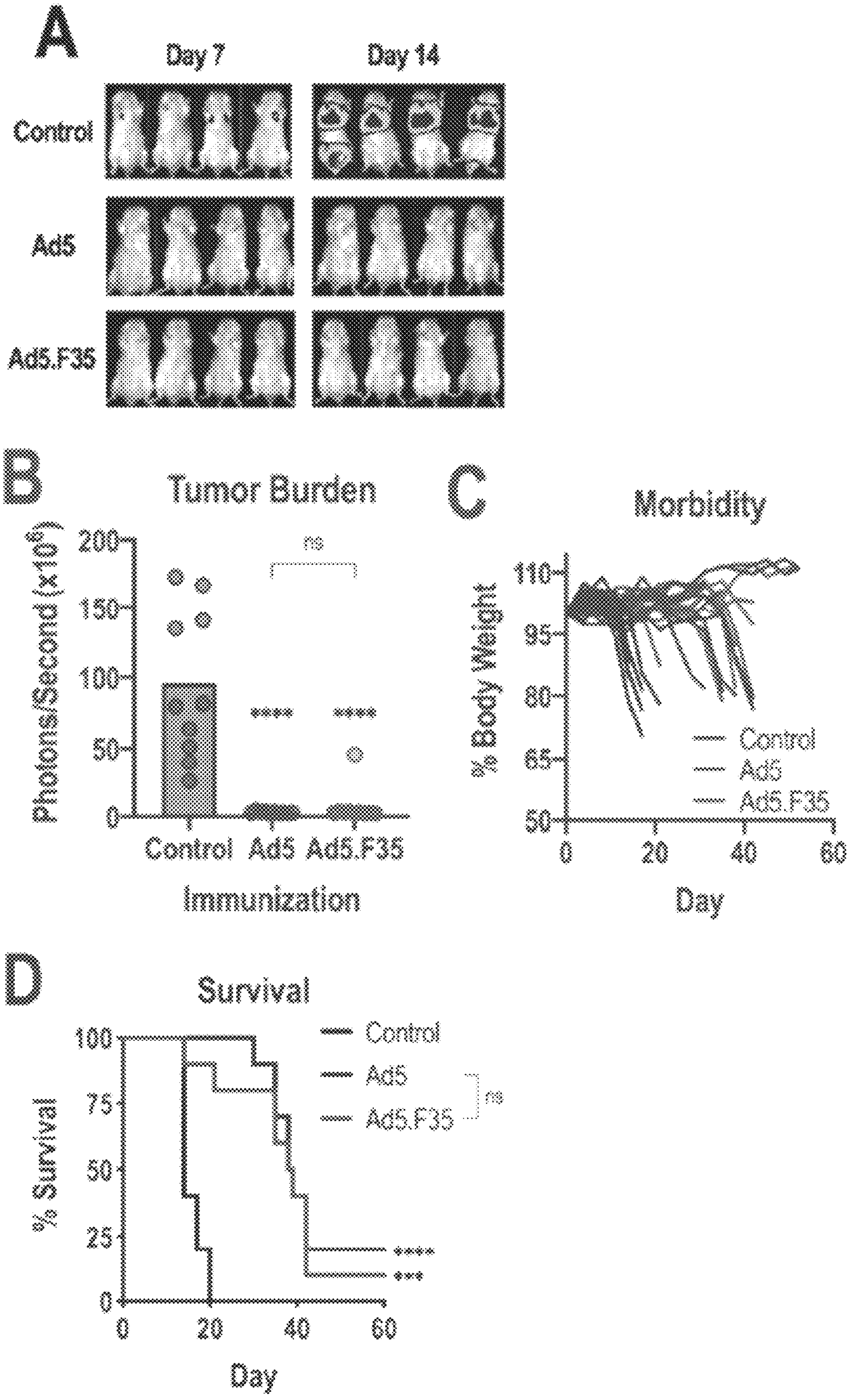
FIG. 8 panels A-D. Antitumor efficacy of Ad5-GUCY2C-S1 and Ad5.F35-GUCY2C-S1. (A-D) BALB/c mice (n=10 mice/group) were immunized intramuscularly with control or $10^{10}$ vp of Ad5-GUCY2C-S1 or Ad5.F35-GUCY2C-S1 and challenged 7 days later with a mouse colorectal cancer cell line, CT26, expressing GUCY2C and luciferase. On days 7 and 14 following challenge, mice were injected with D-luciferin and imaged (A) to quantify tumor burden (day 14; B). Mice were weighed twice weekly (C) and monitored for survival (D). Tumor burden (B) was analyzed by one-way analysis of variance and survival comparisons (D) were analyzed by the Mantel-Cox log-rank test. In (B) and (D), asterisks (*) indicate comparisons of GUCY2C vaccines to the control and brackets (1) indicate comparisons between Ad5 and Ad5.F35 vaccines. ns, not significant; Ad5, adenovirus serotype 5.

Previous studies revealed that Ad5-GUCY2C vaccines induced protective antitumor $CD8^+$ T-cell responses in murine models of metastatic colorectal cancer. Thus, BALB/c mice were immunized with Ad5 or Ad5.F35 expressing GUCY2C-S1 and challenged 7 days later with CT26 colorectal cancer cells expressing GUCY2C and firefly luciferase. This model specifically emulates secondary prevention of metastatic disease, the clinical setting for which the GUCY2C vaccine is being developed. As previously demonstrated. Ad5 vaccination nearly eliminated metastatic tumor burden (FIG. 8 panel A and B) delayed disease progression (FIG. 8 panel C) and improved survival (FIG. 8 panel D) @@. Similarly, Ad5.F35 also reduced tumor burden (FIG. 8 panel A and B), disease progression (FIG. 8 panel C), and prolonged survival (FIG. 8 panel D). Importantly, the efficacy of Ad5-based and Ad5.F35-based GUCY2C vaccines in reducing tumor burden, opposing disease progression, and promoting survival was identical (FIG. 8 panel A-D).

Ad5.F35 Resists Ad5-Directed Immunity in Mice and Humans

Figure 9:
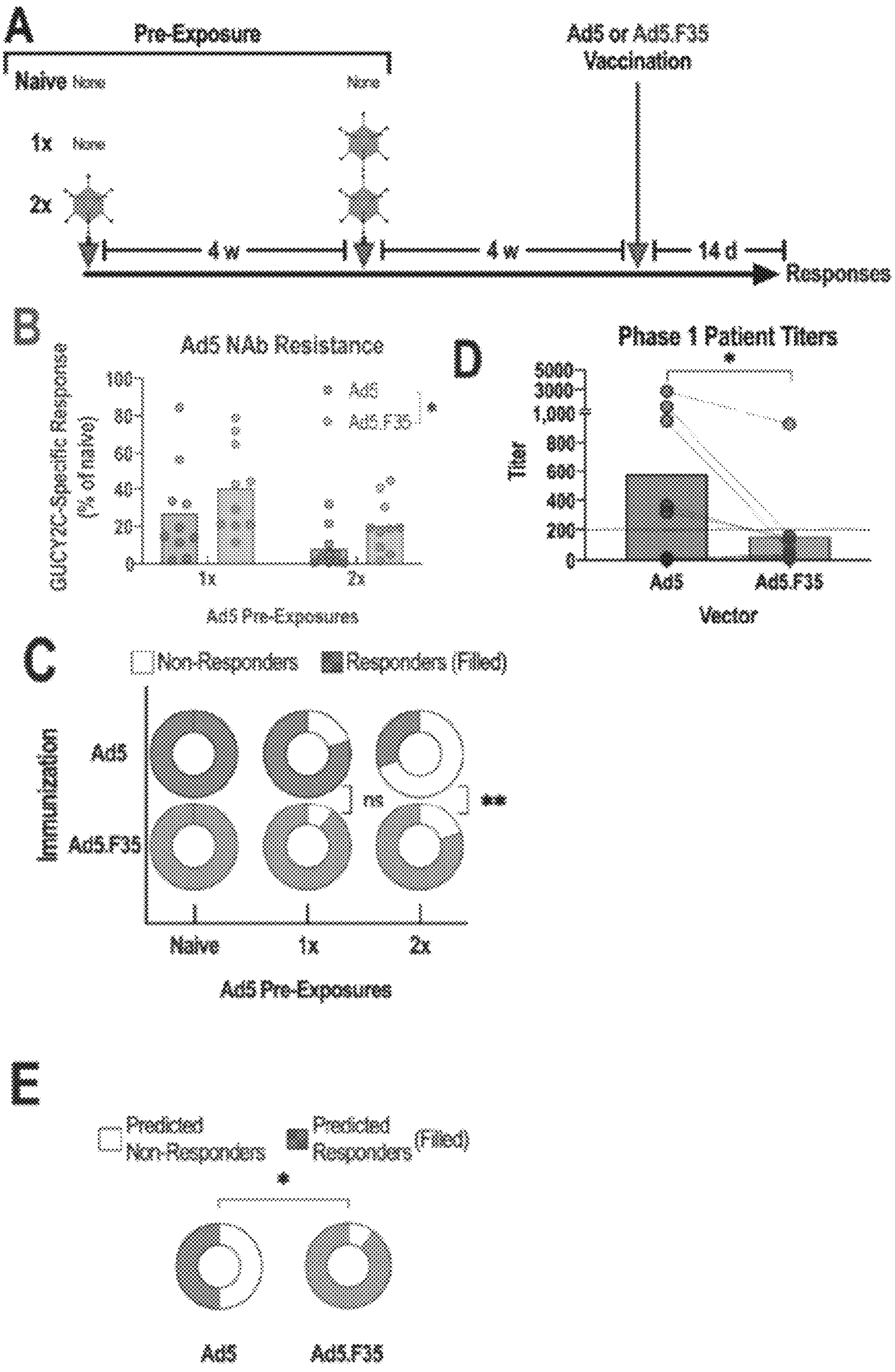
FIG. 9 panels A-E. Ad5.F35 resists neutralization associated with pre-existing anti-Ad5 immunity in mice and humans. (A-C) To generate pre-existing immunity to Ad5, BALB/c mice (n=10 mice/group) were exposed intranasally once or twice to 1010 vp of Ad5-GFP at 4-week intervals. Four weeks after the final Ad5-GFP exposure, Ad5-exposed and naive mice were immunized intramuscularly with 1011 vp of Ad5-GUCY2C-S1 or Ad5.F35-GUCY2C-S1. (B), Two weeks after immunization, GUCY2C-specific CD8+ T-cell responses in each group were quantified by interferon gamma (IFN-γ) ELISpot and calculated as the % of mean responses in naive mice. Values indicate individual animals and bars indicate means. Ad5 and Ad5.F35 were compared by two-way analysis of variance. (C) The fraction of animals producing a detectable GUCY2C-specific CD8+ T-cell response (filled regions) in naive, 1×, and 2× Ad5-exposed mice was determined from (B). (D and E) Sera from 10 patients with colorectal cancer collected prior to Ad5.GUCY2C-PADRE vaccination were tested for the ability to neutralize Ad5 and Ad5.F35 vectors and titers were quantified (D; analyzed by paired t-test). The dotted line indicates a titer of 200, the threshold for high neutralizing antibody (NAb) titers.21 (E) While 5/10 subjects had high NAb titers (>200) against Ad5, only 1/10 had high titers to Ad5.F35 vector (filled regions; binomial test). Ad5, adenovirus serotype 5.

NAbs against Ad5 correlated with poor GUCY2C-specific immune responses in patients receiving Ad5-GUCY2C-PADRE vaccination, and prior exposure of mice to Ad5 similarly blunted vaccine-induced immunity. Ad5.F35-based vaccine resistance to pre-existing Ad5 immunity was quantified in a model of respiratory pre-exposure to Ad5, the natural route of infection in patients, followed by vaccination and quantification of GUCY2C-specific T-cell responses. Control mice (not pre-exposed to Ad5; naive) and those that were pre-exposed once (lx) or twice (2×) to intranasal Ad5 were vaccinated after 4 weeks with intramuscular Ad5 or Ad5.F35 expressing GUCY2C-S1, and immune responses were quantified 2 weeks later (FIG. 9 panel A). As expected, one Ad5 pre-exposure induced moderate (<1:200) Ad5 NAbs and reduced GUCY2C-specific T-cell responses ~75%, while two pre-exposures induced high (>1:200) Ad5 NAbs and reduced GUCY2C-specific T-cell responses >90% following Ad5 vaccination (FIG. 9 panel B). In contrast, GUCY2C-specific T-cell responses were reduced only 60% (1× pre-exposure) and 80% (2× pre-exposure) following Ad5.F35 vaccination (FIG. 9 panel B). Importantly, Ad5.F35 produced T-cell responses in a substantially greater fraction of the population (80% cohort responses), compared with Ad5 (30% cohort responses), following serial pre-exposures to Ad5 (FIG. 9 panel C).

These observations in mice were recapitulated using sera from patients with colorectal cancer in the Ad5-GUCY2C-PADRE phase I trial (NCT01972737). Here, NAb titers against Ad5 and Ad5.F35 were quantified using an established Ad5/Ad5.F35 reporter virus inhibition bioassay in serum samples collected prior to vaccination with Ad5-GUCY2C-PADRE. In these patients, Ad5.F35-specific NAb titers were substantially lower than Ad5-specific titers (FIG. 9 panel D). Most importantly, 50% of patients possessed low (<1:200) Ad5 NAbs titers (FIG. 9 panel D and E) which closely correlated with a 40% GUCY2C-specific response rate. In striking contrast, 90% had low Ad5.F35 NAb titers, suggesting that the vast majority of patients immunized with Ad5.F35-based vaccines could produce GUCY2C-specific responses (FIG. 9 panel E). Collectively, these observations suggest that pre-existing viral immunity induced by repeated environmental exposures which neutralizes Ad5 delivery platforms may be overcome by the chimeric Ad5.F35 vector to enhance fractional population vaccine responses.

Safety, Biodistribution, and Toxicity of Ad5.F35-GUCY2C-S1

Figure 10:
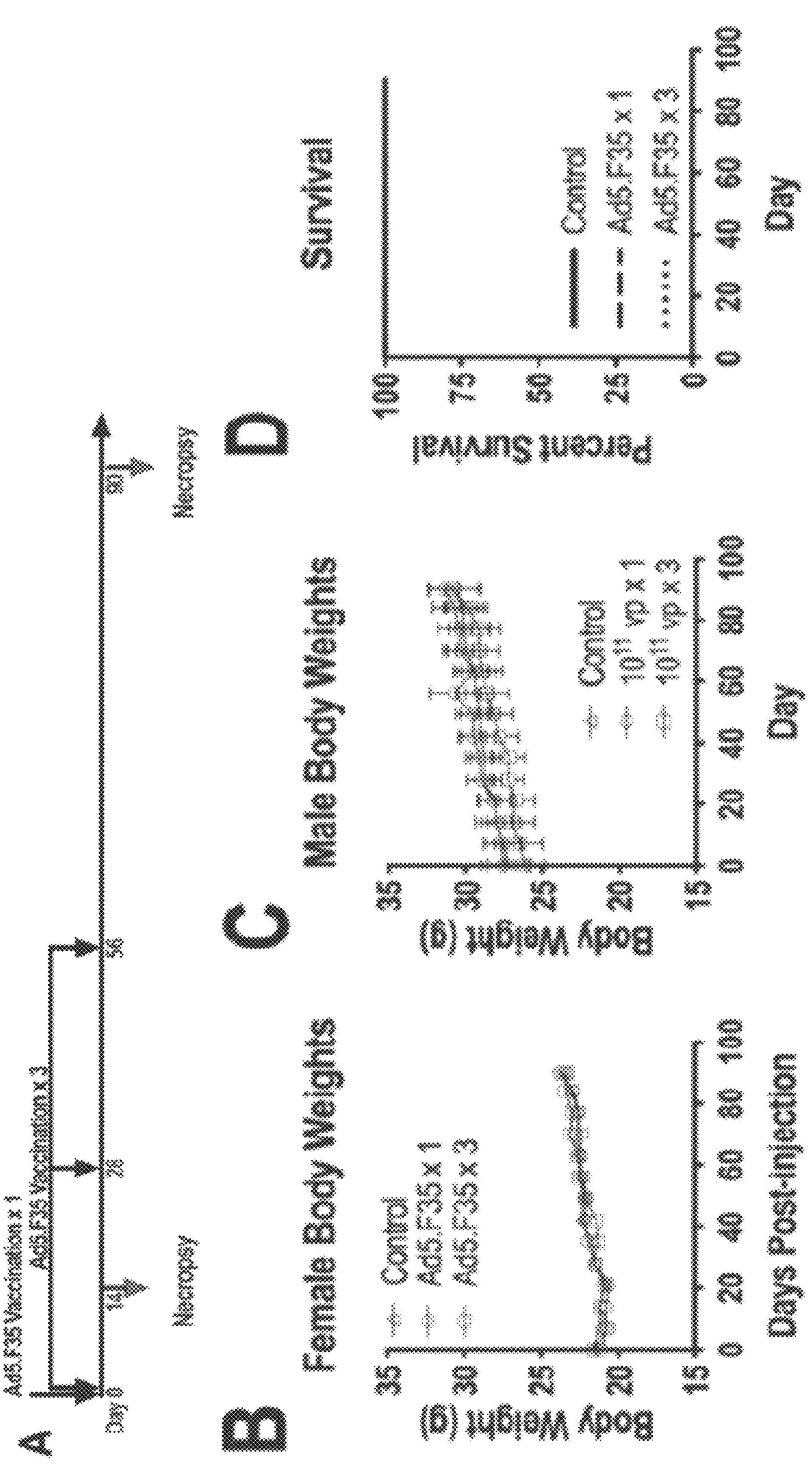
FIG. 10 panels A-F. Safety and immunogenicity of multiple Ad5.F35-GUCY2C-S1 administrations. (A-F) BALB/c mice (n=10 mice/group) were immunized intramuscularly with one or three administrations of 1011 vp Ad5.F35-GUCY2C-S1 or control at 4-week intervals. Following immunization, body weights ((B), female and (C) male)) were recorded weekly and mice were monitored for survival (D). At days 14 and 90 following first immunization, mice were euthanized to quantify organ pathology by weight, biodistribution by quantitative PCR, and GUCY2C-specific CD8+ T-cell responses by interferon gamma (IFN-γ) ELISpot (E-F).
Figure 10:
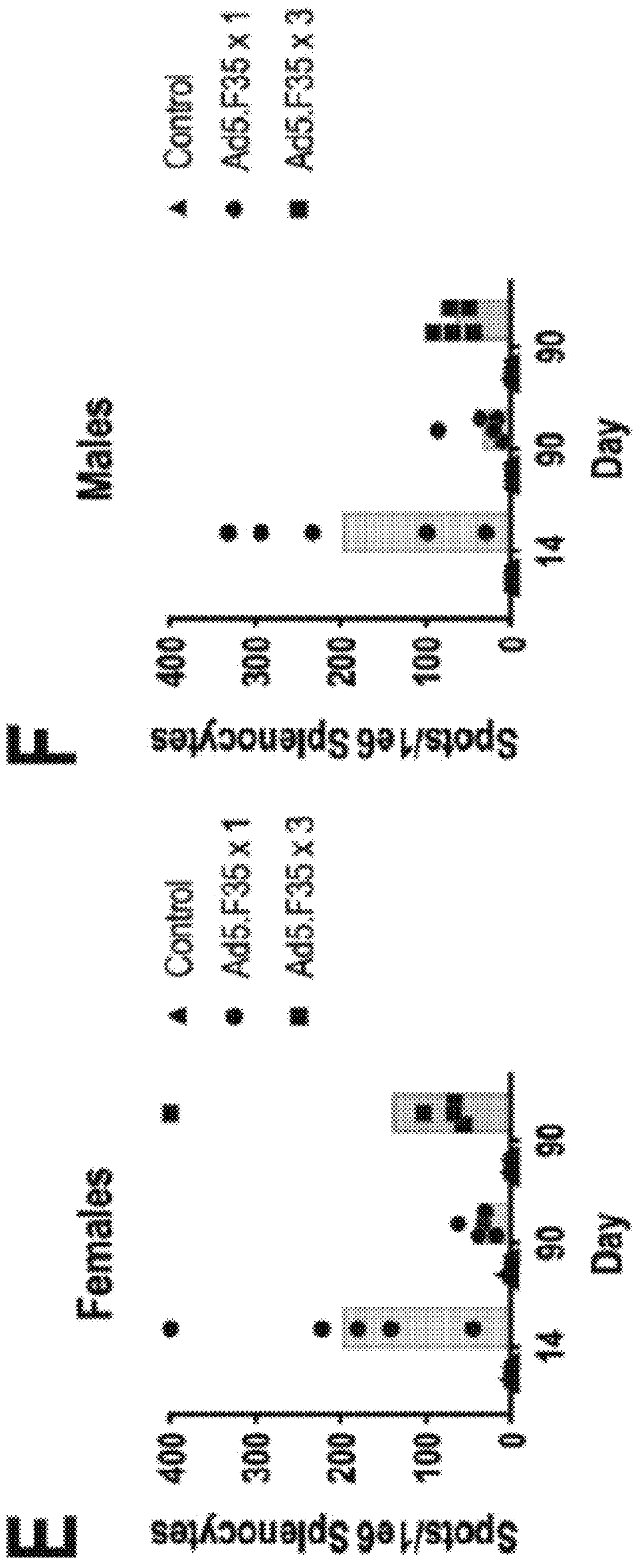

Food and Drug Administration IND (Investigational New Drug)-enabling studies quantified the toxicity, biodistribution, and immunogenicity of Ad5.F35-GUCY2C-S1 in BALB/c mice, employing three schemes to examine acute and chronic effects (FIG. 10 panel A). Cohorts, balanced for sex, received $10^{11}$ Ad5.F35-GUCY2C-S1 either as a single intramuscular injection or as three intramuscular injections spaced 4 weeks apart, monitored daily, and sacrificed on day 14 or 90 for analysis, as indicated (FIG. 10 panel A). There were no signs of acute or chronic toxicity in the in-life phase by observation, weight changes, or survival (FIG. 10 panel A-D). Similarly, there were no clinically significant differences in organ weights or histopathology (not shown) at necropsy. Small statistical differences in organ weights were considered clinically insignificant and were unrelated to vaccine exposure (dose, time). Biodistribution, quantified by qPCR, detected Ad5.F35-GUCY2C-S1 at the injection site and in the spleen, but not appreciably in other organs, after acute and chronic exposures. Moreover, robust $CD8^+$ T-cell responses were quantified at day 14 that persisted through day 90 in 70% of mice after a single administration (FIG. 10 panel E-G). As expected, $CD8^+$ T-cell responses were greater, and persisted in more mice (100%), at 90 days after three vaccinations (FIG. 10 panel E-G).

Discussion

Through decades of gene therapy trials, Ad5 has remained a popular vector, while high Ad5 seroprevalence remains a barrier to universal vaccination. Natural respiratory infection can generate long-lived antibodies that neutralize Ad5-based vaccines, eliminating transgene delivery and potential therapeutic benefit. In that context, Ad5 seroprevalence is >70% across multiple countries, highlighting an unmet need for alternative vectors. Here, we demonstrate that the chimeric Ad5.F35 resists pre-existing Ad5 immunity and induces transgene-specific antitumor immunity. Indeed, Ad5.F35 is less susceptible to neutralization associated with Ad5 exposure in mice and humans and generates a substantially higher proportion of vaccine responders in mice pre-exposed to Ad5. These observations support the suggestion that Ad5.F35 will produce a higher proportion of vaccine responders in patient populations.

The extent to which NAbs to the Ad5 fiber limit reinfection is controversial. In some studies, replacing the Ad5 fiber with that of another serotype circumvents pre-existing Ad5 immunity. In contrast, other studies suggest that these chimeric adenoviruses do not evade pre-existing Ad5 NAbs, suggesting the hexon as the major target of antibody neutralization. In contrast to those previous studies, which generated pre-existing Ad5 immunity by intramuscular or intravenous administration, here Ad5 immunity was induced by intranasal exposure in mice, recapitulating natural human respiratory infection. Moreover, natural pre-existing Ad5 NAbs in patients with colorectal cancer, uniformly produced by repeated respiratory infections, similarly were overcome by the Ad5.F35 vector. Importantly, the quality of antibody responses following adenovirus infection is dependent on the route of exposure. Indeed, respiratory infections elicit fiber-specific NAbs while intramuscular exposure induce capsid-specific NAbs. These qualitative differences in NAb responses, reflecting varying routes of immunization, may contribute to observational discrepancies between laboratories. The present studies, using relevant animal models, confirmed and validated with patient samples, support the suggestion that Ad5.F35-based vaccines should produce clinically relevant immune responses in a substantial (~90%) proportion of patients.

Recognizing the pervasive limitations imposed by endemic Ad5 immunity in global populations, there is an emerging interest in alternative serotypes and chimeric constructs as a tractable strategy in vaccine development. Ad26, Ad35, and Ad48 vectors have been advanced into phase I clinical trials. In that regard, a comparison of Ad5, Ad26, Ad35, and Ad48 immunity among healthy patients revealed that endemic Ad35 seropositivity was lowest across global populations, reinforcing chimeric strategies employed herein. Similarly, the first hexon-chimeric adenovirus, comprising Ad5 and Ad48 components, was safe and immunogenic in patients. Interestingly, Ad5-Ad35 chimeric vectors more efficiently transduce a variety of human cell types in vitro compared with either parental vector.

While antitumor efficacy was equivalent, $CD8^+$ T-cell responses were lower, and antibody responses were absent, for Ad5.F35-GUCY2C-S1, compared with Ad5-GUCY2C-S1. However, the antitumor efficacy of GUCY2C-directed immunotherapy is driven primarily by T-cell avidity, rather than effector T-cell quantity. In that context, the functional avidity of GUCY2C-specific $CD8^+$ T cells following Ad5 and Ad5.F35 immunizations were equivalent, consistent with their comparable antitumor efficacy. Quantitative differences in transgene-specific immunity between vectors may reflect a variety of factors. Thus, the quantity and persistence of GUCY2C-S1 transgene following Ad5.F35 immunization is lower compared with Ad5, consistent with prior observations that Ad5 transduction efficiency in vivo may be several-fold higher than Ad5.F35. Moreover, the Ad5 fiber binds to CXADR (coxsackievirus and adenovirus receptor) while the Ad35 fiber binds to CD46, suggesting the two viruses may infect distinct cell types.

While checkpoint inhibitors have generated practice-shifting results in the clinic and defined immunotherapy as an effective strategy for the treatment of several malignancies, they have not been universally successful. In that context, the dearth of neoepitopes in many cancer types, including microsatellite stable colorectal and pancreatic (second and third leading causes of cancer mortality, respectively), makes them insensitive to checkpoint blockade. Indeed, examination of neoepitopes presented on the surface of five colorectal cancer specimens revealed a total of three neoepitopes. Thus, vaccines targeting cancer-associated self-antigens have re-emerged, alone and in combination with checkpoint inhibitors, as a strategy to prevent and treat metastases from these cold tumors.

Checkpoint inhibitors have become first-line therapy in the metastatic setting for some cancers, while chimeric antigen receptor expressing T cells (CAR-T cells) are being deployed in patients with metastatic and refractory disease. In contrast, few cancer immunotherapies have been developed for early-stage cancer patients with "no evidence of disease" (NED) following conventional surgical/radio/chemotherapies, who are at significant risk of disease recurrence. Indeed, ~25% of stage II, and ~50% of stage III, patients with colorectal cancer recur following surgery and chemotherapy, while 70% of patients with resectable pancreatic cancer experience recurrence. Vaccines targeting tumor-associated antigens, such as Ad5.F35-GUCY2C-PADRE, may provide safe and effective immunotherapies for the secondary prevention of metastatic disease in patients with NED who are otherwise ineligible to receive checkpoint inhibitors or CAR-T cells.

The present studies suggest that the chimeric adenoviral vector Ad5.F35 may be preferable to the widely used Ad5 vector and warrants further investigation. Indeed, they suggest that ongoing clinical investigations of GUCY2C-directed immunotherapy in patients with GUCY2C-expressing cancers, including colorectal, pancreatic, gastric, and esophageal, could benefit from using the Ad5.F35, rather than the Ad5, vector. In that context, an upcoming clinical trial will examine the safety, immunogenicity, and resistance to pre-existing immunity of Ad5.F35-GUCY2C-PADRE in patients with GI cancer (NCT04111172). Safe generation of GUCY2C-targeted immunity in a high proportion of patients will lead to efficacy trials to establish the ability of Ad5.F35-GUCY2C-PADRE to prevent recurrence following standard therapy in patients with GI cancer, who represent 25% of all cancer deaths51 and for whom established immunotherapies are ineffective.

Example 6

Background: Recombinant attenuated *Listeria monocytogenes* (Lm) is an emerging platform for cancer immunotherapy, partly reflecting its insensitivity to vector-specific neutralizing immunity, a limitation of many viral vectors. Moreover, Lm is an intracellular bacterium with tropism to antigen-presenting cells (APCs), directing the vaccine to the immune cells responsible for initiating immune responses by activating CD4+ T-helper cells (Th cells) and CD8+ cytotoxic T cells (CTLs). These advantages align with the limitations of the Ad5-GUCY2C-PADRE vaccine recently tested in a Phase I clinical trial in colorectal cancer (CRC) patients. Ad5-GUCY2C-PADRE immunogenicity is limited in human populations by pre-existing neutralizing antibodies (NAbs) targeting the Ad5 viral vector. Moreover, GUCY2C-specific immune responses are characterized by the absence of CD4+ T-cell responses, essential for the induction of CD8+ T- and B-cell responses. In contrast, a Lm vaccine incorporating GUCY2C (Lm-LLO-GUCY2C) should be resistant to vector-specific immunity and, reflecting its tropism for APCs, should induce Lm-specific CD4+ T-cell responses that provide CD4+ T-cell help to GUCY2C-specific CD8+T and B cells, leading to CRC elimination.

Objective/Hypothesis: Lm-LLO-GUCY2C is superior to current GUCY2C vaccines, overcoming neutralizing antibodies and GUCY2C-specific CD4+ T-cell tolerance, to produce safe and effective CRC immunotherapy.

Specific Aims: This proposal will define the (1) immunogenicity, (2) antitumor activity in a metastatic CRC model, and (3) safety of Lm-LLO-GUCY2C.

Study Design: Lm-LLO-GUCY2C will be produced, and its immunogenicity will be tested in mice by quantifying GUCY2C-specific immune responses (CD4+ and CD8+ T and B cells). Further, Lm-specific CD4+ T-cell responses will be quantified, and their role in inducing GUCY2C-specific responses will be determined by CD4-depletion studies. The antitumor efficacy of Lm-LLO-GUCY2C will be tested in a mouse model of metastatic CRC and compared to the benchmark GUCY2C vaccine (Ad5-GUCY2C-S1). Finally, Lm-LLOGUCY2C toxicity will be examined, particularly in normal GUCY2C-expressing tissues. Positive and negative controls for the proposed studies include Ad5-GUCY2C-S1 and Lm-LLO (lacks GUCY2C), respectively.

Innovation: As GUCY2C vaccine development progressed from initiation to clinical testing, our understanding of GUCY2C immunobiology and vaccine platforms has advanced sufficiently to allow a more informed GUCY2C vaccine design. In that context, we hypothesize that the properties of Lm (resistance to vector immunity; APC tropism) and GUCY2C (intestine-specific: universal expression in CRC; selective CD4+ T-cell tolerance) may be mutually advantageous, producing an effective immunotherapy for CRC. In the context of established safety and efficacy of Lm vaccines and GUCY2C immunogenicity in patients, results here may be quickly translated to Phase I clinical trials, extending this hypothesis from animals to humans, which may ultimately lead to effective immunotherapy in civilian and military CRC populations.

The immunogenicity, efficacy, and safety of a Listeria-based cancer vaccine targeting GUCY2C (Lm-LLO-GUCY2C) as a potential CRC immunotherapy. CRC is the fourth most common neoplasm, with ~150,000 new cases per year, and the second leading cause of cancer mortality, in civilians and the military, with a mortality of ~50%.

Example 7

A vaccine to treat GUCY2C=expressing cancer. The vaccine uses attenuated *Listeria monocytogenes* to deliver GUCY2C, a colorectal cancer antigen to "antigen-presenting cells" (APCs) to induce GUCY2C-specific T cell responses against GUCY2C which may find and eliminate GUCY2C-expressing cancer. The novel recombinant *Listeria monocytogenes* vaccines are first tested in mouse models of colorectal cancer to determine their activity, efficacy, and safety.

Major Task 1: Generate Lm-LLO-GCC and control Lm vaccines

Major Task 2: Determine the ability of Lm-LLO-GCC to overcome tolerance in WT mice. Quantify Lm-LLO-GCC-induced immune responses in WT and KO mice Major Task 3: Determine whether GCC-specific responses are CD4+ T-cell dependent Quantify the antitumor activity of Lm-LLOGCC in a metastatic CRC model Compare the antitumor efficacy of LmLLO-GCC and Ad5-GCC-S1

Major Task 5: Compare the impact of vector-specific immunity on immune responses to Lm-LLO-GCC and Ad5-GCC-S1. Quantify immune responses in Lm-LLOGCC or Ad5-GCC-S 1-immunized mice with pre-existing vector specific immunity Major Task 6: Compare the impact of vector-specific immunity on Lm-LLO-GCC and Ad5-GCC-S1 antitumor efficacy. Quantify antitumor efficacy of Lm-LLOGCC or Ad5-GCC-S1 in mice with pre-existing vector-specific immunity Demonstrate the safety of Lm-LLO-GCC Major Task 7: Examine Lm-LLO-GCC-immunized mice for signs of toxicity. Establish Lm-LLO-GCC pathology in GCC expressing and non-expressing tissues.

1st Generation Recombinant Lm-LLO-GCC Vaccines

Figure 14:
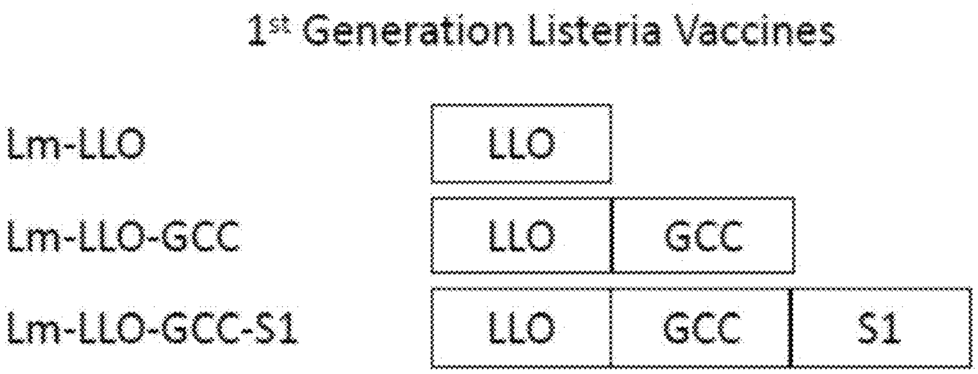
FIG. 14. 1st Generation Lm-GCC Vaccines. Three vaccines were generated: control Lm containing only the transfer plasmid without GCC; LLO-GCC fusion protein; and LLO-GCC-S1 fusion protein.

The integration plasmid pPL2 was used to induce recombinant GCC or GCC-S1 integration into the genome of attenuated (ΔactA/ΔinLB) *Listeria monocytogenes* (Lm) downstream of a truncated listeriolysin O (LLO) expression cassette and the LLO promotor, producing an LLO-GCC fusion protein that will be secreted into the cytosol of Lm-infected cells (FIG. 14). These constructs contain the full extracellular domain of GCC (residues 23-429) that has been used in previous viral vector-based vaccines.

Figure 15:
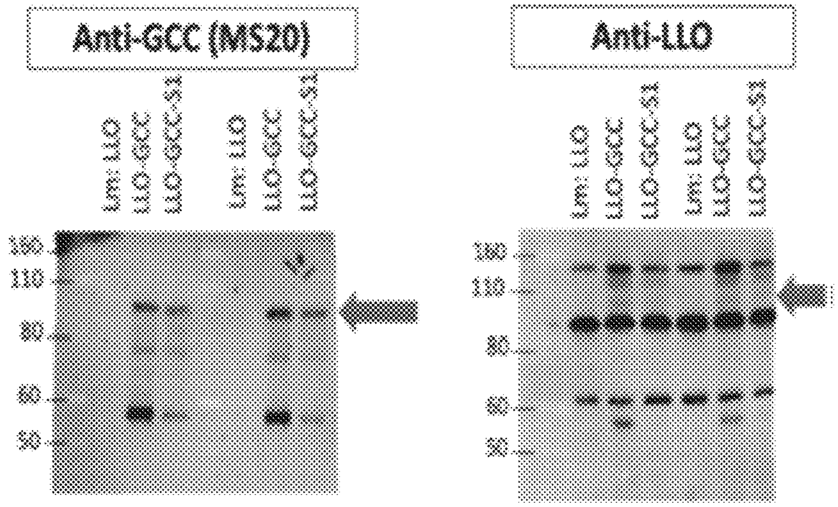
FIG. 15. 1st Generation Lm Vaccine Quality Control. Listeria cultures were grown at 37° C. At OD600 >0.5, cultures were centrifuged at 4,000×G for 10 minutes and supernatants were collected. Proteins were precipitated from supernatant using trichloroacetic acid. Protein (30 μg) was loaded in each lane of a 4-12% Bis-Tris Gel. Gels were stained with GCC monoclonal antibody (clone MS20) or polyclonal anti-LLO. Predicted weight of both LLO-GCC and LLOGCC-S1 fusion proteins is estimated ~89 kDa.

1st generation Lm-GCC and control vaccines were quality controlled by confirming GCC expression in supernatants of Lm cultures (FIG. 15). The LLO-GCC or LLO-GCC-S1 fusion proteins were detected in supernatants using anti-GCC or ani-LLO antibodies.

Figure 16:
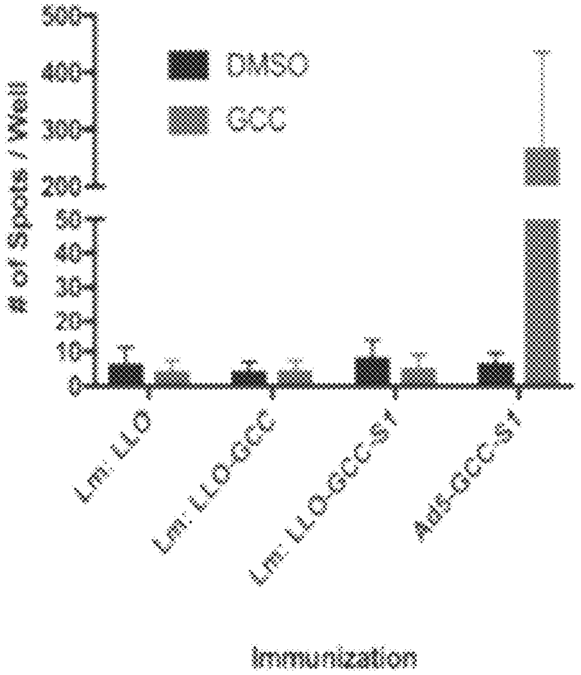
FIG. 16. 1st Generation Lm Vaccine Immunogenicity. Control (Lm-LLO), Lm-LLO-GCC, and Lm-LLO-GCC-S1 vaccines were administered to wild-type BALB/c mice at 107 CFU/mouse. Ad5-GCC-S1 was administered at 109 IFU as a positive control. GCC-specific CD8+ T-cell responses were measured by IFNγ-ELISpot. No responses were detected against GCC in the control, LmLLO-GCC, or Lm-LLO-GCC-S1-immunized mice but were readily detected in Ad5-GCC-S1—immunized mice (left). Lm and Ad5 vaccines induced strong vector-specific T-cell responses directed against LLO or DBP, respectively (right), confirming adequate Lm-LLO-GCC vaccine exposure and immunogenicity.
Figure 16:
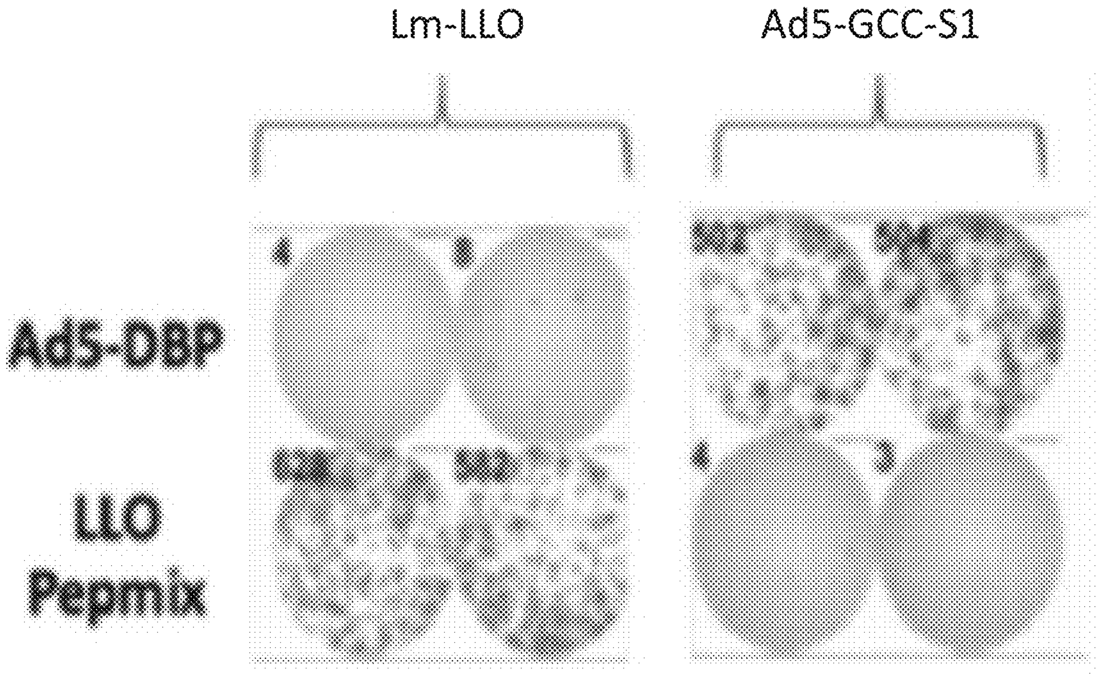

The immunogenicity of 1st-generation Lm-GCC vaccines was tested in BALB/c mice (FIG. 16). The well-established adenovirus-based vaccine (Ad5-GCC-S1) was used as a positive control. Following immunization, $CD8^+$ T-cell responses to GCC were quantified by IFNγ-ELISpot. As expected, control Lm-LLO induced no GCC-specific responses; however, Lm-LLO-GCC and Lm-LLO-GCC-S1 also failed to induce responses. Responses were induced by the positive control Ad5-GCC-S1 vaccine and responses were generated against the antigens LLO and DBP in the Lm and Ad5 vectors, respectively. Together, these data suggested that Lm-LLOGCC vaccines were poor inducers of GCC-specific responses.

2nd Generation Recombinant Lm-LLO-GCC Vaccines

Figure 17:
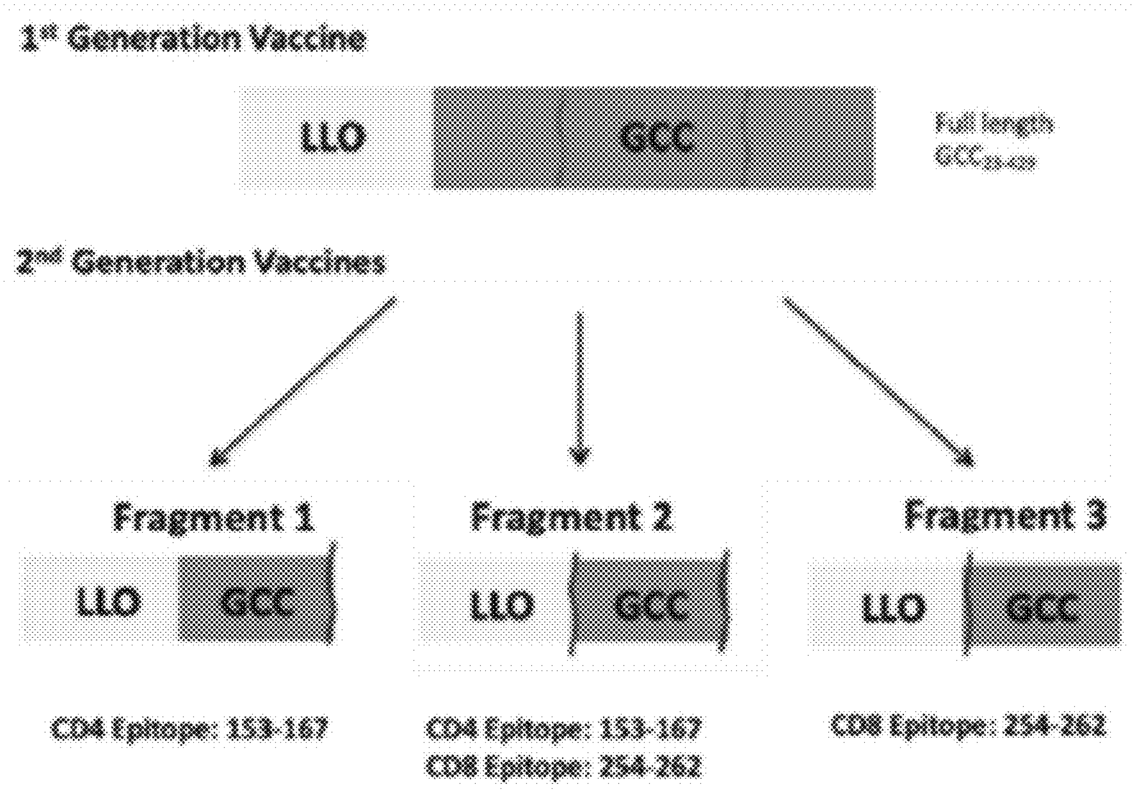
FIG. 17. 2nd Generation Lm-GCC Vaccine Design. While the 1st generation vaccines employed the full extracellular domain of GCC (residues 23-429), 2nd generation designs employed shorter fragments of GCC. Each fragment contained approximately 1/3 of GCC with discrete CD4+ and CD8+ epitope profiles indicated below each construct.

In the context of low LLO-GCC fusion protein expression (FIG. 15), we hypothesized that the large size of the LLO-GCC fusion protein may be interfering with its expression and induction of immunity. Indeed, similar studies with large tumor antigens fused to LLO show similar difficulty in generating the fusion protein. Therefore, we generated 3 different 2nd generation vaccines, each of which contained about 1/3 of GCC (FIG. 17). The designs contain different GCC CD4+ T-cell and $CD8^+$ T-cell epitopes allowing us to test responses to each epitope with two different fragments.

Figure 18:
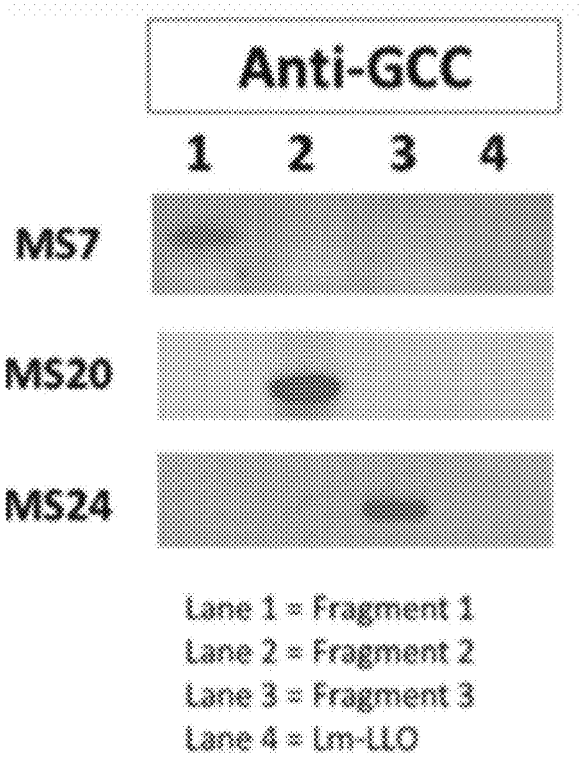
FIG. 18. 2nd Generation Lm Vaccine Quality Control. Listeria cultures were grown at 37° C. When OD600 >0.5, cultures were centrifuged at 4,000×G for 10 minutes and supernatants were collected. Proteins were precipitated from supernatant using trichloroacetic acid. Protein (30 μg) was loaded in each lane of a 4-12% Bis-Tris Gel. Gels were stained with GCC monoclonal antibodies MS7, MS20, MS24 and detected with HRP-conjugated goat anti-mouse secondary antibody and luminescent substrate.

Expression of the LLO-GCC fusion protein was confirmed in 2nd generation Lm-LLO-GCC vaccines by western blot. Because each 2nd generation vaccine contains a different GCC fragment, multiple GCC-specific monoclonal antibodies were used to detect GCC-LLO fusion proteins in Lm supernatants (FIG. 18). These data confirm LLO-GCC fusion protein expression by each recombinant Lm vaccine. As expected, the shorter fusion proteins were expressed at higher levels than the full-length LLOGCC product produced in the 1st generation vaccine.

Figure 19:
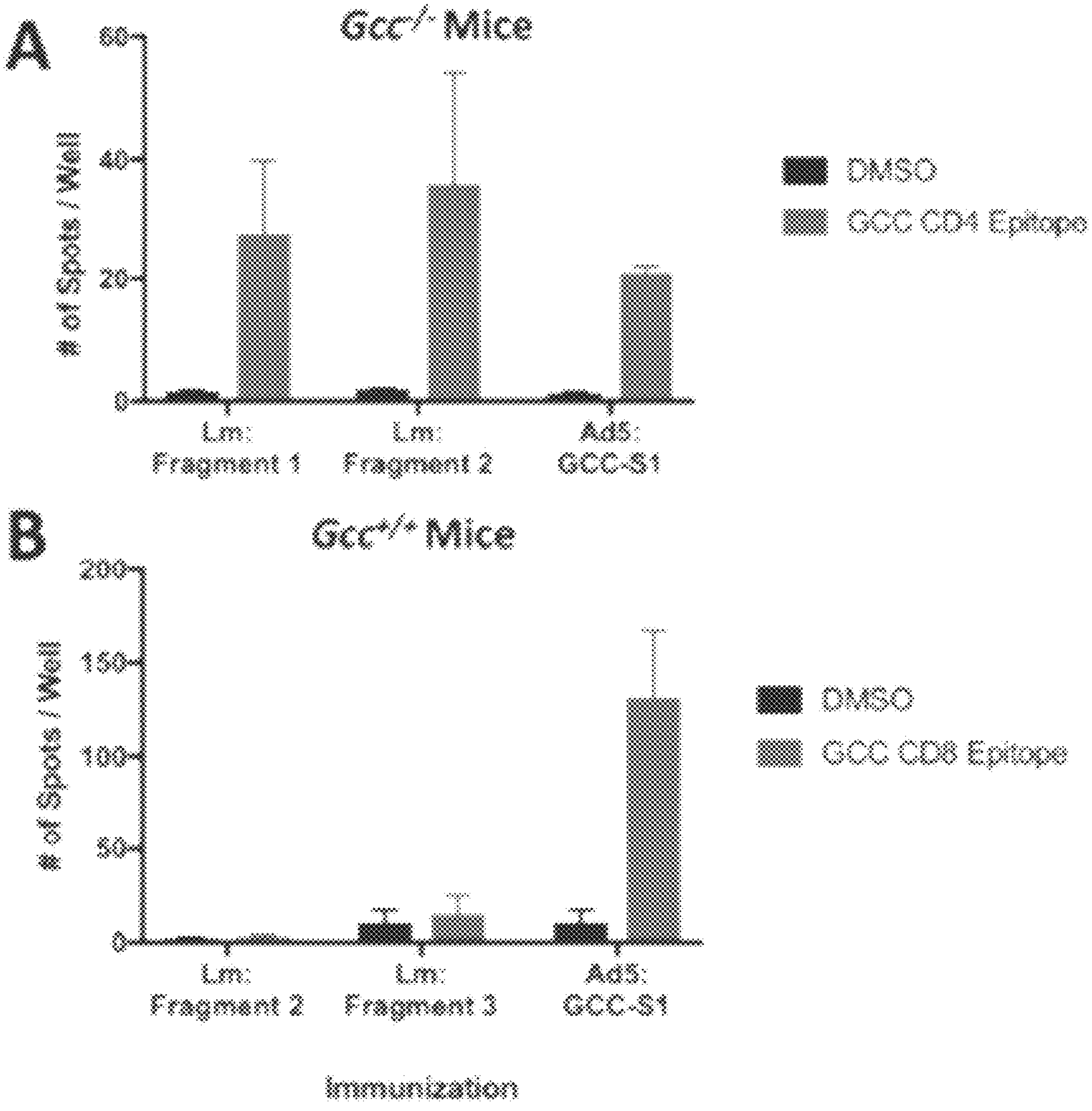
FIG. 19, panels A and B. 2nd Generation Vaccine immunogenicity. 2nd generation Lm-LLO-GCC vaccines containing GCC fragments were administered to Gcc−/− (A) or Gcc+/+ (B) mice. Gcc−/− mice produced robust $CD4^+$ T-cell responses against GCC when immunized with the $CD4^+$ T-cell epitope-containing fragments 1 and 2 (A). However, Gcc+/+ mice failed to produce GCC-specific $CD8^+$ T-cell responses when immunized with the $CD8^+$ T-cell epitope-containing fragments 2 and 3 (B)
Figure 20:
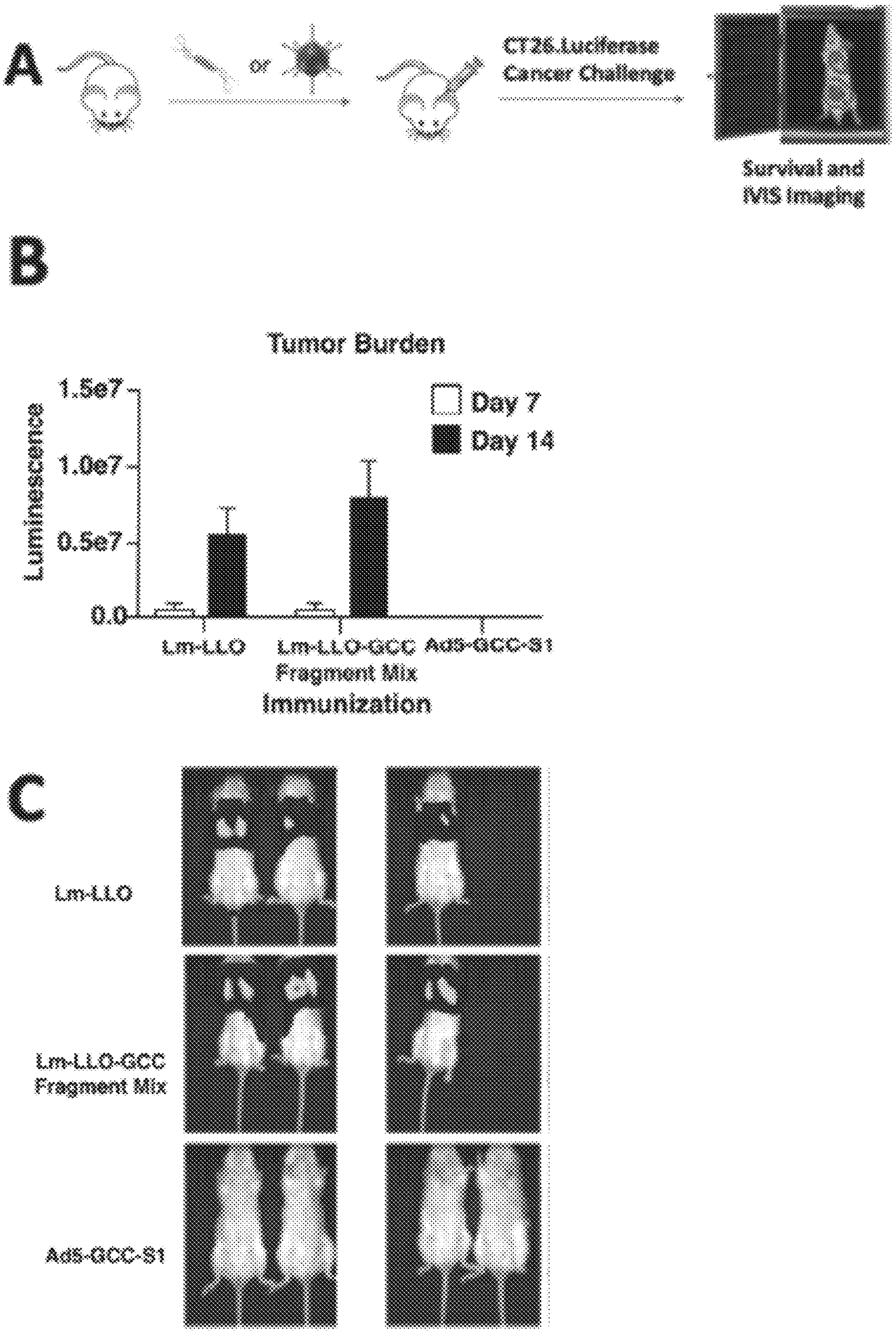
FIG. 20 panels A, B and C. Lm-LLO-GCC Antitumor Immunity. A-C) Wild-type BALB/c mice were immunized with a mixture of LmLLO-GCC fragments 1, 2, and 3 (@FIGS. 9-11). Mice received Lm-LLO lacking GCC as a negative control or Ad5-GCCS1 as a positive control. Mice (n=8 per group) were then challenged with CT26 colorectal cancer cells expressing GCC and luciferase. Tumor burden was imaged and quantified by whole-body bioluminescence imaging (BLI). B-C) Lm-LLOGCCC immunization showed no antitumor activity, while Ad5-GCC-S1 showed complete protection. C) Representative images from day 14.

2nd generation Lm-LLO-GCC vaccines containing GCC fragments were administered to Gcc−/− (FIG. 19 panel A) or Gcc+/+ (FIG. 19 panel B) mice. Because Gcc−/− mice produce only $CD4^+$ T-cell responses and Gcc+/+ produce only $CD8^+$ T-cell responses, mice received only the vaccine fragments containing those epitopes. Gcc−/− mice produced robust $CD4^+$ T-cell responses against GCC when immunized with the $CD4^+$ T-cell epitope containing fragments 1 and 2 (FIG. 19 panel A). However, Gcc+/+ mice failed to produce GCC-specific $CD8^+$ T-cell responses when immunized with the $CD8^+$ T-cell epitope-containing fragments 2 and 3 (FIG. 19 panel B). To confirm the lack of $CD8^+$ T-cell responses to GCC in Gcc+/+ mice, we performed an anti-tumor immunity experiment (FIG. 20 panels A-C). In agreement with IFNγ-ELISpot data (FIG. 19, panels A and B), Lm-LLO-GCC fragment immunization in Gcc+/+ mice showed no antitumor efficacy compared to Ad5-GCC-S1 which was 100% effective (FIG. 20 panels A, B and C).

2nd Generation Recombinant Lm-LLO-GCC Vaccines

Figure 21:
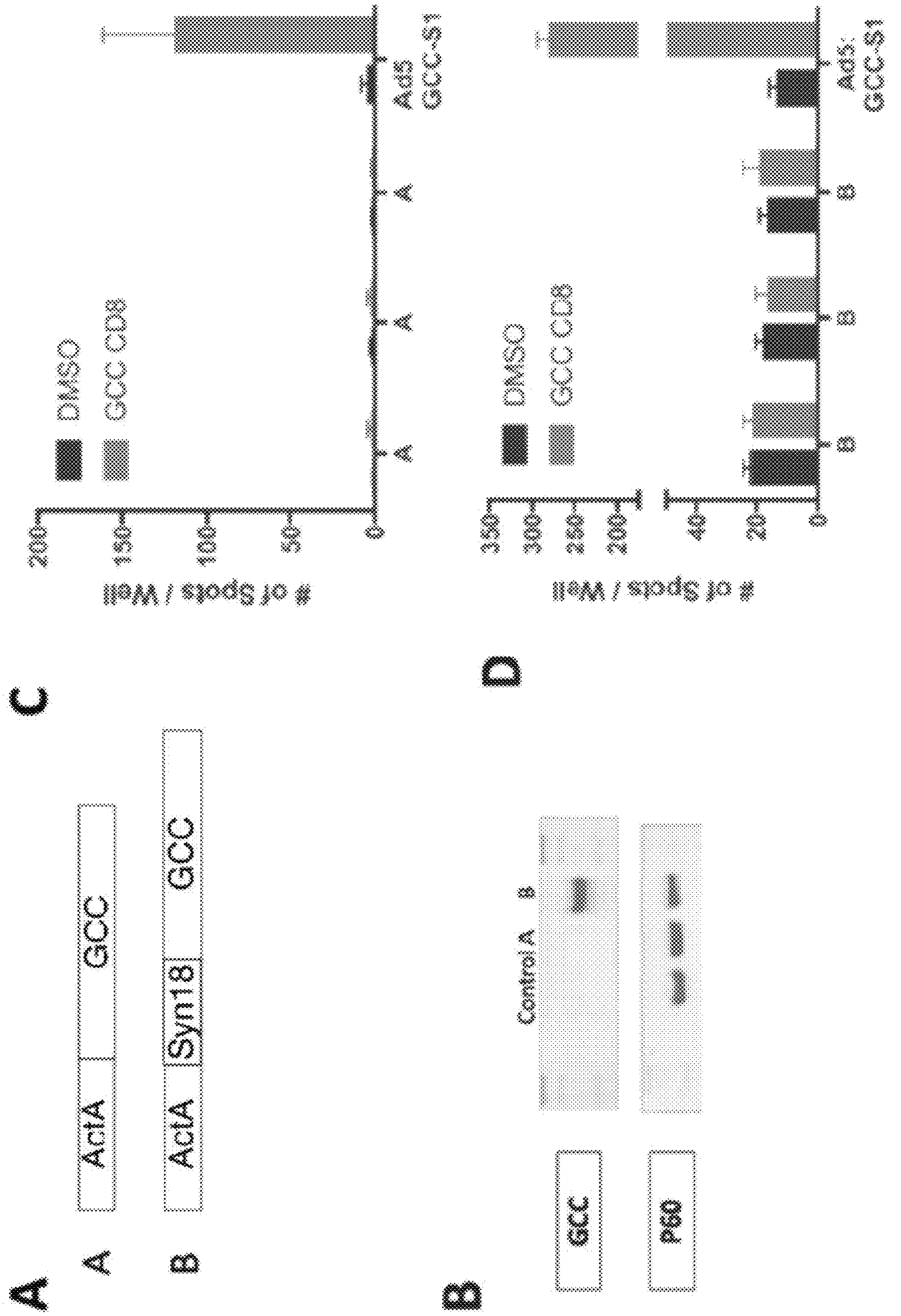
FIG. 21 panels A, B, C and D. Lm-ActA-GCC Vaccines. A) Two ActA-based GCC vaccines were produced, called Lm-ActA-GCC-A and Lm-ActA-GCC-B. These contain ActA fused to full-length GCC extracellular domain (residues 23-429). In addition, vaccine "B" contains a synthetic sequence (Syn18) to enhance Acta-GCC fusion protein production. B) Indeed, the presence of Syn18 significantly improves Acta-GCC production in macrophages infected with the various Lm vaccines in vitro. Anti-P60 detects an Lm protein, allowing for normalization of GCC expression levels in Lm-infected macrophages. Wild-type BALB/c mice were immunized with vaccine "A" (C) or "B" (D) or positive control Ad5-GCC-S1 and GCC-specific $CD8^+$ T-cell responses were measured by IFNγ-ELISpot. No responses were detected in the Lm-immunized groups. In C and D, individual mice are shown for vaccines "A" and "B".

In the context of poor Lm-LLO-GCC vaccine immunogenicity in mice receiving vaccines containing full-length GCC or fragments of GCC (FIGS. 14-20), we hypothesized that GCC may not be properly processed and presented in the context of LLO fusion proteins. Therefore, we produced recombinant Lm vaccines containing GCC fused to ActA, another Lm protein that is highly expressed in the cytosol of Lm-infected cells (FIG. 21 panel A). These vaccines induced GCC fusion protein production in Lm infected macrophages and expression was significantly enhanced by the inclusion of the Syn18 enhancer sequence (FIG. 21 panel B). However, the LmActA-GCC vaccines failed to induce GCC-specific $CD8^+$ T-cell responses in Gcc+/+ mice (FIG. 21 panels C-D).

Figure 22:
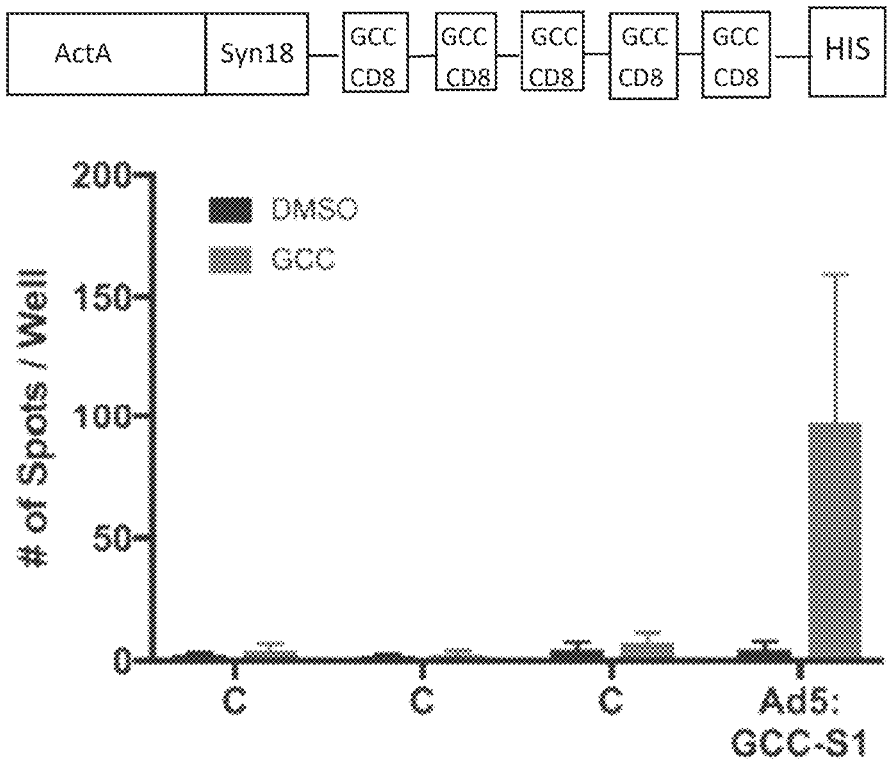
FIG. 22. Lm-ActA-GCC Multi-Epitope Vaccine. Recombinant Lm was produced containing ActA fused to 5 copies of the dominant GCC $CD8^+$ T-cell epitope in tandem (vaccine "C"), however, immunization of mice with this vaccine produced no GCC-specific $CD8^+$ T-cell response. Individual mice are shown for vaccine "C".

Next, we tried to enhance the GCC-specific $CD8^+$ T-cell responses by creating a novel construct containing 5 tandem repeats of the GCC $CD8^+$ T-cell epitope but lacking other domains of GCC (FIG. 22). These epitopes were fused to ActA and Syn18 to produce what we expected to be a highly immunogenic construct capable of inducing $CD8^+$ T-cell responses. However, immunization of wildtype BALB/c mice with this vaccine failed to generate any responses (FIG. 22).

Figure 23:
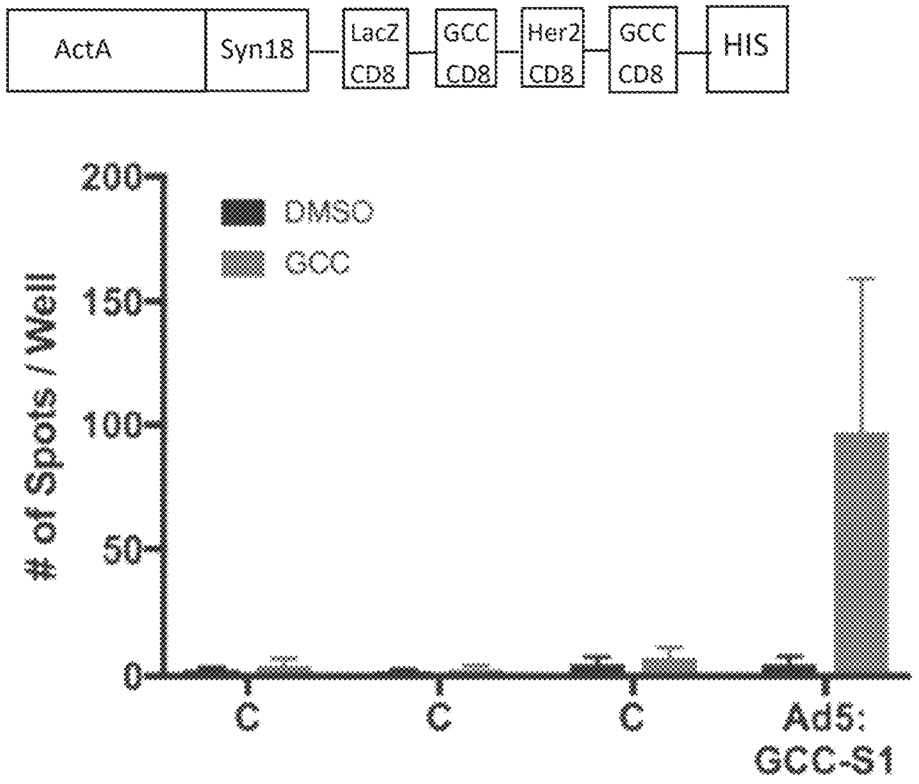
FIG. 23. Lm-ActA-Multi-Epitope Vaccine. Recombinant Lm was produced containing ActA fused to 4 tandem epitopes corresponding to the dominant $CD8^+$ T-cell epitopes from *E. coli* 0-galactosidase (LacZ), GCC, the mouse homolog of Her2, and Ad5 (vaccine "D"). Wild-type BALB/c mice were immunized, and responses were quantified by IFNγ-ELISpot.

Finally, we hypothesized that there may be something fundamentally flawed with our construct design and it cannot generate $CD8^+$ T-cell responses against any antigen. To test that hypothesis, we produced a novel construct containing ActA-Syn18 fused to the dominant $CD8^+$ T-cell epitope of GCC, as was well $CD8^+$ T-cell epitopes from *E. Coli* βgalactosidase (LacZ), mouse Her2, and Ad5 DNA-binding protein (DBP) (FIG. 23). While that vaccine produced robust responses against LacZ and Ad5, it failed to generate meaningful responses against GCC and Her2 (FIG. 23). Currently, we are generating new Lm constructs designed to enhance antigen processing and presentation of GCC $CD8^+$ T-cell epitopes.

We have designed and are currently producing several novel Lm constructs that we expect to result in increased GCC epitope presentation and generation of GCC-specific $CD8^+$ T-cell responses. Over the remaining project period, we will complete production of these vaccines and test their immunogenicity. Together, those studies and the completed work will establish the potential utility of Listeria-based vaccines targeting GCC for colorectal cancer immunotherapy.

Example 8

Colorectal cancer (CRC) is the second leading cause of cancer death and is the fourth most commonly diagnosed cancer in the United States. Moreover, the 5-year survival for patients with metastatic CRC is currently 14% and has remained relatively stagnant for decades, highlighting a lack of effective therapies for preventing and treating metastatic CRC. In this context, the intestinal receptor and tumor associated antigen guanylyl cyclase C (GUCY2C) has emerged as a developing immunotherapeutic option. A recent phase I study in CRC patients demonstrated immunogenicity and safety of an adenovirus-based vaccine against GUCY2C (Ad-GUCY2C) immunogenicity. However, optimal immunity against vaccine antigens are routinely achieved using a combinatorial approach with heterologous vaccine vectors, which help to evade limitations associated with vector-specific immunity and are often therefore superior to homologous vaccination using the same vector. Here, we constructed a recombinant strain of *Listeria monocytogenes* secreting GUCY2C (Lm-GUCY2C) and explored its immunogenicity in combination with Ad-GUCY2C to define an optimal GUCY2C vaccination regimen. We demonstrate that optimal GUCY2C and antitumor immunity is achieved utilizing a heterologous prime-boost immunization regimen in which Ad-GUCY2C is used to 'prime' a GUCY2C immune response and Lm-GUCY2C is used to 'boost' memory GUCY2C immune responses. We report that this combination leads to significant enhancements in the quantity of GUCY2C-specific CD8+ T cell counts as well as the avidity and polyfunctionality of the GUCY2C-specific CD8+ T cell pool. Moreover, we demonstrate that this immunization is safe, with histopathologic evaluation of vaccinated mice demonstrating no signs of toxicity. Collectively, these findings suggest that Lm-GUCY2C may be utilized to enhance GUCY2C immunity in patients with existing GUCY2C immune responses and may inform future GUCY2C-targeted vaccine clinical trials.

Materials and Methods

Vaccines

The chimeric replication-deficient adenovirus expressing mouse $GUCY2C_{1-429}$ fused to the influenza $HA_{107-119}$ CD4+ T-cell epitope known as site 1 (S1) was previously described (Ad5.F35-GUCY2C-S1). Ad5.F35-GUCY2C-S1 and Ad5.F35-GFP vaccines used in this study were produced by the Baylor College of Medicine in the Cell and Gene Therapy Vector Development Lab and certified to be negative for replication-competent adenovirus, mycoplasma, and host cell DNA contamination.

The attenuated Lm strain containing deletions in virulence factors internalin B and actA, LmΔactAΔinlB, was ordered from ATCC and serves as the parental strain for all Lm vaccines utilized in this study. Recombinant Lm-GUCY2C and Lm-LacZ was generated by synthesizing mouse GUCY2C extracellular $domain_{23-429}$ or $\beta$-$galactosidase_{618-1024}$ respectively in-frame with the first 100 amino acids of ActA protein under control of the actA promoter. The resulting sequence was cloned into the pPL2 integration vector and integrated into the Lm chromosome. Lm strains were grown in brain-heart infusion broth (Fisher Scientific) until $OD_{600}$ ~1, aliquoted, and stored at −80° C. On the day of experiment, aliquots were thawed, incubated at 37° C. for 60 minutes, washed 2× in PBS, and diluted to a desired concentration in PBS for vaccination.

In Vitro Infections

The mouse macrophage cell line J774A.1 was cultured in DMEM supplemented with 10% fetal bovine serum. J774A.1 cells were infected at a 10:1 multiplicity of infection with Lm-GUCY2C or control Lm. After a 1 h incubation, cells were washed 2× in PBS, resuspended in media containing 10 μg/mL gentamicin to eliminate free extracellular bacteria and incubated an additional 5 h. For immunofluorescence studies, Lm was labeled prior to infection by incubation with 2 mM CellTracker Red CMPTPX dye for 10 minutes at 37° C. For western blot studies, protein was extracted from cells using M-PER reagent (Pierce) supplemented with protease inhibitors. GUCY2C protein was stained using the anti-GUCY2C monoclonal antibody MS20 and p60 stained using the anti-p60 monoclonal antibody p6017 (AdipoGen).

Mice and Immunizations

Eight week-old male and female BALB/cJ mice were purchased from the Jackson Laboratory for experiments. Animal protocols were approved by the Thomas Jefferson University Institutional Animal Care and Use Committee (Protocol 01956). For adenovirus immunizations, mice received $10^{10}$ vp of Ad5.F35-GUCY2C-S1 or Ad5.F35-GFP as a control administered intramuscularly (i.m.) as two 50 uL injections, one in each hind limb. For Lm immunizations, $5\times10^6$ colony-forming units (CFU) of Lm-GUCY2C, empty Lm, or Lm-LacZ were administered intravenously (i.v.) as a 100 uL suspension in PBS. For ELISpot experiments empty Lm was used as a control and for tumor experiments Lm-LacZ was used for a control due to the ability of ActA protein to act as an adjuvant and augment anti-tumor response. For prime-boost immunizations, vaccines were delivered 21 d apart.

Ad5 Neutralizing Immunity Studies

Ad5 immunity was induced in BALB/cJ mice by intranasal exposure to $10^{10}$ Ad5-GFP. Twenty-eight days after infection, mice were bled, sera collected and immunized with $10^{11}$ vp of Ad5.F35-GUCY2C-S1 followed by $5\times10^6$ CFU of Lm-GUCY2C or control Lm 21 d later. Ad5 neutralizing antibody titers in mice were quantified as previously described.

IFN-γ ELISpot Assay

ELISpot assays were performed using a mouse interferon-γ (IFN-γ) single color ELISpot kit (Cellular Technology Limited) according to the manufacturer's protocol. Briefly, 96-well plates were coated with IFN-γ capture antibody at 4° C. After an overnight incubation, plates were washed with PBS and splenocytes from immunized mice plated in a 0.1% DMSO solution in CTL-TEST medium (Cellular Technology Limited) with or without 10 μg/mL $GUCY2C_{254-262}$ peptide and incubated at 37° C. for 24 hours. For TCR avidity studies, splenocytes were plated with various concentrations of $GUCY2C_{254-262}$ peptide (10 μg/mL to 3 pg/mL. The next day, cells were removed and development reagents were added to detect IFN-γ-producing spot-forming cells. The number of spot-forming cells per well was calculated using the SmartCount and Autogate functions of an ImmunoSpot S6 Universal Analyzer (Cellular Technology Limited). GUCY2C-specific responses were calculated by subtracting mean spots counts of 0.1% DMSO wells from peptide-pulsed wells.

Intracellular Cytokine Staining $10^6$ splenocytes from immunized mice were plated in a 96-well plate in the presence of DMSO or 10 ug/mL GUCY2C 254-262 peptide and anti-CD107-FITC (clone 1D4B). Cells were incubated at 37° C. for 1 h, protein transport inhibitor cocktail (eBioscience) was added and splenocytes were incubated an additional 5 hours at 37° C. Cells were stained with LIVE/DEAD Fixable Aqua Dead Cell Stain Kit (Invitrogen), anti-CD8PerCP-Cy5.5 (53-6.7; BD Biosciences), anti-CD19-BV510 (6D5; Biolegend). BD Cytofix/Cytoperm Kit (BD Biosciences) was used to permeabilize and intracellular cytokines stained using anti IFN-γ (XMG1.2; BD Biosciences) and anti-MIP1α-APC (39624: R&D Systems). Cells were fixed in 4% paraformaldehyde and analyzed on a BD LSR II flow cytometer. Analyses were performed using FlowJo software (TreeStar).

Tumor Studies

A GUCY2C and luciferase-expressing mouse (BALB/c) CT26 colorectal cancer cell line was generated as described previously and used for in vivo tumor studies. Six days after final immunization, mice received $5\times10^5$ CT26 cells via intravenous tail vein. Tumor burden was quantified weekly by subcutaneous injection of a 3.75 mg of D-luciferin potassium salt (Gold Biotechnologies) in PBS followed by an eight-minute incubation and imaged after ten-second exposure using a Caliper IVIS Lumina XR imaging station (PerkinElmer). Total radiance (photons/second) was measured using Living Image In Vivo Imaging Software (PerkinElmer).

Results

Lm-GUCY2C Vaccine Design

Figure 24:
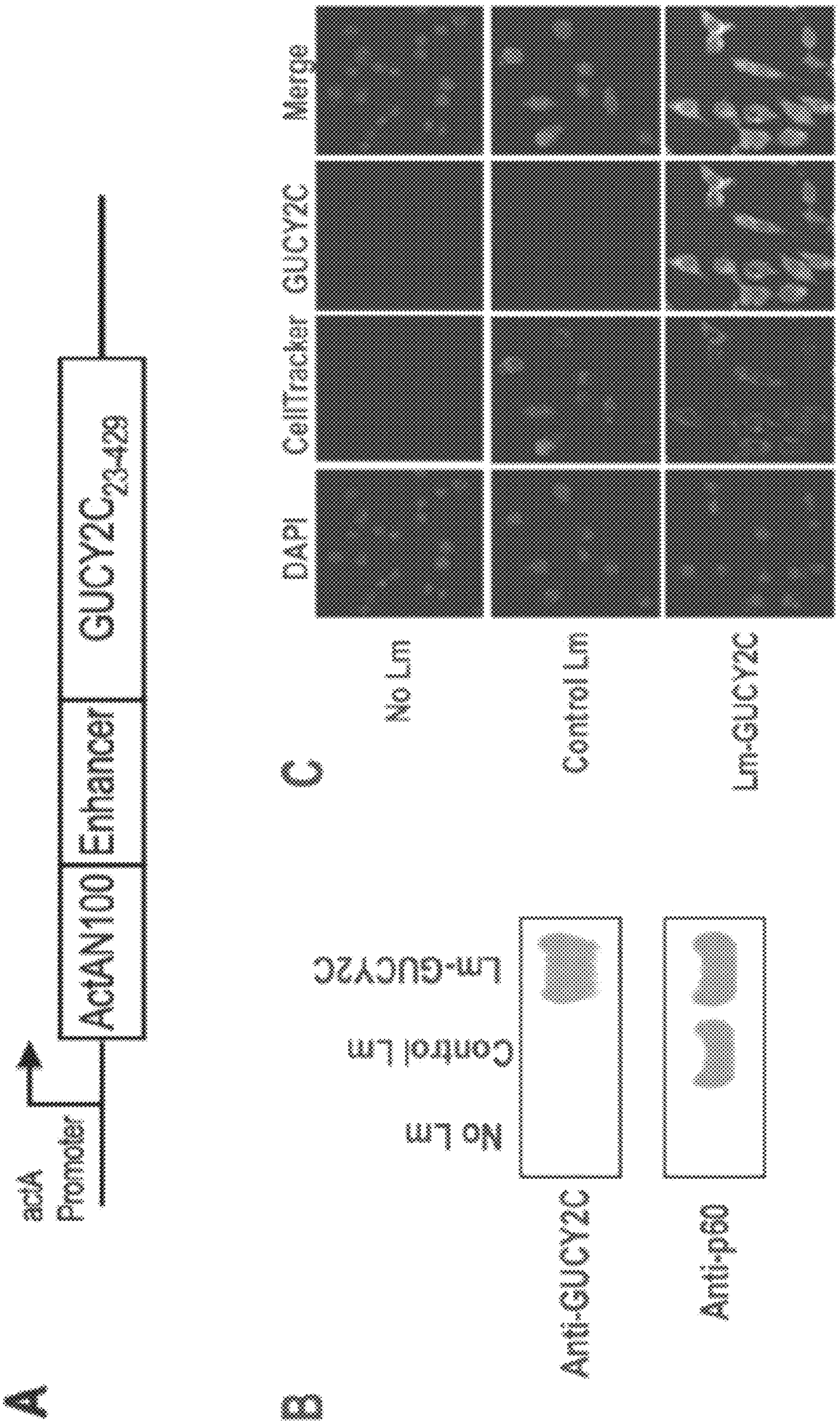
FIG. 24 panels A-C: Construction of Lm-GUCY2C. A) Lm-GUCY2C secretes a fusion protein comprised of ActAN100, an enhancer sequence, and mouse $GUCY2C_{23-429}$ under control of the acta promoter. B-C) The J774A.1 macrophage cell line was infected with Lm-GUCY2C or Lm-LacZ at a 10:1 MOI for 6 hours at 37° C. GUCY2C fusion protein was detected by (B) western blot and (C) immunofluorescence.

The extracellular domain of mouse $GUCY2C_{23-429}$ was codon optimized for *Listeria monocytogenes* using Java Codon Adaptation Tool and synthesized downstream of actA promoter, ActAN100, and an enhancer sequence as depicted in FIG. 24 panel A. The resulting sequence was cloned into the pPL2 integration vector and stably integrated into the genome of the live attenuated double-deleted strain Lm ΔactA ΔinlB. To confirm secretion of the ActA-GUCY2C fusion protein, the J774A.1 macrophage cell line was infected with Lm-GUCY2C or control Lm strain. Following a 6 hour incubation, macrophages were stained for GUCY2C protein expression by western blot (FIG. 24 panel B) and immunofluorescence (FIG. 24 panel C).

Figure 25:
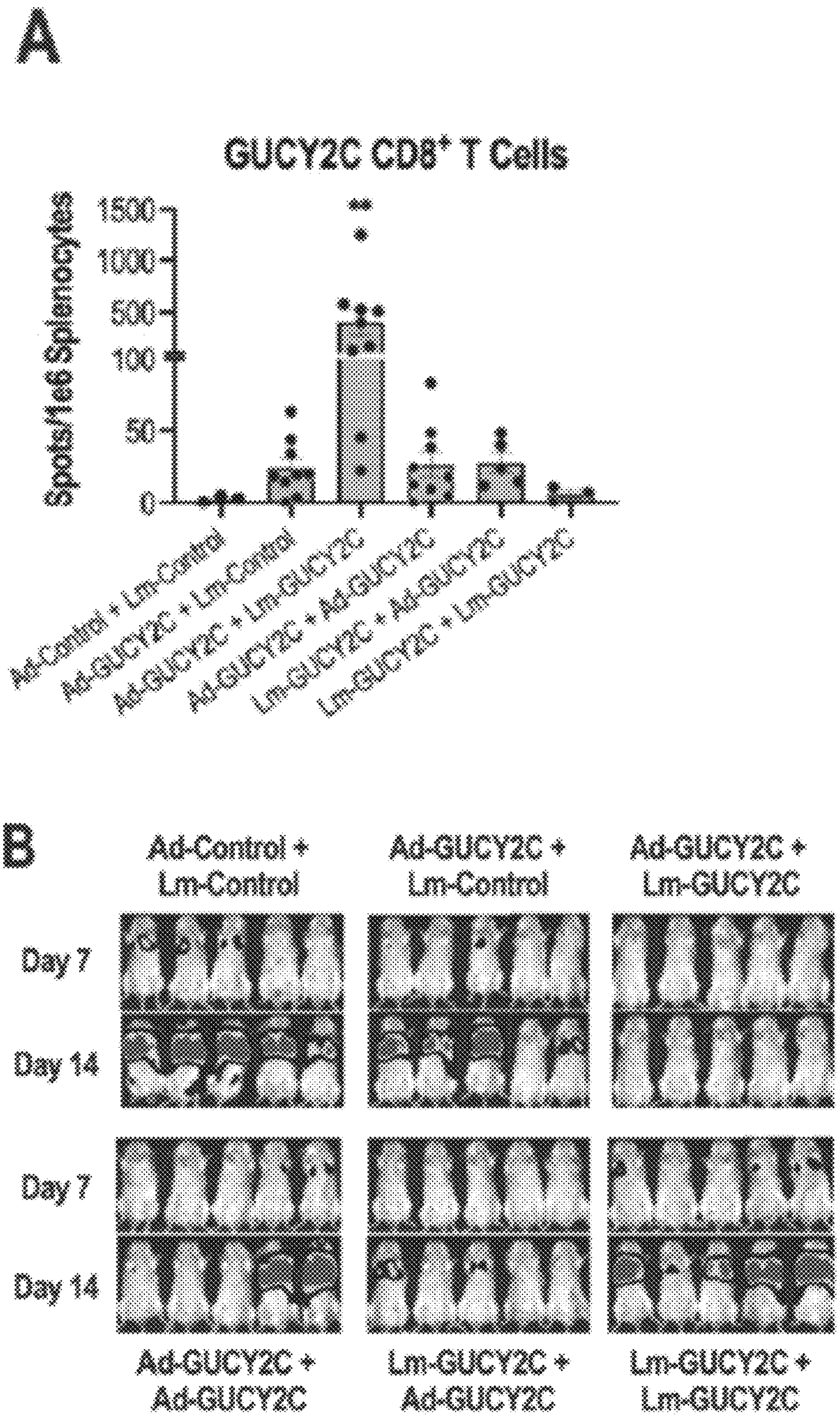
FIG. 25 panels A-D: Heterologous Ad5.F35-GUCY2C-S1+Lm-GUCY2C immunization enhances GUCY2C-specific $CD8^+$ T cell responses and antitumor immunity. (A-D) BALB/cJ mice (n=3-9/group) were immunized with a 'priming' immunization on day 0 and a 'boosting' immunization on day 21 utilizing homologous or heterologous combinations of GUCY2C-expressing and control vaccines. Adenovinis vaccines were administered intramuscularly (i.m.) as $10^{10}$ vp of Ad5.F35-GUCY2C-S1 or control Ad5.F35 and Lm vaccines were administered intravenously (i.v.) as $5\times10^6$ CFU of Lm-GUCY2C or control Lm. Six days after final immunization, mice were harvested and GUCY2C-specific $CD8^+$ T cells quantified by IFN-γ ELISpot (A) or challenged i.v. with $5\times10^5$ CT26 colorectal cancer cells expressing GUCY2C and firefly luciferase. On days 7 and 14 post-challenge, mice were injected with D-luciferin substrate and imaged (B). Tumor burden as quantified by luminescence (photons/second) upon imaging on ELISpot—day 7 was recorded (C). Survival was monitored throughout the experiment (D). GUCY2C-specific $CD8^+$ T cell responses and tumor-burden were analyzed by one-way ANOVA compared to control immunization and survival comparisons analyzed by the Mantel-Cox log-rank test.
Figure 25:
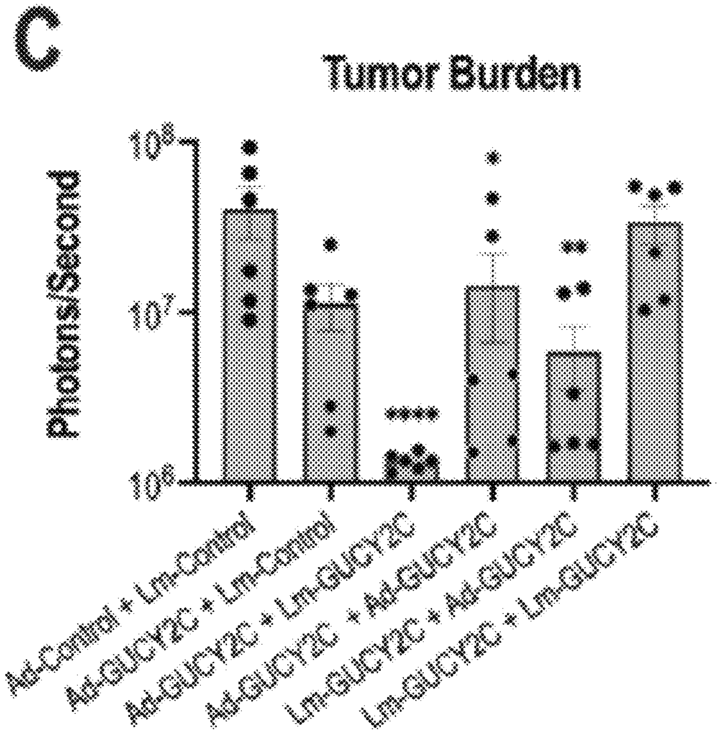
Figure 25:
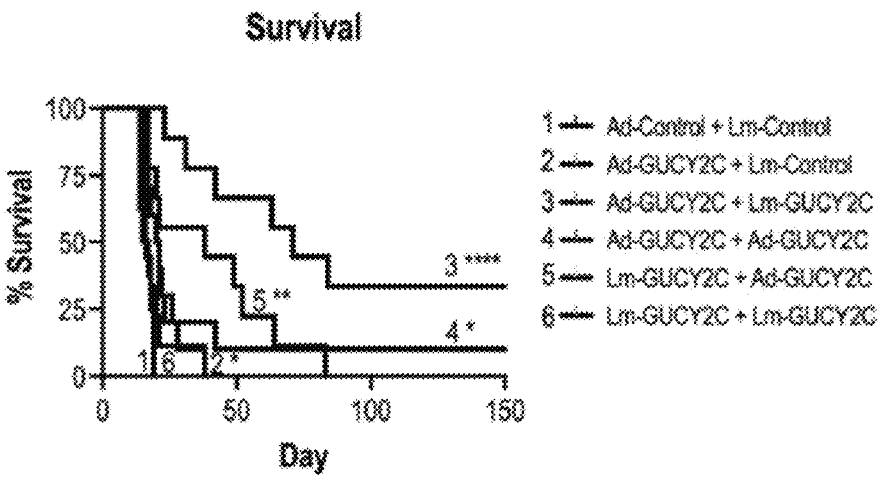

Heterologous Ad5.F35-GUCY2C-S1+Lm-GUCY2C Immunization Regimen Enhances GUCY2C-Specific CD8+ T Cell Responses and Antitumor Immunity Following in vitro confirmation of GUCY2C fusion protein expression by Lm-GUCY2C, we next sought to identify an optimal GUCY2C immunization regimen. Thus, Lm-GUCY2C vaccine was tested in combination with a chimeric adenovirus-based vaccine against GUCY2C (Ad5.F35-GUCY2C-S1) currently in phase II testing (NCT04111172). GUCY2C immunogenicity and antitumor immunity were evaluated utilizing a prime-boost strategy in which Lm-GUCY2C and Ad5.F35-GUCY2C-S1 vaccines were administered 21 days apart as homologous or heterologous vaccinations. Notably, the heterologous immunization regimen utilizing Ad5.F35-GUCY2C-S1 to 'prime' GUCY2C immune responses followed by Lm-GUCY2C to 'boost' generated significantly higher GUCY2C-specific $CD8^+$ T cell responses as quantified by IFN-Y ELISpot compared to all other immunization regimens (FIG. 25 panel A). Similarly, in the context of a colorectal tumor challenge, Ad5.F35-GUCY2C-S1+Lm-GUCY2C immunization significantly reduced metastatic tumor burden (FIG. 25 panel B and C), and increased median survival (FIG. 25 panel D) compared to other methods of vaccination. Importantly, the order of immunization, was essential for optimal GUCY2C immunity, with Ad5.F35-GUCY2C-S1+Lm-GUCY2C inducing a >15-fold increase in GUCY2C-specific $CD8^+$ T-cells ($p<0.0001$) and significantly improving median survival (71 d vs. 38 d, $p<0.05$) compared to Lm-GUCY2C+ Ad5.F35-GUCY2C-S1 vaccination. Moreover, we found that Lm-GUCY2C boosted GUCY2C immune responses 100 days after Ad5.F35-GUCY2C-S1 priming, suggesting Lm-GUCY2C could be boost GUCY2C memory responses long after an initial priming vaccination.

Figure 26:
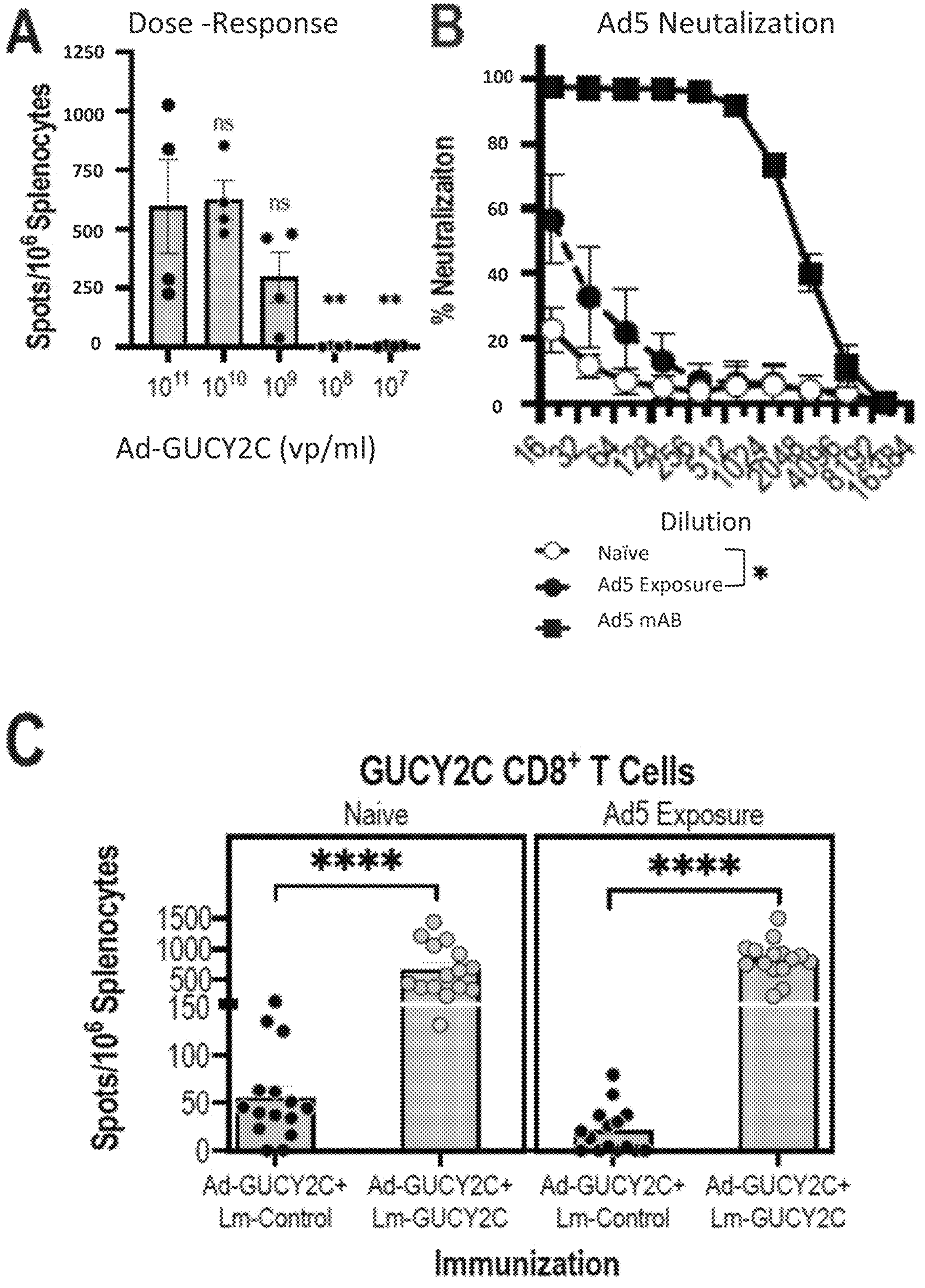
FIG. 26 panels A-C: Pre-existing Ad5 immunity does not impact Ad5.F35-GUCY2C-S1+Lm-GUCY2C immunization. (A) BALB/cJ (n=4/group) mice were immunized with decreasing doses ($10^{11}$ vp-$10^7$ vp) of Ad5.F35-GUCY2C-S1 vaccine on day 0 and boosted with $5\times10^6$ CFU of Lm-GUCY2C on day 21. Six days after final vaccination, GUCY2C-specific $CD8^+$ T cell responses were cells quantified by IFN-γ ELISpot. (B-E) BALB/cJ mice (n=15/group) were intranasally infected with $10^{10}$ vp of Ad5-GFP or PBS as a control on day 0. Twenty-eight days following vaccination, mice were bled and presence of Ad5-specific NAbs confirmed (B) prior to Ad5.F35-GUCY2C-S1 vaccination with $10^{11}$ vp. Twenty-one days after Ad5.F35-GUCY2C-S1 vaccination, mice were boosted with $5\times10^6$ CFU of Lm-GUCY2C or control Lan. Six days after final vaccination, five mice from each group were sacrificed to evaluate GUCY2C-specific $CD8^+$ T cell responses (C) and the remaining ten mice were challenged with $5\times10^5$ CT26 colorectal cancer cells expressing GUCY2C and firefly luciferase.

Impact of Vector-Specific Immunity on Ad5.F35-GUCY2C-S1+Lm-GUCY2C Immunization A known limitation of viral-based vaccines is the ability for vector-specific immunity to interfere with the immunogenicity of the target vaccine antigen. Specifically, neutralizing antibodies (NAbs) against the common adenovirus serotype 5 (Ad5) are detectable in >70% of healthy donors and have been demonstrated to blunt the efficacy of adenovirus-based vaccines. Although chimeric adenoviruses, such as Ad5.F35, are less susceptible to neutralization associated with Ad5 NAbs, the effect is modest and thus GUCY2C-specific immune responses of Ad5.F35-GUCY2C-S1 are partially reduced in the presence of prior Ad5 exposure. In contrast, Lm infection in humans does not results in NAbs against Lm and prior exposure does not limit the immunogenicity of the target vaccine antigen. Consistent with these observations, we found that prior Lm exposure did not limit GUCY2C immunogenicity of Lm-GUCY2C. Thus, we focused on the impact that prior Ad5 exposure may limit an Ad5.F35-GUCY2C-S1+Lm-GUCY2C vaccination approach. First, we wanted to define the ability of Lm-GUCY2C to boost at low priming doses of Ad5.F35-GUCY2C-S1 vaccine, which may be associated with antibody neutralization. Thus, we immunized mice with decreasing doses of Ad5.F35-GUCY2C-S1 and found that Lm-GUCY2C similarly boosted GUCY2C-specific $CD8^+$ T cells at doses ranging from $10^{11}$ vp to $10^9$ vp (FIG. 26 panel A). Next, we wanted to mimic Ad5 pre-existing immunity in vivo. To induce Ad5-specific immunity, mice were exposed intranasally to $10^{10}$ vp of Ad5-GFP or PBS twenty-eight days prior to the start of a Ad5.F35-GUCY2C-S1+Lm-GUCY2C vaccination regimen. As expected, Ad5-GFP exposure induced NAbs in mice at the time of vaccination (FIG. 26 panel B). However, Lm-GUCY2C boosted GUCY2C-specific $CD8^+$ T cell responses in naive mice and mice pre-exposed to Ad5-GFP (FIG. 26 panel C). Similarly, Lm-GUCY2C vaccination of naive and Ad5-GFP exposed mice similarly enhanced antitumor immunity as quantified by a reduced metastatic tumor burden (FIG. 26 panel D) and extended median survival (FIG. 26 panel E). Thus, Lm-GUCY2C may be effective at boosting GUCY2C-specific immunity in circumstances associated with a poor GUCY2C priming vaccination.

Figure 27:
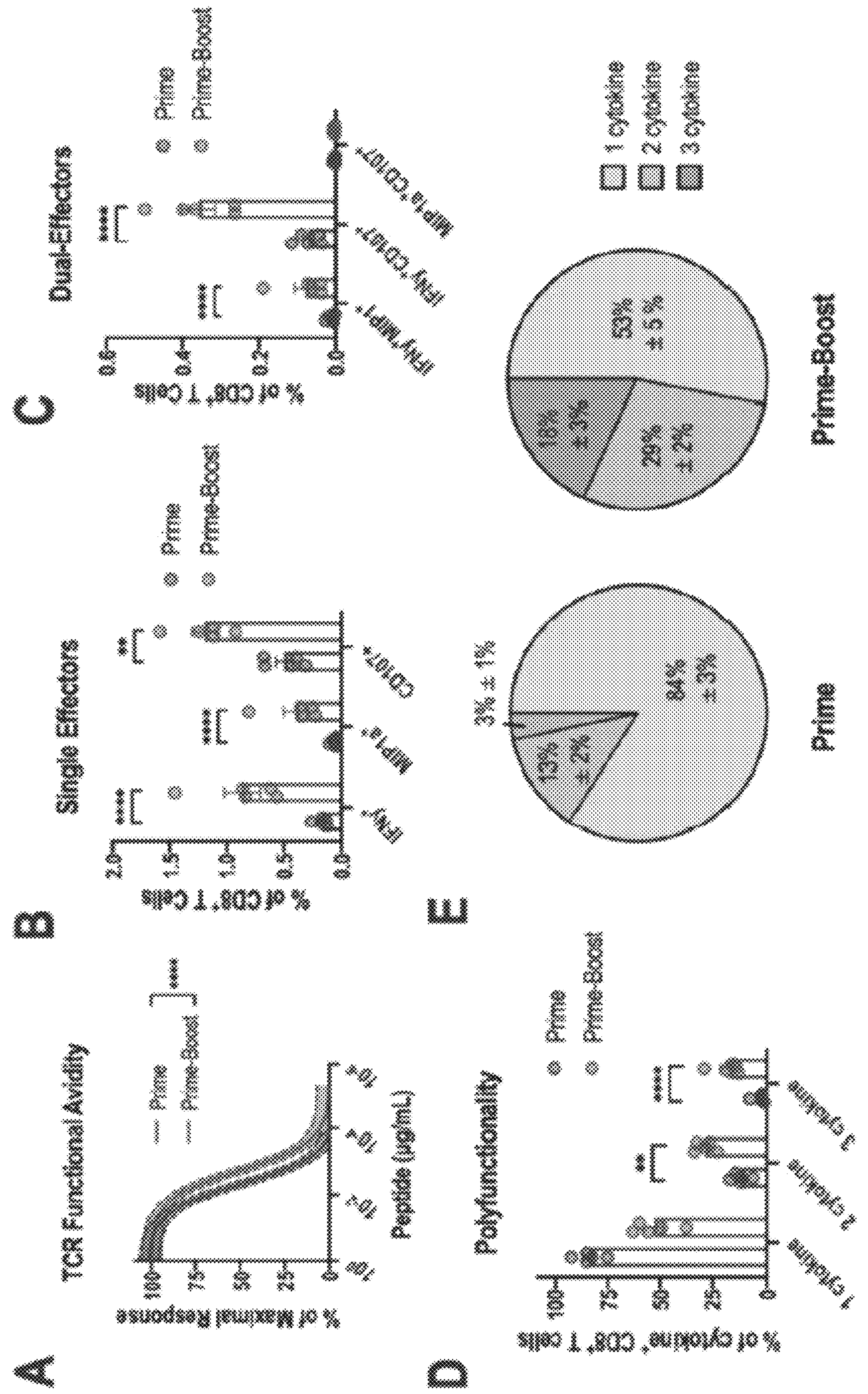
FIG. 27 panels A-E: Prime-boost enhances the avidity and polyfunctionality of the GUCY2C-specific CD8+ T cell pool BALB/cJ mice (n=5-8/group) were immunized using Ad5.F35-GUCY2C-S1 (prime) or Ad5.F35-GUCY2C-S1+Lm-GUCY2C (prime-boost) vaccination regimens. At the peak effector response, 14 days following prime and 6 days following prime-boost vaccination, splenocytes were collected with GUCY2C-specific CD8+ T cell avidity (A) quantified by IFN-γ ELISpot and polyfunctionality quantified by flow cytometry (B-E). (A) Non-linear regression (solid line) of GUCY2C-specific CD8+ T cell avidity is depicted with 95% confidence intervals (dashed lines). (B-E) The effector function of live, GUCY2C-specific CD8+ T cells by IFN-γ, MIP1α, and CD107a with (B) single-positive, and (C) double-positive events shown as a percentage of all CD8+ T cells. (D-E) Overall polyfunctionality of GUCY2C-specific CD8+ T cells shown as a percentage of cytokine+CD8+ T cells is depicted.

Qualitative Changes in the GUCY2C-Specific CD8+ T Cell Pool Following Prime-Boost Vaccination In addition to expanding the quantity of vaccine-specific T cells, previous studies have demonstrated that prime-boost immunizations impact the quality of vaccine-specific T cells. Thus, we wanted to determine the impact on the GUCY2C-specific $CD8^+$ T cell pool by comparing the avidity and polyfunctionality of GUCY2C-specific $CD8^+$ T cells at the peak effector response following Ad5.F35-GUCY2C-S1 priming and Ad5.F35-GUCY2C-S1+Lm-GUCY2C prime-boost vaccination. To assess the avidity of the GUCY2C-specific $CD8^+$ T cell pool, we pulsed splenocytes from immunized mice with decreasing concentrations of $GUCY2C_{254-262}$ peptide and quantified the IFN-γ response. Compared to mice immunized with a priming immunization alone, the EC50 of mice immunized with prime-boost was shifted ~2.5-fold (0.0046 μg/mL vs. 0018 μg/mL, $p<0.0001$), suggesting an enrichment of high avidity GUCY2C-specific T cells in mice following prime-boost (FIG. 27 panel A). Next, we used flow cytometry to assess the polyfunctionality of GUCY2C-specific $CD8^+$ T cells after prime and prime-boost vaccination. Consistent with ELISpot experiments, prime-boost significantly enhanced the IFN-γ response compared to priming immunization alone (FIG. 27 panel B), as well as the effector cytokine MIP1α and the surface marker of degranulation CD107a. Moreover, the percentage of double-positive (FIG. 27 panel C and E) and triple-positive (FIG. 27 panel D and E) $CD8^+$ T cells by IFN-γ, MIP1α, and CD107a staining was significantly elevated following prime-boost vaccination, suggesting prime-boost immunization produces GUCY2C-specific $CD8^+$ T cells with multiple effector functions. Thus, in addition to significantly amplifying GUCY2C-specific $CD8^+$ T cell counts, it is likely that enhanced antitumor immunity following Lm-GUCY2C boosting may be conferred via qualitative changes in the avidity and polyfunctionality of the GUCY2C-specific $CD8^+$ T cell pool.

Heterologous Prime-Boost Immunization does not Elicit Toxicity

Figure 28:
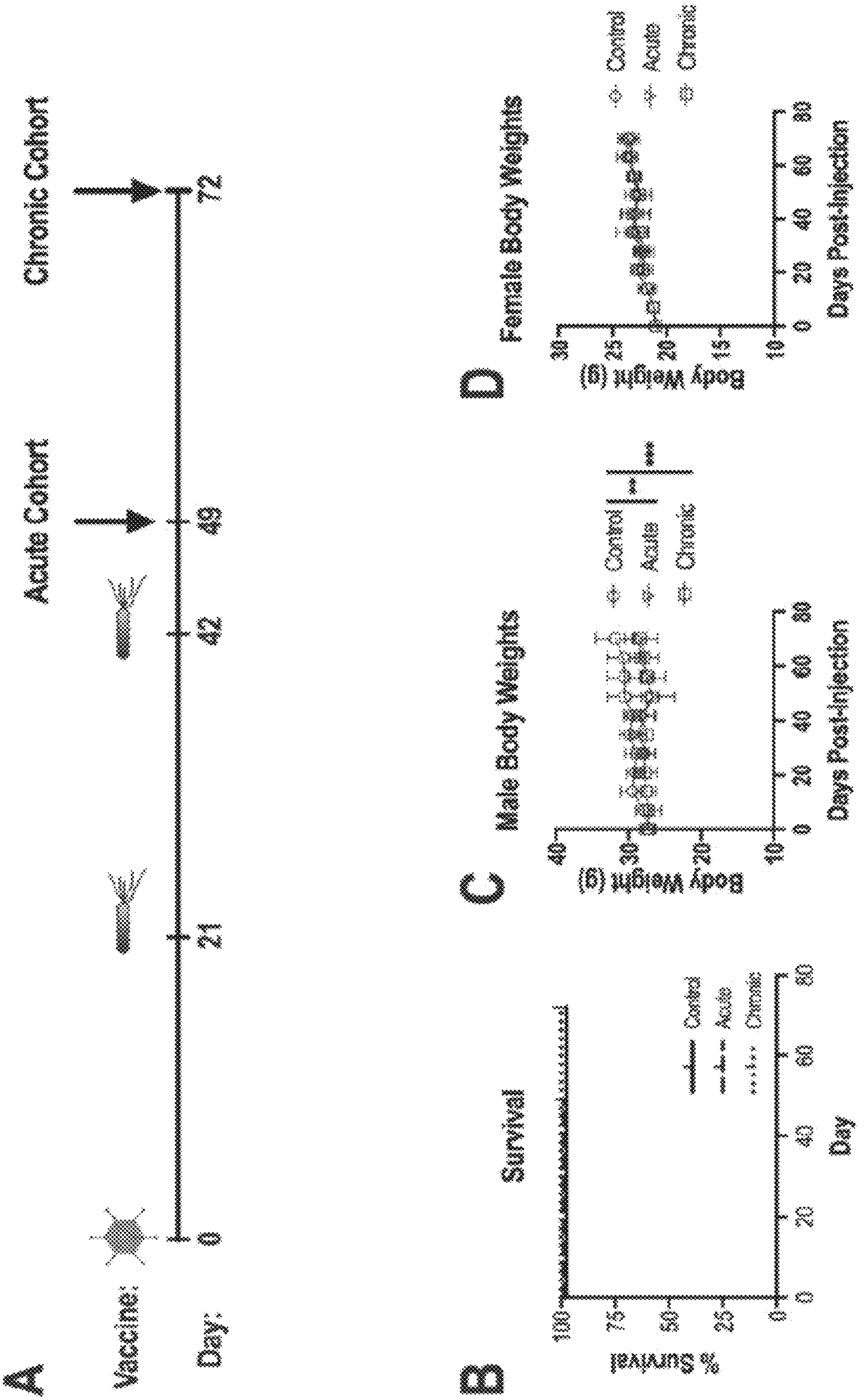
FIG. 28 panels A-D: Heterologous prime-boost immunization does not induce toxicity. (A) BALB/cJ mice (n=10/group) were immunized with Ad5.F35-GUCY2C-S1 on day 0 and Lm-GUCY2C on days 21 and 42 or PBS as a control on all days. (B-D) Survival and weights were monitored throughout the experiment.

Previously, we demonstrated the ability of GUCY2C vaccines to induce systemic anti-tumor immunity without invoking autoimmunity towards endogenous GUCY2C-expressing tissues. Given changes in the quantity, avidity, and polyfunctionality of the GUCY2C-specific $CD8^+$ T cell pool following Lm-GUCY2C-boosting, we wanted to characterize the safety of this immunization regimen. Thus, we employed two vaccination and assessment schedules to elucidate potential toxicity due to Ad5.F35-GUCY2C-S1+Lm-GUCY2C immunization. As depicted in FIG. 28 panel A, mice were immunized with $10^{10}$ vp Ad5.F35-GUCY2C-S1 on day 0, followed by two additional immunizations of $5\times10^{6}$ CFU Lm-GUCY2C on day 21 and day 42. Seven and thirty days following final immunization, mice were sacrificed and organs harvested for assessment of acute and/or chronic toxicity respectively. An additional cohort received PBS on all immunization days. No signs of toxicity in acute or chronic cohorts were observed during in-life observations or survival (FIG. 28 panel B). Notably, male but not female mice in acute and chronic cohorts had decreased body weights throughout the study compared to the control cohort (FIG. 28 panel C and D). Similarly, statistically significant decreases in brain and small intestine organ weights were noted exclusively in male mice of the acute and/or chronic cohorts, possibly due to differences in general body size. Interestingly, female mice were in acute and chronic cohorts exhibited decreased stomach weights. Additionally, mice in the acute cohort most recently immunized with Lm-GUCY2C exhibited splenomegaly, consistent with prior studies and likely due to Lm tropism for the spleen. Collectively, no differences in organ weights were maintained in groups across sex, except for splenomegaly. Despite minor differences in organ size, histopathologic scoring by a blinded pathologist revealed no differences in inflammation among known GUCY2C-expressing tissues (small intestine, colon, brain) and GUCY2C-devoid tissues (salivary gland, stomach, heart, lung, kidney, and liver). Increased inflammation in spleen was noted in the acute cohort, consistent with splenomegaly findings. Together, these data suggest Ad5.F35-GUCY2C-S1+Lm-GUCY2C immunization enhances GUCY2C immunity without generating autoimmunity against endogenous GUCY2C-expressing tissues, consistent with prior studies.

Discussion

A major limitation in CRC management remains the likelihood of disease recurrence following surgical resection and the ineffectiveness of current therapies to treat metastatic disease, particularly for patients with microsatellite-stable and mismatch repair proficient tumors. In these settings, vaccination may be an ideal therapeutic by eliminating CRC cells that have escaped conventional treatment as well as conferring long-term immunity, thereby protecting against future recurrence. Here, we define an optimal GUCY2C immunization regimen utilizing a heterologous combination of vaccine vectors that is immunogenic and induces potent antitumor immunity without causing autoimmunity.

Consistent with prior studies, we find that prime-boost vaccination not only elevates the quantity of vaccine-specific T cells, but also significantly impacts the quality of the vaccine-specific T cell pool. We report that GUCY2C-specific $CD8^+$ T cell pool following Lm-GUCY2C boost are is of higher avidity and exhibits increased effector function. Notably, multiple studies have demonstrated that higher avidity TCRs as well as polyfunctional T cells may be more effective eliminating cancer cells and clearing viral infections possible. Therefore, it is that additional antitumor immunity conferred by Lm-GUCY2C boost may be through a combination of all three factors.

Adenovirus-based cancer vaccines have in part been hindered by the high proportion of individuals with Ad5-specific NAbs that block reinfection and therefore limit vaccine efficacy upon immunization. While the use of rare serotype and chimeric adenoviral vectors, such as Ad5.F35, are less susceptible to neutralization associated with Ad5 pre-existing immunity, the induction of vector-specific NAbs upon vaccination limit the utility of additional immunizations. Thus, heterologous immunizations utilizing two different vectors may be preferable to homologous immunization in this setting. Moreover, in contrast to viral vectors, bacterial vectors such as Lm do not induce NAbs upon vaccination. Thus, as GUCY2C immunity wanes over time, repeated vaccinations with Lm-GUCY2C are permissible and may be necessary in patients to consistently elevate GUCY2C immunity to therapeutic levels.

While Lm-GUCY2C induced potent expansion of memory GUCY2C-specific $CD8^+$ T cell cells following Ad5.F35-GUCY2C-S1 priming, Lm-GUCY2C alone was poorly effective as a single-agent therapy. Indeed, homologous Lm-GUCY2C vaccination generated a notable absence of GUCY2C-specific $CD8^+$ T cells by ELISpot and conferred no protection against CRC challenge. Interestingly, studies exploring Lm vaccines as single-agent therapies have reported mixed success. Lm vaccines against the tumor antigens HER2 and PSA generate potent antitumor immunity as monotherapies while Lm vaccines against other tumor antigens including PAP and mesothelin similarly demonstrated limited immunogenicity alone and were utilized as heterologous prime-boost immunizations. Additionally, enhanced antitumor immunity combining Lm vaccines with immune modulators such as ani-GITR and anti-PD-1 antibodies have been reported. Thus, additional investigation into understanding why Lm-GUCY2C does not prime detectable GUCY2C immune responses alone and pairing immune modulators with Lm-GUCY2C may yield important insights into Lm-GUCY2C biology and lead to further enhancements in GUCY2C immunity.

In the context of an ongoing clinical trial testing an Ad5.F35-GUCY2C-PADRE vaccine in gastrointestinal cancers (NCT04111172), these studies suggest that patients enrolled in this trial may benefit from additional vaccination with Lm-GUCY2C. Our studies demonstrate that Ad5.F35-GUCY2C-S1+Lm-GUCY2C induces superior GUCY2C antitumor immunity and CD8+ T cell expansion compared to homologous immunization with either vector. Moreover, our studies suggest that Lm-GUCY2C boosting can be efficacious long after initial priming with Ad5.F35-GUCY2C-S1 immunization, suggesting patients may be benefit from Lm-GUCY2C boosting despite long intervals between initial priming immunization.

What is claimed is:

1. A recombinant Ad5.F35 adenovirus comprising:
   a) an adenoviral Ad5.F35 vector which is replication defective and further comprising:
   b) a gene expression cassette comprising:
      i) a heterologous promoter operatively linked to,
      ii) a nucleic acid encoding a soluble human GUCY2C domain as set forth in SEQ ID NO: 5 fused in frame to,
      iii) a nucleic acid encoding a universal CD4+ helper epitope PADRE.

2. The recombinant Ad5.F35 adenovirus of claim 1 wherein the PADRE is encoded by SEQ ID NO: 7.

3. A recombinant Ad5.F35 adenovirus of claim 1 comprising:
   a) an adenoviral Ad5.F35 vector which is replication defective and further comprising:
   b) a gene expression cassette comprising:
      i) a heterologous promoter operatively linked to,
      ii) a nucleic acid encoding a soluble human GUCY2C domain fused in frame to,
      iii) a nucleic acid encoding a universal CD4+ helper epitope, wherein the gene expression cassette comprises SEQ ID NO:9.

4. An injectable pharmaceutical composition comprising an adenovirus of claim 3 and a pharmaceutically acceptable carrier or diluent.

5. A method of treating a human patient diagnosed with cancer, wherein cells of said cancer express GUCY2C, the method comprising the steps of
   a) administering to the patient an effective amount of an injectable pharmaceutical composition comprising
      i) a replication defective recombinant Ad5.F35 adenovirus comprising:
         an adenoviral Ad5.F35 vector further comprising:
         a gene expression cassette comprising:
            a heterologous promoter operatively linked to,
            a nucleic acid encoding a soluble human GUCY2C domain that comprises SEQ ID NO: 5 fused in frame to,
            a nucleic acid encoding a universal CD4+ helper epitope;

and
   b) subsequently administering to the patient an effective amount of an injectable pharmaceutical composition comprising
      i) a recombinant *Listeria monocytogenes* comprising:
         a gene expression cassette comprising
            a heterologous promoter operatively linked to
            a nucleic acid encoding a soluble human GUCY2C domain.

6. The method of claim 5 wherein:
   the nucleic acid encoding the universal CD4+ helper epitope of the gene expression cassette of the recombinant Ad5.F35 adenovirus comprises a nucleic acid encoding the universal CD4+ helper epitope PADRE.

7. The method of claim 6 wherein:
   the nucleic acid encoding universal CD4+ helper epitope PADRE of the gene expression cassette of the recombinant Ad5.F35 adenovirus comprises SEQ ID NO: 7.

8. A method of treating a human patient diagnosed with cancer, wherein cells of said cancer express GUCY2C, the method comprising the steps of
   a) administering to the patient an effective amount of an injectable pharmaceutical composition comprising
      i) a replication defective recombinant Ad5.F35 adenovirus comprising:
         an adenoviral Ad5.F35 vector further comprising:
         a gene expression cassette comprising:
            a heterologous promoter operatively linked to,
            a nucleic acid encoding a soluble human GUCY2C domain fused in frame to,
            a nucleic acid encoding a universal CD4+helper epitope,
         wherein the gene expression cassette of the recombinant Ad5.F35 adenovirus comprises SEQ ID NO:9;

and
   b) subsequently administering to the patient an effective amount of an injectable pharmaceutical composition comprising
      i) a recombinant *Listeria monocytogenes* comprising:
         a gene expression cassette comprising
            a heterologous promoter operatively linked to
            a nucleic acid encoding a soluble human GUCY2C domain.

9. The method of claim 8 wherein the recombinant *Listeria monocytogenes* comprises a nucleic acid encoding a soluble human GUCY2C domain fused to a *Listeria monocytogenes* protein ActA.

10. The method of claim 5 wherein the recombinant *Listeria monocytogenes* comprises a nucleic acid encoding a soluble human GUCY2C domain fused to *Listeria monocytogenes* protein ActA.

11. The method of claim 5 wherein-prior to administering to the patient the injectable pharmaceutical composition that comprises the recombinant Ad5.F35 adenovirus, a sample of cancer tissue is analyzed to determine whether the cancer tissue expresses GUCY2C.

12. The method of claim 5 wherein the cancer expressing GUCY2C is esophageal, gastric, pancreatic, or colorectal.

13. The method of claim 5 wherein the cancer is metastatic.

14. The method of claim 8 wherein-prior to administering to the patient the injectable pharmaceutical composition that comprises the recombinant Ad5.F35 adenovirus, a sample of cancer tissue is analyzed to determine whether the cancer tissue expresses GUCY2C.

15. The method of claim 8 wherein the cancer expressing GUCY2C is esophageal, gastric, pancreatic, or colorectal.

16. The method of claim 8 wherein the cancer is metastatic.

* * * * *

SEQUENCE LISTING

```
<160> NUMBER OF SEQ ID NOS: 43

<210> SEQ ID NO 1
<211> LENGTH: 3787
<212> TYPE: DNA
<213> ORGANISM: Homo sapiens
<220> FEATURE:
<221> NAME/KEY: CDS
<222> LOCATION: (118)..(3339)

<400> SEQUENCE: 1

tggagtgggc tgagggactc cactagaggc tgtccatctg gattccctgc ctccctagga      60

gcccaacaga gcaaagcaag tgggcacaag gagtatggtt ctaacgtgat tggggtc        117

atg aag acg ttg ctg ttg gac ttg gct ttg tgg tca ctg ctc ttc cag       165
Met Lys Thr Leu Leu Leu Asp Leu Ala Leu Trp Ser Leu Leu Phe Gln
1               5                   10                  15

ccc ggg tgg ctg tcc ttt agt tcc cag gtg agt cag aac tgc cac aat       213
Pro Gly Trp Leu Ser Phe Ser Ser Gln Val Ser Gln Asn Cys His Asn
            20                  25                  30

ggc agc tat gaa atc agc gtc ctg atg atg ggc aac tca gcc ttt gca       261
Gly Ser Tyr Glu Ile Ser Val Leu Met Met Gly Asn Ser Ala Phe Ala
        35                  40                  45

gag ccc ctg aaa aac ttg gaa gat gcg gtg aat gag ggg ctg gaa ata       309
Glu Pro Leu Lys Asn Leu Glu Asp Ala Val Asn Glu Gly Leu Glu Ile
    50                  55                  60

gtg aga gga cgt ctg caa aat gct ggc cta aat gtg act gtg aac gct       357
Val Arg Gly Arg Leu Gln Asn Ala Gly Leu Asn Val Thr Val Asn Ala
65                  70                  75                  80

act ttc atg tat tcg gat ggt ctg att cat aac tca ggc gac tgc cgg       405
Thr Phe Met Tyr Ser Asp Gly Leu Ile His Asn Ser Gly Asp Cys Arg
                85                  90                  95

agt agc acc tgt gaa ggc ctc gac cta ctc agg aaa att tca aat gca       453
Ser Ser Thr Cys Glu Gly Leu Asp Leu Leu Arg Lys Ile Ser Asn Ala
            100                 105                 110

caa cgg atg ggc tgt gtc ctc ata ggg ccc tca tgt aca tac tcc acc       501
Gln Arg Met Gly Cys Val Leu Ile Gly Pro Ser Cys Thr Tyr Ser Thr
        115                 120                 125

ttc cag atg tac ctt gac aca gaa ttg agc tac ccc atg atc tca gct       549
Phe Gln Met Tyr Leu Asp Thr Glu Leu Ser Tyr Pro Met Ile Ser Ala
    130                 135                 140

gga agt ttt gga ttg tca tgt gac tat aaa gaa acc tta acc agg ctg       597
Gly Ser Phe Gly Leu Ser Cys Asp Tyr Lys Glu Thr Leu Thr Arg Leu
145                 150                 155                 160

atg tct cca gct aga aag ttg atg tac ttc ttg gtt aac ttt tgg aaa       645
Met Ser Pro Ala Arg Lys Leu Met Tyr Phe Leu Val Asn Phe Trp Lys
                165                 170                 175

acc aac gat ctg ccc ttc aaa act tat tcc tgg agc act tcg tat gtt       693
Thr Asn Asp Leu Pro Phe Lys Thr Tyr Ser Trp Ser Thr Ser Tyr Val
            180                 185                 190

tac aag aat ggt aca gaa act gag gac tgt ttc tgg tac ctt aat gct       741
Tyr Lys Asn Gly Thr Glu Thr Glu Asp Cys Phe Trp Tyr Leu Asn Ala
        195                 200                 205

ctg gag gct agc gtt tcc tat ttc tcc cac gaa ctc ggc ttt aag gtg       789
Leu Glu Ala Ser Val Ser Tyr Phe Ser His Glu Leu Gly Phe Lys Val
    210                 215                 220
```

```
gtg tta aga caa gat aag gag ttt cag gat atc tta atg gac cac aac      837
Val Leu Arg Gln Asp Lys Glu Phe Gln Asp Ile Leu Met Asp His Asn
225                 230                 235                 240

agg aaa agc aat gtg att att atg tgt ggt ggt cca gag ttc ctc tac      885
Arg Lys Ser Asn Val Ile Ile Met Cys Gly Gly Pro Glu Phe Leu Tyr
                245                 250                 255

aag ctg aag ggt gac cga gca gtg gct gaa gac att gtc att att cta      933
Lys Leu Lys Gly Asp Arg Ala Val Ala Glu Asp Ile Val Ile Ile Leu
            260                 265                 270

gtg gat ctt ttc aat gac cag tac ttg gag gac aat gtc aca gcc cct      981
Val Asp Leu Phe Asn Asp Gln Tyr Leu Glu Asp Asn Val Thr Ala Pro
        275                 280                 285

gac tat atg aaa aat gtc ctt gtt ctg acg ctg tct cct ggg aat tcc     1029
Asp Tyr Met Lys Asn Val Leu Val Leu Thr Leu Ser Pro Gly Asn Ser
    290                 295                 300

ctt cta aat agc tct ttc tcc agg aat cta tca cca aca aaa cga gac     1077
Leu Leu Asn Ser Ser Phe Ser Arg Asn Leu Ser Pro Thr Lys Arg Asp
305                 310                 315                 320

ttt cgt ctt gcc tat ttg aat gga atc ctc gtc ttt gga cat atg ctg     1125
Phe Arg Leu Ala Tyr Leu Asn Gly Ile Leu Val Phe Gly His Met Leu
                325                 330                 335

aag ata ttt ctt gaa aat gga gaa aat att acc acc ccc aaa ttt gct     1173
Lys Ile Phe Leu Glu Asn Gly Glu Asn Ile Thr Thr Pro Lys Phe Ala
            340                 345                 350

cat gcc ttc agg aat ctc act ttt gaa ggg tat gac ggt cca gtg acc     1221
His Ala Phe Arg Asn Leu Thr Phe Glu Gly Tyr Asp Gly Pro Val Thr
        355                 360                 365

ttg gat gac tgg ggg gat gtt gac agt acc atg gtg ctt ctg tat acc     1269
Leu Asp Asp Trp Gly Asp Val Asp Ser Thr Met Val Leu Leu Tyr Thr
    370                 375                 380

tct gtg gac acc aag aaa tac aag gtt ctt ttg acc tat gat acc cac     1317
Ser Val Asp Thr Lys Lys Tyr Lys Val Leu Leu Thr Tyr Asp Thr His
385                 390                 395                 400

gta aat aag acc tat cct gtg gat atg agc ccc aca ttc act tgg aag     1365
Val Asn Lys Thr Tyr Pro Val Asp Met Ser Pro Thr Phe Thr Trp Lys
                405                 410                 415

aac tct aaa ctt cct aat gat att aca ggc cgg ggc cct cag atc ctg     1413
Asn Ser Lys Leu Pro Asn Asp Ile Thr Gly Arg Gly Pro Gln Ile Leu
            420                 425                 430

atg att gca gtc ttc acc ctc act gga gct gtg gtg ctg ctc ctg ctc     1461
Met Ile Ala Val Phe Thr Leu Thr Gly Ala Val Val Leu Leu Leu Leu
        435                 440                 445

gtc gct ctc ctg atg ctc aga aaa tat aga aaa gat tat gaa ctt cgt     1509
Val Ala Leu Leu Met Leu Arg Lys Tyr Arg Lys Asp Tyr Glu Leu Arg
    450                 455                 460

cag aaa aaa tgg tcc cac att cct cct gaa aat atc ttt cct ctg gag     1557
Gln Lys Lys Trp Ser His Ile Pro Pro Glu Asn Ile Phe Pro Leu Glu
465                 470                 475                 480

acc aat gag acc aat cat gtt agc ctc aag atc gat gat gac aaa aga     1605
Thr Asn Glu Thr Asn His Val Ser Leu Lys Ile Asp Asp Asp Lys Arg
                485                 490                 495

cga gat aca atc cag aga cta cga cag tgc aaa tac gtc aaa aag cga     1653
Arg Asp Thr Ile Gln Arg Leu Arg Gln Cys Lys Tyr Val Lys Lys Arg
            500                 505                 510

gtg att ctc aaa gat ctc aag cac aat gat ggt aat ttc act gaa aaa     1701
Val Ile Leu Lys Asp Leu Lys His Asn Asp Gly Asn Phe Thr Glu Lys
        515                 520                 525

cag aag ata gaa ttg aac aag ttg ctt cag att gac tat tac acc cta     1749
Gln Lys Ile Glu Leu Asn Lys Leu Leu Gln Ile Asp Tyr Tyr Thr Leu
```

```
    530                 535                 540

acc aag ttc tac ggg aca gtg aaa ctg gat acc atg atc ttc ggg gtg      1797
Thr Lys Phe Tyr Gly Thr Val Lys Leu Asp Thr Met Ile Phe Gly Val
545                 550                 555                 560

ata gaa tac tgt gag aga gga tcc ctc cgg gaa gtt tta aat gac aca      1845
Ile Glu Tyr Cys Glu Arg Gly Ser Leu Arg Glu Val Leu Asn Asp Thr
                565                 570                 575

att tcc tac cct gat ggc aca ttc atg gat tgg gag ttt aag atc tct      1893
Ile Ser Tyr Pro Asp Gly Thr Phe Met Asp Trp Glu Phe Lys Ile Ser
            580                 585                 590

gtc ttg tat gac att gct aag gga atg tca tat ctg cac tcc agt aag      1941
Val Leu Tyr Asp Ile Ala Lys Gly Met Ser Tyr Leu His Ser Ser Lys
        595                 600                 605

aca gaa gtc cat ggt cgt ctg aaa tct acc aac tgc gta gtg gac agt      1989
Thr Glu Val His Gly Arg Leu Lys Ser Thr Asn Cys Val Val Asp Ser
    610                 615                 620

aga atg gtg gtg aag atc act gat ttt ggc tgc aat tcc att ttg cct      2037
Arg Met Val Val Lys Ile Thr Asp Phe Gly Cys Asn Ser Ile Leu Pro
625                 630                 635                 640

cca aaa aag gac ctg tgg aca gct cca gag cac ctc cgc caa gcc aac      2085
Pro Lys Lys Asp Leu Trp Thr Ala Pro Glu His Leu Arg Gln Ala Asn
                645                 650                 655

atc tct cag aaa gga gat gtg tac agc tat ggg atc atc gca cag gag      2133
Ile Ser Gln Lys Gly Asp Val Tyr Ser Tyr Gly Ile Ile Ala Gln Glu
            660                 665                 670

atc att ctg cgg aaa gaa acc ttc tac act ttg agc tgt cgg gac cgg      2181
Ile Ile Leu Arg Lys Glu Thr Phe Tyr Thr Leu Ser Cys Arg Asp Arg
        675                 680                 685

aat gag aag att ttc aga gtg gaa aat tcc aat gga atg aaa ccc ttc      2229
Asn Glu Lys Ile Phe Arg Val Glu Asn Ser Asn Gly Met Lys Pro Phe
    690                 695                 700

cgc cca gat tta ttc ttg gaa aca gca gag gaa aaa gag cta gaa gtg      2277
Arg Pro Asp Leu Phe Leu Glu Thr Ala Glu Glu Lys Glu Leu Glu Val
705                 710                 715                 720

tac cta ctt gta aaa aac tgt tgg gag gaa gat cca gaa aag aga cca      2325
Tyr Leu Leu Val Lys Asn Cys Trp Glu Glu Asp Pro Glu Lys Arg Pro
                725                 730                 735

gat ttc aaa aaa att gag act aca ctt gcc aag ata ttt gga ctt ttt      2373
Asp Phe Lys Lys Ile Glu Thr Thr Leu Ala Lys Ile Phe Gly Leu Phe
            740                 745                 750

cat gac caa aaa aat gaa agc tat atg gat acc ttg atc cga cgt cta      2421
His Asp Gln Lys Asn Glu Ser Tyr Met Asp Thr Leu Ile Arg Arg Leu
        755                 760                 765

cag cta tat tct cga aac ctg gaa cat ctg gta gag gaa agg aca cag      2469
Gln Leu Tyr Ser Arg Asn Leu Glu His Leu Val Glu Glu Arg Thr Gln
    770                 775                 780

ctg tac aag gca gag agg gac agg gct gac aga ctt aac ttt atg ttg      2517
Leu Tyr Lys Ala Glu Arg Asp Arg Ala Asp Arg Leu Asn Phe Met Leu
785                 790                 795                 800

ctt cca agg cta gtg gta aag tct ctg aag gag aaa ggc ttt gtg gag      2565
Leu Pro Arg Leu Val Val Lys Ser Leu Lys Glu Lys Gly Phe Val Glu
                805                 810                 815

ccg gaa cta tat gag gaa gtt aca atc tac ttc agt gac att gta ggt      2613
Pro Glu Leu Tyr Glu Glu Val Thr Ile Tyr Phe Ser Asp Ile Val Gly
            820                 825                 830

ttc act act atc tgc aaa tac agc acc ccc atg gaa gtg gtg gac atg      2661
Phe Thr Thr Ile Cys Lys Tyr Ser Thr Pro Met Glu Val Val Asp Met
        835                 840                 845

ctt aat gac atc tat aag agt ttt gac cac att gtt gat cat cat gat      2709
```

```
Leu Asn Asp Ile Tyr Lys Ser Phe Asp His Ile Val Asp His His Asp
    850                 855                 860

gtc tac aag gtg gaa acc atc ggt gat gcg tac atg gtg gct agt ggt     2757
Val Tyr Lys Val Glu Thr Ile Gly Asp Ala Tyr Met Val Ala Ser Gly
865                 870                 875                 880

ttg cct aag aga aat ggc aat cgg cat gca ata gac att gcc aag atg     2805
Leu Pro Lys Arg Asn Gly Asn Arg His Ala Ile Asp Ile Ala Lys Met
                885                 890                 895

gcc ttg gaa atc ctc agc ttc atg ggg acc ttt gag ctg gag cat ctt     2853
Ala Leu Glu Ile Leu Ser Phe Met Gly Thr Phe Glu Leu Glu His Leu
            900                 905                 910

cct ggc ctc cca ata tgg att cgc att gga gtt cac tct ggt ccc tgt     2901
Pro Gly Leu Pro Ile Trp Ile Arg Ile Gly Val His Ser Gly Pro Cys
        915                 920                 925

gct gct gga gtt gtg gga atc aag atg cct cgt tat tgt cta ttt gga     2949
Ala Ala Gly Val Val Gly Ile Lys Met Pro Arg Tyr Cys Leu Phe Gly
    930                 935                 940

gat acg gtc aac aca gcc tct agg atg gaa tcc act ggc ctc cct ttg     2997
Asp Thr Val Asn Thr Ala Ser Arg Met Glu Ser Thr Gly Leu Pro Leu
945                 950                 955                 960

aga att cac gtg agt ggc tcc acc ata gcc atc ctg aag aga act gag     3045
Arg Ile His Val Ser Gly Ser Thr Ile Ala Ile Leu Lys Arg Thr Glu
                965                 970                 975

tgc cag ttc ctt tat gaa gtg aga gga gaa aca tac tta aag gga aga     3093
Cys Gln Phe Leu Tyr Glu Val Arg Gly Glu Thr Tyr Leu Lys Gly Arg
            980                 985                 990

gga aat gag act acc tac tgg ctg  act ggg atg aag gac  cag aaa ttc   3141
Gly Asn Glu Thr Thr Tyr Trp Leu  Thr Gly Met Lys Asp  Gln Lys Phe
        995                 1000                1005

aac ctg  cca acc cct cct act  gtg gag aat caa cag  cgt ttg caa     3186
Asn Leu  Pro Thr Pro Pro Thr  Val Glu Asn Gln Gln  Arg Leu Gln
    1010                1015                1020

gca gaa  ttt tca gac atg att  gcc aac tct tta cag  aaa aga cag     3231
Ala Glu  Phe Ser Asp Met Ile  Ala Asn Ser Leu Gln  Lys Arg Gln
    1025                1030                1035

gca gca  ggg ata aga agc caa  aaa ccc aga cgg gta  gcc agc tat     3276
Ala Ala  Gly Ile Arg Ser Gln  Lys Pro Arg Arg Val  Ala Ser Tyr
    1040                1045                1050

aaa aaa  ggc act ctg gaa tac  ttg cag ctg aat acc  aca gac aag     3321
Lys Lys  Gly Thr Leu Glu Tyr  Leu Gln Leu Asn Thr  Thr Asp Lys
    1055                1060                1065

gag agc  acc tat ttt taa acctaaatga ggtataagga ctcacacaaa           3369
Glu Ser  Thr Tyr Phe
    1070

ttaaaataca gctgcactga ggccaggcac cctcaggtgt cctgaaagct tactttcctg   3429

agacctcatg aggcagaaat gtcttaggct tggctgccct gtttggacca tggactttct   3489

ttgcatgaat cagatgtgtt ctcagtgaaa taactacctt ccactctgga accttattcc   3549

agcagttgtt ccagggagct tctacctgga aaagaaaaga atttcattta tttttgttt    3609

gtttattttt atcgtttttg tttactggct ttccttctgt attcataaga tttttaaat    3669

tgtcataatt atattttaaa tacccatctt cattaaagta tatttaactc ataatttttg   3729

cagaaaatat gctatatatt aggcaagaat aaaagctaaa ggtttcccaa aaaaaaaa     3787
```

```
<210> SEQ ID NO 2
<211> LENGTH: 1073
<212> TYPE: PRT
<213> ORGANISM: Homo sapiens
```

<400> SEQUENCE: 2

Met Lys Thr Leu Leu Leu Asp Leu Ala Leu Trp Ser Leu Leu Phe Gln
1 5 10 15

Pro Gly Trp Leu Ser Phe Ser Ser Gln Val Ser Gln Asn Cys His Asn
20 25 30

Gly Ser Tyr Glu Ile Ser Val Leu Met Met Gly Asn Ser Ala Phe Ala
35 40 45

Glu Pro Leu Lys Asn Leu Glu Asp Ala Val Asn Glu Gly Leu Glu Ile
50 55 60

Val Arg Gly Arg Leu Gln Asn Ala Gly Leu Asn Val Thr Val Asn Ala
65 70 75 80

Thr Phe Met Tyr Ser Asp Gly Leu Ile His Asn Ser Gly Asp Cys Arg
85 90 95

Ser Ser Thr Cys Glu Gly Leu Asp Leu Leu Arg Lys Ile Ser Asn Ala
100 105 110

Gln Arg Met Gly Cys Val Leu Ile Gly Pro Ser Cys Thr Tyr Ser Thr
115 120 125

Phe Gln Met Tyr Leu Asp Thr Glu Leu Ser Tyr Pro Met Ile Ser Ala
130 135 140

Gly Ser Phe Gly Leu Ser Cys Asp Tyr Lys Glu Thr Leu Thr Arg Leu
145 150 155 160

Met Ser Pro Ala Arg Lys Leu Met Tyr Phe Leu Val Asn Phe Trp Lys
165 170 175

Thr Asn Asp Leu Pro Phe Lys Thr Tyr Ser Trp Ser Thr Ser Tyr Val
180 185 190

Tyr Lys Asn Gly Thr Glu Thr Glu Asp Cys Phe Trp Tyr Leu Asn Ala
195 200 205

Leu Glu Ala Ser Val Ser Tyr Phe Ser His Glu Leu Gly Phe Lys Val
210 215 220

Val Leu Arg Gln Asp Lys Glu Phe Gln Asp Ile Leu Met Asp His Asn
225 230 235 240

Arg Lys Ser Asn Val Ile Ile Met Cys Gly Gly Pro Glu Phe Leu Tyr
245 250 255

Lys Leu Lys Gly Asp Arg Ala Val Ala Glu Asp Ile Val Ile Ile Leu
260 265 270

Val Asp Leu Phe Asn Asp Gln Tyr Leu Glu Asp Asn Val Thr Ala Pro
275 280 285

Asp Tyr Met Lys Asn Val Leu Val Leu Thr Leu Ser Pro Gly Asn Ser
290 295 300

Leu Leu Asn Ser Ser Phe Ser Arg Asn Leu Ser Pro Thr Lys Arg Asp
305 310 315 320

Phe Arg Leu Ala Tyr Leu Asn Gly Ile Leu Val Phe Gly His Met Leu
325 330 335

Lys Ile Phe Leu Glu Asn Gly Glu Asn Ile Thr Thr Pro Lys Phe Ala
340 345 350

His Ala Phe Arg Asn Leu Thr Phe Glu Gly Tyr Asp Gly Pro Val Thr
355 360 365

Leu Asp Asp Trp Gly Asp Val Asp Ser Thr Met Val Leu Leu Tyr Thr
370 375 380

Ser Val Asp Thr Lys Lys Tyr Lys Val Leu Leu Thr Tyr Asp Thr His
385 390 395 400

Val Asn Lys Thr Tyr Pro Val Asp Met Ser Pro Thr Phe Thr Trp Lys
405 410 415

```
Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
        435                 440                 445

Val Ala Leu Leu Met Leu Arg Lys Tyr Arg Lys Asp Tyr Glu Leu Arg
    450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Val Lys Lys Arg
            500                 505                 510

Val Ile Leu Lys Asp Leu Lys His Asn Asp Gly Asn Phe Thr Glu Lys
        515                 520                 525

Gln Lys Ile Glu Leu Asn Lys Leu Leu Gln Ile Asp Tyr Tyr Thr Leu
    530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
        595                 600                 605

Thr Glu Val His Gly Arg Leu Lys Ser Thr Asn Cys Val Val Asp Ser
    610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
            660                 665                 670

Ile Ile Leu Arg Lys Glu Thr Phe Tyr Thr Leu Ser Cys Arg Asp Arg
        675                 680                 685

Asn Glu Lys Ile Phe Arg Val Glu Asn Ser Asn Gly Met Lys Pro Phe
    690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
            740                 745                 750

His Asp Gln Lys Asn Glu Ser Tyr Met Asp Thr Leu Ile Arg Arg Leu
        755                 760                 765

Gln Leu Tyr Ser Arg Asn Leu Glu His Leu Val Glu Glu Arg Thr Gln
    770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
            820                 825                 830
```

```
Phe Thr Thr Ile Cys Lys Tyr Ser Thr Pro Met Glu Val Val Asp Met
        835                 840                 845

Leu Asn Asp Ile Tyr Lys Ser Phe Asp His Ile Val Asp His His Asp
    850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
            900                 905                 910

Pro Gly Leu Pro Ile Trp Ile Arg Ile Gly Val His Ser Gly Pro Cys
        915                 920                 925

Ala Ala Gly Val Val Gly Ile Lys Met Pro Arg Tyr Cys Leu Phe Gly
    930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975

Cys Gln Phe Leu Tyr Glu Val Arg Gly Glu Thr Tyr Leu Lys Gly Arg
            980                 985                 990

Gly Asn Glu Thr Thr Tyr Trp Leu  Thr Gly Met Lys Asp  Gln Lys Phe
        995                 1000                 1005

Asn Leu  Pro Thr Pro Pro Thr  Val Glu Asn Gln Gln  Arg Leu Gln
    1010                 1015                 1020

Ala Glu  Phe Ser Asp Met Ile  Ala Asn Ser Leu Gln  Lys Arg Gln
    1025                 1030                 1035

Ala Ala  Gly Ile Arg Ser Gln  Lys Pro Arg Arg Val  Ala Ser Tyr
    1040                 1045                 1050

Lys Lys  Gly Thr Leu Glu Tyr  Leu Gln Leu Asn Thr  Thr Asp Lys
    1055                 1060                 1065

Glu Ser  Thr Tyr Phe
    1070


<210> SEQ ID NO 3
<211> LENGTH: 15
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(15)

<400> SEQUENCE: 3

atg aaa ggg ttt ccc                                                15
Met Lys Gly Phe Pro
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Met Lys Gly Phe Pro
1               5
```

```
<210> SEQ ID NO 5
<211> LENGTH: 1287
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(1287)

<400> SEQUENCE: 5

atg aaa aca ctg ctg ctg gat ctc gct ctg tgg tca ctc ctc ttt cag       48
Met Lys Thr Leu Leu Leu Asp Leu Ala Leu Trp Ser Leu Leu Phe Gln
1               5                   10                  15

ccc gga tgg ctg tca ttt tct tcc cag gtg tcc cag aat tgt cac aac       96
Pro Gly Trp Leu Ser Phe Ser Ser Gln Val Ser Gln Asn Cys His Asn
            20                  25                  30

ggc tcc tac gaa atc tct gtc ctc atg atg ggc aat agc gcc ttt gcc      144
Gly Ser Tyr Glu Ile Ser Val Leu Met Met Gly Asn Ser Ala Phe Ala
        35                  40                  45

gaa cct ctc aaa aac ctc gag gat gct gtg aat gag gga ctg gag att      192
Glu Pro Leu Lys Asn Leu Glu Asp Ala Val Asn Glu Gly Leu Glu Ile
    50                  55                  60

gtg agg gga cga ctc cag aac gct gga ctg aat gtc acc gtg aat gcc      240
Val Arg Gly Arg Leu Gln Asn Ala Gly Leu Asn Val Thr Val Asn Ala
65                  70                  75                  80

act ttc atg tac tcc gat ggc ctc atc cat aat agt ggc gac tgt cgg      288
Thr Phe Met Tyr Ser Asp Gly Leu Ile His Asn Ser Gly Asp Cys Arg
                85                  90                  95

tct agc aca tgt gag gga ctc gat ctg ctc cga aaa att tcc aac gcc      336
Ser Ser Thr Cys Glu Gly Leu Asp Leu Leu Arg Lys Ile Ser Asn Ala
            100                 105                 110

cag cga atg gga tgt gtg ctc att gga ccc tct tgt acc tac tcc aca      384
Gln Arg Met Gly Cys Val Leu Ile Gly Pro Ser Cys Thr Tyr Ser Thr
        115                 120                 125

ttt cag atg tac ctc gac acc gaa ctg tct tac ccc atg atc tct gcc      432
Phe Gln Met Tyr Leu Asp Thr Glu Leu Ser Tyr Pro Met Ile Ser Ala
    130                 135                 140

gga tcc ttt gga ctg tcc tgt gat tac aag gag aca ctc act aga ctc      480
Gly Ser Phe Gly Leu Ser Cys Asp Tyr Lys Glu Thr Leu Thr Arg Leu
145                 150                 155                 160

atg tcc ccc gct cga aaa ctc atg tac ttt ctc gtg aac ttc tgg aaa      528
Met Ser Pro Ala Arg Lys Leu Met Tyr Phe Leu Val Asn Phe Trp Lys
                165                 170                 175

acc aac gac ctg ccc ttc aaa aca tac tcc tgg tca act tca tac gtc      576
Thr Asn Asp Leu Pro Phe Lys Thr Tyr Ser Trp Ser Thr Ser Tyr Val
            180                 185                 190

tac aaa aac ggc acc gaa acc gag gat tgc ttt tgg tac ctc aat gcc      624
Tyr Lys Asn Gly Thr Glu Thr Glu Asp Cys Phe Trp Tyr Leu Asn Ala
        195                 200                 205

ctg gag gct agc gtg tca tac ttt agc cac gaa ctc gga ttc aaa gtc      672
Leu Glu Ala Ser Val Ser Tyr Phe Ser His Glu Leu Gly Phe Lys Val
    210                 215                 220

gtg ctg agg cag gat aag gag ttc cag gat att ctc atg gac cat aac      720
Val Leu Arg Gln Asp Lys Glu Phe Gln Asp Ile Leu Met Asp His Asn
225                 230                 235                 240

cgg aaa tca aac gtg atc atc atg tgt gga ggc cct gaa ttt ctg tac      768
Arg Lys Ser Asn Val Ile Ile Met Cys Gly Gly Pro Glu Phe Leu Tyr
                245                 250                 255

aaa ctc aag ggc gat aga gct gtg gct gag gat att gtc atc att ctc      816
Lys Leu Lys Gly Asp Arg Ala Val Ala Glu Asp Ile Val Ile Ile Leu
            260                 265                 270
```

```
gtg gat ctc ttc aac gac cag tac ttc gag gat aac gtg act gct ccc      864
Val Asp Leu Phe Asn Asp Gln Tyr Phe Glu Asp Asn Val Thr Ala Pro
        275                 280                 285

gac tac atg aaa aac gtc ctg gtg ctc aca ctg agt cct ggc aat tcc      912
Asp Tyr Met Lys Asn Val Leu Val Leu Thr Leu Ser Pro Gly Asn Ser
    290                 295                 300

ctg ctg aat tcc tcc ttt tct cga aac ctg tcc cca aca aaa cgg gat      960
Leu Leu Asn Ser Ser Phe Ser Arg Asn Leu Ser Pro Thr Lys Arg Asp
305                 310                 315                 320

ttt gct ctg gct tac ctg aac ggg att ctc ctg ttt ggc cac atg ctc     1008
Phe Ala Leu Ala Tyr Leu Asn Gly Ile Leu Leu Phe Gly His Met Leu
                325                 330                 335

aaa atc ttt ctg gaa aat ggc gag aac atc acc acc ccc aaa ttt gct     1056
Lys Ile Phe Leu Glu Asn Gly Glu Asn Ile Thr Thr Pro Lys Phe Ala
            340                 345                 350

cac gcc ttc cgg aat ctc act ttt gag ggc tac gac gga cct gtg act     1104
His Ala Phe Arg Asn Leu Thr Phe Glu Gly Tyr Asp Gly Pro Val Thr
        355                 360                 365

ctg gac gat tgg ggc gac gtg gat agc aca atg gtg ctg ctc tac acc     1152
Leu Asp Asp Trp Gly Asp Val Asp Ser Thr Met Val Leu Leu Tyr Thr
    370                 375                 380

tct gtc gat act aaa aaa tac aaa gtc ctg ctc acc tac gat act cac     1200
Ser Val Asp Thr Lys Lys Tyr Lys Val Leu Leu Thr Tyr Asp Thr His
385                 390                 395                 400

gtc aac aaa acc tac cct gtg gat atg agc cca acc ttc act tgg aaa     1248
Val Asn Lys Thr Tyr Pro Val Asp Met Ser Pro Thr Phe Thr Trp Lys
                405                 410                 415

aac tcc aaa ctg cca aat gat att acc ggg cga gga ccc                 1287
Asn Ser Lys Leu Pro Asn Asp Ile Thr Gly Arg Gly Pro
            420                 425
```

```
<210> SEQ ID NO 6
<211> LENGTH: 429
<212> TYPE: PRT
<213> ORGANISM: Artificial Sequence
<220> FEATURE:
<223> OTHER INFORMATION: Synthetic Construct

<400> SEQUENCE: 6

Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
```

```
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro
            420                 425
```

<210> SEQ ID NO 7
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(39)

<400> SEQUENCE: 7

```
gcc aaa ttc gtc gct gct tgg aca ctg aag gct gct gcc tagtaa            45
Ala Lys Phe Val Ala Ala Trp Thr Leu Lys Ala Ala Ala
1               5                   10
```

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

```
Ala Lys Phe Val Ala Ala Trp Thr Leu Lys Ala Ala Ala
1               5                   10


<210> SEQ ID NO 9
<211> LENGTH: 1332
<212> TYPE: DNA
<213> ORGANISM: Homo sapiens
<220> FEATURE:
<221> NAME/KEY: CDS
<222> LOCATION: (1)..(1329)

<400> SEQUENCE: 9

atg aaa aca ctg ctg ctg gat ctc gct ctg tgg tca ctc ctc ttt cag       48
Met Lys Thr Leu Leu Leu Asp Leu Ala Leu Trp Ser Leu Leu Phe Gln
1               5                   10                  15

ccc gga tgg ctg tca ttt tct tcc cag gtg tcc cag aat tgt cac aac       96
Pro Gly Trp Leu Ser Phe Ser Ser Gln Val Ser Gln Asn Cys His Asn
            20                  25                  30

ggc tcc tac gaa atc tct gtc ctc atg atg ggc aat agc gcc ttt gcc      144
Gly Ser Tyr Glu Ile Ser Val Leu Met Met Gly Asn Ser Ala Phe Ala
        35                  40                  45

gaa cct ctc aaa aac ctc gag gat gct gtg aat gag gga ctg gag att      192
Glu Pro Leu Lys Asn Leu Glu Asp Ala Val Asn Glu Gly Leu Glu Ile
    50                  55                  60

gtg agg gga cga ctc cag aac gct gga ctg aat gtc acc gtg aat gcc      240
Val Arg Gly Arg Leu Gln Asn Ala Gly Leu Asn Val Thr Val Asn Ala
65                  70                  75                  80

act ttc atg tac tcc gat ggc ctc atc cat aat agt ggc gac tgt cgg      288
Thr Phe Met Tyr Ser Asp Gly Leu Ile His Asn Ser Gly Asp Cys Arg
                85                  90                  95

tct agc aca tgt gag gga ctc gat ctg ctc cga aaa att tcc aac gcc      336
Ser Ser Thr Cys Glu Gly Leu Asp Leu Leu Arg Lys Ile Ser Asn Ala
            100                 105                 110

cag cga atg gga tgt gtg ctc att gga ccc tct tgt acc tac tcc aca      384
Gln Arg Met Gly Cys Val Leu Ile Gly Pro Ser Cys Thr Tyr Ser Thr
        115                 120                 125

ttt cag atg tac ctc gac acc gaa ctg tct tac ccc atg atc tct gcc      432
Phe Gln Met Tyr Leu Asp Thr Glu Leu Ser Tyr Pro Met Ile Ser Ala
    130                 135                 140

gga tcc ttt gga ctg tcc tgt gat tac aag gag aca ctc act aga ctc      480
Gly Ser Phe Gly Leu Ser Cys Asp Tyr Lys Glu Thr Leu Thr Arg Leu
145                 150                 155                 160

atg tcc ccc gct cga aaa ctc atg tac ttt ctc gtg aac ttc tgg aaa      528
Met Ser Pro Ala Arg Lys Leu Met Tyr Phe Leu Val Asn Phe Trp Lys
                165                 170                 175

acc aac gac ctg ccc ttc aaa aca tac tcc tgg tca act tca tac gtc      576
Thr Asn Asp Leu Pro Phe Lys Thr Tyr Ser Trp Ser Thr Ser Tyr Val
            180                 185                 190

tac aaa aac ggc acc gaa acc gag gat tgc ttt tgg tac ctc aat gcc      624
Tyr Lys Asn Gly Thr Glu Thr Glu Asp Cys Phe Trp Tyr Leu Asn Ala
        195                 200                 205

ctg gag gct agc gtg tca tac ttt agc cac gaa ctc gga ttc aaa gtc      672
Leu Glu Ala Ser Val Ser Tyr Phe Ser His Glu Leu Gly Phe Lys Val
    210                 215                 220

gtg ctg agg cag gat aag gag ttc cag gat att ctc atg gac cat aac      720
Val Leu Arg Gln Asp Lys Glu Phe Gln Asp Ile Leu Met Asp His Asn
225                 230                 235                 240

cgg aaa tca aac gtg atc atc atg tgt gga ggc cct gaa ttt ctg tac      768
Arg Lys Ser Asn Val Ile Ile Met Cys Gly Gly Pro Glu Phe Leu Tyr
                245                 250                 255
```

```
aaa ctc aag ggc gat aga gct gtg gct gag gat att gtc atc att ctc      816
Lys Leu Lys Gly Asp Arg Ala Val Ala Glu Asp Ile Val Ile Ile Leu
            260                 265                 270

gtg gat ctc ttc aac gac cag tac ttc gag gat aac gtg act gct ccc      864
Val Asp Leu Phe Asn Asp Gln Tyr Phe Glu Asp Asn Val Thr Ala Pro
        275                 280                 285

gac tac atg aaa aac gtc ctg gtg ctc aca ctg agt cct ggc aat tcc      912
Asp Tyr Met Lys Asn Val Leu Val Leu Thr Leu Ser Pro Gly Asn Ser
    290                 295                 300

ctg ctg aat tcc tcc ttt tct cga aac ctg tcc cca aca aaa cgg gat      960
Leu Leu Asn Ser Ser Phe Ser Arg Asn Leu Ser Pro Thr Lys Arg Asp
305                 310                 315                 320

ttt gct ctg gct tac ctg aac ggg att ctc ctg ttt ggc cac atg ctc     1008
Phe Ala Leu Ala Tyr Leu Asn Gly Ile Leu Leu Phe Gly His Met Leu
                325                 330                 335

aaa atc ttt ctg gaa aat ggc gag aac atc acc acc ccc aaa ttt gct     1056
Lys Ile Phe Leu Glu Asn Gly Glu Asn Ile Thr Thr Pro Lys Phe Ala
            340                 345                 350

cac gcc ttc cgg aat ctc act ttt gag ggc tac gac gga cct gtg act     1104
His Ala Phe Arg Asn Leu Thr Phe Glu Gly Tyr Asp Gly Pro Val Thr
        355                 360                 365

ctg gac gat tgg ggc gac gtg gat agc aca atg gtg ctg ctc tac acc     1152
Leu Asp Asp Trp Gly Asp Val Asp Ser Thr Met Val Leu Leu Tyr Thr
    370                 375                 380

tct gtc gat act aaa aaa tac aaa gtc ctg ctc acc tac gat act cac     1200
Ser Val Asp Thr Lys Lys Tyr Lys Val Leu Leu Thr Tyr Asp Thr His
385                 390                 395                 400

gtc aac aaa acc tac cct gtg gat atg agc cca acc ttc act tgg aaa     1248
Val Asn Lys Thr Tyr Pro Val Asp Met Ser Pro Thr Phe Thr Trp Lys
                405                 410                 415

aac tcc aaa ctg cca aat gat att acc ggg cga gga ccc gcc aaa ttc     1296
Asn Ser Lys Leu Pro Asn Asp Ile Thr Gly Arg Gly Pro Ala Lys Phe
            420                 425                 430

gtc gct gct tgg aca ctg aag gct gct gcc tag taa                     1332
Val Ala Ala Trp Thr Leu Lys Ala Ala Ala
        435                 440


<210> SEQ ID NO 10
<211> LENGTH: 442
<212> TYPE: PRT
<213> ORGANISM: Homo sapiens

<400> SEQUENCE: 10

Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125
```

```
Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Ala Lys Phe
            420                 425                 430

Val Ala Ala Trp Thr Leu Lys Ala Ala Ala
        435                 440


<210> SEQ ID NO 11
<211> LENGTH: 32806
<212> TYPE: DNA
<213> ORGANISM: Artificial Sequence
<220> FEATURE:
<223> OTHER INFORMATION: synthetic construct

<400> SEQUENCE: 11

attaacatca tcaataatat accttatttt ggattgaagc caatatgata atgagggggt      60

ggagtttgtg acgtggcgcg gggcgtggga acggggcggg tgacgtagta gtgtggcgga     120

agtgtgatgt tgcaagtgtg gcggaacaca tgtaagcgac ggatgtggca aaagtgacgt     180

ttttggtgtg cgccggtgta cacaggaagt gacaattttc gcgcggtttt aggcggatgt     240
```

-continued

```
tgtagtaaat ttgggcgtaa ccgagtaaga tttggccatt ttcgcgggaa aactgaataa    300
gaggaagtga aatctgaata attttgtgtt actcatagcg cgtaatctct agcatcgtaa    360
ctataacggt cctaaggtag cgaaagctca gatctggatc tcccgatccc ctatggtcga    420
ctctcagtac aatctgctct gatgccgcat agttaagcca gtatctgctc cctgcttgtg    480
tgttggaggt cgctgagtag tgcgcgagca aaatttaagc tacaacaagg caaggcttga    540
ccgacaattg catgaagaat ctgcttaggg ttaggcgttt tgcgctgctt cgcgatgtac    600
gggccagata tacgcgttga cattgattat tgactagtta ttaatagtaa tcaattacgg    660
ggtcattagt tcatagccca tatatggagt tccgcgttac ataacttacg gtaaatggcc    720
cgcctggctg accgcccaac gacccccgcc cattgacgtc aataatgacg tatgttccca    780
tagtaacgcc aatagggact ttccattgac gtcaatgggt ggactattta cggtaaactg    840
cccacttggc agtacatcaa gtgtatcata tgccaagtac gccccctatt gacgtcaatg    900
acggtaaatg gcccgcctgg cattatgccc agtacatgac cttatgggac tttcctactt    960
ggcagtacat ctacgtatta gtcatcgcta ttaccatggt gatgcggttt tggcagtaca   1020
tcaatgggcg tggatagcgg tttgactcac ggggatttcc aagtctccac cccattgacg   1080
tcaatgggag tttgttttgg caccaaaatc aacgggactt tccaaaatgt cgtaacaact   1140
ccgccccatt gacgcaaatg ggcggtaggc gtgtacggtg ggaggtctat ataagcagag   1200
ctctctggct aactagagaa cccactgctt actggcttat cgaaattaat acgactcact   1260
atagggagac ccaagctggc tagcgtttaa acgggccctc tagagccgcc accatgaaaa   1320
cactgctgct ggatctcgct ctgtggtcac tcctctttca gcccggatgg ctgtcatttt   1380
cttcccaggt gtcccagaat tgtcacaacg gctcctacga aatctctgtc ctcatgatgg   1440
gcaatagcgc ctttgccgaa cctctcaaaa acctcgagga tgctgtgaat gagggactgg   1500
agattgtgag ggacgactc cagaacgctg gactgaatgt caccgtgaat gccactttca   1560
tgtactccga tggcctcatc cataatagtg gcgactgtcg gtctagcaca tgtgagggac   1620
tcgatctgct ccgaaaaatt tccaacgccc agcgaatggg atgtgtgctc attggaccct   1680
cttgtaccta ctccacattt cagatgtacc tcgacaccga actgtcttac cccatgatct   1740
ctgccggatc ctttggactg tcctgtgatt acaaggagac actcactaga ctcatgtccc   1800
ccgctcgaaa actcatgtac tttctcgtga acttctggaa aaccaacgac ctgcccttca   1860
aaacatactc ctggtcaact tcatacgtct acaaaaacgg caccgaaacc gaggattgct   1920
tttggtacct caatgccctg gaggctagcg tgtcatactt tagccacgaa ctcggattca   1980
aagtcgtgct gaggcaggat aaggagttcc aggatattct catggaccat aaccggaaat   2040
caaacgtgat catcatgtgt ggaggccctg aatttctgta caaactcaag ggcgatagag   2100
ctgtggctga ggatattgtc atcattctcg tggatctctt caacgaccag tacttcgagg   2160
ataacgtgac tgctcccgac tacatgaaaa acgtcctggt gctcacactg agtcctggca   2220
attccctgct gaattcctcc ttttctcgaa acctgtcccc aacaaaacgg gattttgctc   2280
tggcttacct gaacgggatt ctcctgtttg gccacatgct caaaatcttt ctggaaaatg   2340
gcgagaacat caccaccccc aaatttgctc acgccttccg gaatctcact tttgagggct   2400
acgacggacc tgtgactctg gacgattggg gcgacgtgga tagcacaatg gtgctgctct   2460
acacctctgt cgatactaaa aaatacaaag tcctgctcac ctacgatact cacgtcaaca   2520
aaacctaccc tgtggatatg agcccaacct tcacttggaa aaactccaaa ctgccaaatg   2580
atattaccgg gcgaggaccc gccaaattcg tcgctgcttg gacactgaag gctgctgcct   2640
```

```
agtaagcggc cgccactgtg ctggatgatc cgagctcggt accaagctta agtttaaacc   2700
gctgatcagc ctcgactgtg ccttctagtt gccagccatc tgttgtttgc ccctcccccg   2760
tgccttcctt gaccctggaa ggtgccactc ccactgtcct ttcctaataa aatgaggaaa   2820
ttgcatcgca ttgtctgagt aggtgtcatt ctattctggg gggtggggtg gggcaggaca   2880
gcaaggggga ggattgggaa gacaatagca ggcatgctgg ggatgcggtg ggctctatgg   2940
cttctgaggc ggaaagaacc agcagatctg cagatctgaa ttcatctatg tcgggtgcgg   3000
agaaagaggt aatgaaatgg catcgactcg aagatctggg cgtggttaag ggtgggaaag   3060
aatatataag gtgggggtct tatgtagttt tgtatctgtt ttgcagcagc cgccgccgcc   3120
atgagcacca actcgtttga tggaagcatt gtgagctcat atttgacaac gcgcatgccc   3180
ccatgggccg gggtgcgtca gaatgtgatg ggctccagca ttgatggtcg ccccgtcctg   3240
cccgcaaact ctactacctt gacctacgag accgtgtctg gaacgccgtt ggagactgca   3300
gcctccgccg ccgcttcagc cgctgcagcc accgcccgcg ggattgtgac tgactttgct   3360
ttcctgagcc cgcttgcaag cagtgcagct tcccgttcat ccgcccgcga tgacaagttg   3420
acggctcttt tggcacaatt ggattctttg acccgggaac ttaatgtcgt ttctcagcag   3480
ctgttggatc tgcgccagca ggtttctgcc ctgaaggctt cctcccctcc caatgcggtt   3540
taaaacataa ataaaaaacc agactctgtt tggatttgga tcaagcaagt gtcttgctgt   3600
ctttatttag gggttttgcg cgcgcggtag gcccgggacc agcggtctcg gtcgttgagg   3660
gtcctgtgta tttttttccag gacgtggtaa aggtgactct ggatgttcag atacatgggc   3720
ataagcccgt ctctggggtg gaggtagcac cactgcagag cttcatgctg cggggtggtg   3780
ttgtagatga tccagtcgta gcaggagcgc tgggcgtggt gcctaaaaat gtctttcagt   3840
agcaagctga ttgccagggg caggcccttg gtgtaagtgt ttacaaagcg gttaagctgg   3900
gatgggtgca tacgtgggga tatgagatgc atcttggact gtatttttag gttggctatg   3960
ttcccagcca tatccctccg gggattcatg ttgtgcagaa ccaccagcac agtgtatccg   4020
gtgcacttgg gaaatttgtc atgtagctta gaaggaaatg cgtggaagaa cttggagacg   4080
cccttgtgac ctccaagatt ttccatgcat tcgtccataa tgatggcaat gggcccacgg   4140
gcggcggcct gggcgaagat atttctggga tcactaacgt catagttgtg ttccaggatg   4200
agatcgtcat aggccatttt tacaaagcgc gggcggaggg tgccagactg cggtataatg   4260
gttccatccg gcccaggggc gtagttaccc tcacagattt gcatttccca cgctttgagt   4320
tcagatgggg ggatcatgtc tacctgcggg gcgatgaaga aaacggtttc cggggtaggg   4380
gagatcagct gggaagaaag caggttcctg agcagctgcg acttaccgca gccggtgggc   4440
ccgtaaatca cacctattac cgggtgcaac tggtagttaa gagagctgca gctgccgtca   4500
tccctgagca ggggggccac ttcgttaagc atgtccctga ctcgcatgtt ttccctgacc   4560
aaatccgcca gaaggcgctc gccgcccagc gatagcagtt cttgcaagga agcaaagttt   4620
ttcaacggtt tgagaccgtc cgccgtaggc atgcttttga gcgtttgacc aagcagttcc   4680
aggcggtccc acagctcggt cacctgctct acggcatctc gatccagcat atctcctcgt   4740
ttcgcgggtt ggggcggctt tcgctgtacg gcagtagtcg gtgctcgtcc agacgggcca   4800
gggtcatgtc tttccacggg cgcagggtcc tcgtcagcgt agtctgggtc acggtgaagg   4860
ggtgcgctcc gggctgcgcg ctggccaggg tgcgcttgag gctggtcctg ctggtgctga   4920
agcgctgccg gtcttcgccc tgcgcgtcgg ccaggtagca tttgaccatg gtgtcatagt   4980
```

```
ccagcccctc cgcggcgtgg cccttggcgc gcagcttgcc cttggaggag gcgccgcacg   5040
aggggcagtg cagacttttg agggcgtaga gcttgggcgc gagaaatacc gattccgggg   5100
agtaggcatc cgcgccgcag gccccgcaga cggtctcgca ttccacgagc caggtgagct   5160
ctggccgttc ggggtcaaaa accaggtttc cccatgctt tttgatgcgt ttcttacctc   5220
tggtttccat gagccggtgt ccacgctcgg tgacgaaaag gctgtccgtg tccccgtata   5280
cagacttgag aggcctgtcc tcgagcggtg ttccgcggtc ctcctcgtat agaaactcgg   5340
accactctga gacaaaggct cgcgtccagg ccagcacgaa ggaggctaag tgggaggggt   5400
agcggtcgtt gtccactagg gggtccactc gctccagggt gtgaagacac atgtcgccct   5460
cttcggcatc aaggaaggtg attggtttgt aggtgtaggc cacgtgaccg ggtgttcctg   5520
aagggggggct ataaaagggg gtgggggcgc gttcgtcctc actctcttcc gcatcgctgt   5580
ctgcgagggc cagctgttgg ggtgagtact ccctctgaaa agcgggcatg acttctgcgc   5640
taagattgtc agtttccaaa aacgaggagg atttgatatt cacctggccc gcggtgatgc   5700
ctttgagggt ggccgcatcc atctggtcag aaaagacaat ctttttgttg tcaagcttgg   5760
tggcaaacga cccgtagagg gcgttggaca gcaacttggc gatggagcgc agggtttggt   5820
ttttgtcgcg atcggcgcgc tccttggccg cgatgtttag ctgcacgtat tcgcgcgcaa   5880
cgcaccgcca ttcgggaaag acggtggtgc gctcgtcggg caccaggtgc acgcgccaac   5940
cgcggttgtg cagggtgaca aggtcaacgc tggtggctac ctctccgcgt aggcgctcgt   6000
tggtccagca gaggcggccg cccttgcgcg agcagaatgg cggtaggggg tctagctgcg   6060
tctcgtccgg ggggtctgcg tccacggtaa agaccccggg cagcaggcgc gcgtcgaagt   6120
agtctatctt gcatccttgc aagtctagcg cctgctgcca tgcgcgggcg gcaagcgcgc   6180
gctcgtatgg gttgagtggg ggaccccatg gcatggggtg ggtgagcgcg gaggcgtaca   6240
tgccgcaaat gtcgtaaacg tagaggggct ctctgagtat tccaagatat gtagggtagc   6300
atcttccacc gcggatgctg gcgcgcacgt aatcgtatag ttcgtgcgag ggagcgagga   6360
ggtcgggacc gaggttgcta cgggcgggct gctctgctcg gaagactatc tgcctgaaga   6420
tggcatgtga gttggatgat atggttggac gctggaagac gttgaagctg gcgtctgtga   6480
gacctaccgc gtcacgcacg aaggaggcgt aggagtcgcg cagcttgttg accagctcgg   6540
cggtgacctg cacgtctagg gcgcagtagt ccagggtttc cttgatgatg tcatacttat   6600
cctgtccctt tttttccac agctcgcggt tgaggacaaa ctcttcgcgg tctttccagt   6660
actcttggat cggaaacccg tcggcctccg aacggtaaga gcctagcatg tagaactggt   6720
tgacggcctg gtaggcgcag catccctttt ctacgggtag cgcgtatgcc tgcgcggcct   6780
tccggagcga ggtgtgggtg agcgcaaagg tgtccctgac catgactttg aggtactggt   6840
atttgaagtc agtgtcgtcg catccgccct gctcccagag caaaaagtcc gtgcgctttt   6900
tggaacgcgg atttggcagg gcgaaggtga catcgttgaa gagtatcttt cccgcgcgag   6960
gcataaagtt gcgtgtgatg cggaagggtc ccggcacctc ggaacggttg ttaattacct   7020
gggcggcgag cacgatctcg tcaaagccgt tgatgttgtg gcccacaatg taaagttcca   7080
agaagcgcgg gatgcccttg atggaaggca attttttaag ttcctcgtag gtgagctctt   7140
caggggagct gagcccgtgc tctgaaaggg cccagtctgc aagatgaggg ttggaagcga   7200
cgaatgagct ccacaggtca cgggccatta gcatttgcag gtggtcgcga aaggtcctaa   7260
actggcgacc tatggccatt ttttctgggg tgatgcagta gaaggtaagc gggtcttgtt   7320
cccagcggtc ccatccaagg ttcgcggcta ggtctcgcgc ggcagtcact agaggctcat   7380
```

```
ctccgccgaa cttcatgacc agcatgaagg gcacgagctg cttcccaaag gcccccatcc   7440
aagtataggt ctctacatcg taggtgacaa agagacgctc ggtgcgagga tgcgagccga   7500
tcgggaagaa ctggatctcc cgccaccaat tggaggagtg gctattgatg tggtgaaagt   7560
agaagtccct gcgacgggcc gaacactcgt gctggctttt gtaaaaacgt gcgcagtact   7620
ggcagcggtg cacgggctgt acatcctgca cgaggttgac ctgacgaccg cgcacaagga   7680
agcagagtgg gaatttgagc ccctcgcctg gcgggtttgg ctggtggtct tctacttcgg   7740
ctgcttgtcc ttgaccgtct ggctgctcga ggggagttac ggtggatcgg accaccacgc   7800
cgcgcgagcc caaagtccag atgtccgcgc gcggcggtcg gagcttgatg acaacatcgc   7860
gcagatggga gctgtccatg gtctggagct cccgcggcgt caggtcaggc gggagctcct   7920
gcaggtttac ctcgcataga cgggtcaggg cgcgggctag atccaggtga tacctaattt   7980
ccaggggctg gttggtggcg gcgtcgatgg cttgcaagag gccgcatccc cgcggcgcga   8040
ctacggtacc gcgcggcggg cggtgggccg cgggggtgtc cttggatgat gcatctaaaa   8100
gcggtgacgc gggcgagccc ccggaggtag ggggggctcc ggacccgccg ggagaggggg   8160
caggggcacg tcggcgccgc gcgcgggcag gagctggtgc tgcgcgcgta ggttgctggc   8220
gaacgcgacg acgcggcggt tgatctcctg aatctggcgc ctctgcgtga agacgacggg   8280
cccggtgagc ttgagcctga aagagagttc gacagaatca atttcggtgt cgttgacggc   8340
ggcctggcgc aaaatctcct gcacgtctcc tgagttgtct tgataggcga tctcggccat   8400
gaactgctcg atctcttcct cctggagatc tccgcgtccg gctcgctcca cggtggcggc   8460
gaggtcgttg gaaatgcggg ccatgagctg cgagaaggcg ttgaggcctc cctcgttcca   8520
gacgcggctg tagaccacgc ccccttcggc atcgcgggcg cgcatgacca cctgcgcgag   8580
attgagctcc acgtgccggg cgaagacggc gtagtttcgc aggcgctgaa agaggtagtt   8640
gagggtggtg gcggtgtgtt ctgccacgaa gaagtacata acccagcgtc gcaacgtgga   8700
ttcgttgata tcccccaagg cctcaaggcg ctccatggcc tcgtagaagt ccacggcgaa   8760
gttgaaaaac tgggagttgc gcgccgacac ggttaactcc tcctccagaa gacggatgag   8820
ctcggcgaca gtgtcgcgca cctcgcgctc aaaggctaca ggggcctctt cttcttcttc   8880
aatctcctct tccataaggg cctccccttc ttcttcttct ggcggcggtg ggggaggggg   8940
gacacggcgg cgacgacggc gcaccgggag gcggtcgaca aagcgctcga tcatctcccc   9000
gcggcgacgg cgcatggtct cggtgacggc gcggccgttc tcgcgggggc gcagttggaa   9060
gacgccgccc gtcatgtccc ggttatgggt tggcgggggg ctgccatgcg gcagggatac   9120
ggcgctaacg atgcatctca acaattgttg tgtaggtact ccgccgccga gggacctgag   9180
cgagtccgca tcgaccggat cggaaaacct ctcgagaaag gcgtctaacc agtcacagtc   9240
gcaaggtagg ctgagcaccg tggcgggcgg cagcgggcgg cggtcggggt tgtttctggc   9300
ggaggtgctg ctgatgatgt aattaaagta ggcggtcttg agacggcgga tggtcgacag   9360
aagcaccatg tccttgggtc cggcctgctg aatgcgcagg cggtcggcca tgccccaggc   9420
ttcgttttga catcggcgca ggtctttgta gtagtcttgc atgagccttt ctaccggcac   9480
ttcttcttct ccttcctctt gtcctgcatc tcttgcatct atcgctgcgg cggcggcgga   9540
gtttggccgt aggtggcgcc ctcttcctcc catgcgtgtg accccgaagc ccctcatcgg   9600
ctgaagcagg gctaggtcgg cgacaacgcg ctcggctaat atggcctgct gcacctgcgt   9660
gagggtagac tggaagtcat ccatgtccac aaagcggtgg tatgcgcccg tgttgatggt   9720
```

```
gtaagtgcag ttggccataa cggaccagtt aacggtctgg tgacccggct gcgagagctc   9780
ggtgtacctg agacgcgagt aagccctcga gtcaaatacg tagtcgttgc aagtccgcac   9840
caggtactgg tatcccacca aaaagtgcgg cggcggctgg cggtagaggg gccagcgtag   9900
ggtggccggg gctccggggg cgagatcttc caacataagg cgatgatatc cgtagatgta   9960
cctggacatc caggtgatgc cggcggcggt ggtggaggcg cgcggaaagt cgcggacgcg  10020
gttccagatg ttgcgcagcg gcaaaaagtg ctccatggtc gggacgctct ggccggtcag  10080
gcgcgcgcaa tcgttgacgc tctagaccgt gcaaaaggag agcctgtaag cgggcactct  10140
tccgtggtct ggtggataaa ttcgcaaggg tatcatggcg gacgaccggg gttcgagccc  10200
cgtatccggc cgtccgccgt gatccatgcg gttaccgccc gcgtgtcgaa cccaggtgtg  10260
cgacgtcaga caacggggga gtgctccttt tggcttcctt ccaggcgcgg cggctgctgc  10320
gctagctttt ttggccactg gccgcgcgca gcgtaagcgg ttaggctgga aagcgaaagc  10380
attaagtggc tcgctccctg tagccggagg gttattttcc aagggttgag tcgcgggacc  10440
cccggttcga gtctcggacc ggccggactg cggcgaacgg gggtttgcct ccccgtcatg  10500
caagaccccg cttgcaaatt cctccggaaa cagggacgag cccctttttt gcttttccca  10560
gatgcatccg gtgctgcggc agatgcgccc ccctcctcag cagcggcaag agcaagagca  10620
gcggcagaca tgcagggcac cctcccctcc tcctaccgcg tcaggagggg cgacatccgc  10680
ggttgacgcg gcagcagatg gtgattacga acccccgcgg cgccgggccc ggcactacct  10740
ggacttggag gagggcgagg gcctggcgcg gctaggagcg ccctctcctg agcggtaccc  10800
aagggtgcag ctgaagcgtg atacgcgtga ggcgtacgtg ccgcggcaga acctgtttcg  10860
cgaccgcgag ggagaggagc ccgaggagat gcgggatcga aagttccacg cagggcgcga  10920
gctgcggcat ggcctgaatc gcgagcggtt gctgcgcgag gaggactttg agcccgacgc  10980
gcgaaccggg attagtcccg cgcgcgcaca cgtggcggcc gccgacctgg taaccgcata  11040
cgagcagacg gtgaaccagg agattaactt tcaaaaaagc tttaacaacc acgtgcgtac  11100
gcttgtggcg cgcgaggagg tggctatagg actgatgcat ctgtgggact ttgtaagcgc  11160
gctggagcaa aacccaaata gcaagccgct catggcgcag ctgttcctta tagtgcagca  11220
cagcagggac aacgaggcat tcagggatgc gctgctaaac atagtagagc ccgagggccg  11280
ctggctgctc gatttgataa acatcctgca gagcatagtg gtgcaggagc gcagcttgag  11340
cctggctgac aaggtggccg ccatcaacta ttccatgctt agcctgggca agttttacgc  11400
ccgcaagata taccataccc cttacgttcc catagacaag gaggtaaaga tcgaggggtt  11460
ctacatgcgc atggcgctga aggtgcttac cttgagcgac gacctgggcg tttatcgcaa  11520
cgagcgcatc cacaaggccg tgagcgtgag ccggcggcgc gagctcagcg accgcgagct  11580
gatgcacagc ctgcaaaggg ccctggctgg cacgggcagc ggcgatagag aggccgagtc  11640
ctactttgac gcgggcgctg acctgcgctg ggccccaagc cgacgcgccc tggaggcagc  11700
tggggccgga cctgggctgg cggtggcacc cgcgcgcgct ggcaacgtcg gcggcgtgga  11760
ggaatatgac gaggacgatg agtacgagcc agaggacggc gagtactaag cggtgatgtt  11820
tctgatcaga tgatgcaaga cgcaacggac ccggcggtgc gggcggcgct gcagagccag  11880
ccgtccggcc ttaactccac ggacgactgg cgccaggtca tggaccgcat catgtcgctg  11940
actgcgcgca atcctgacgc gttccggcag cagccgcagg ccaaccggct ctccgcaatt  12000
ctggaagcgg tggtcccggc gcgcgcaaac cccacgcacg agaaggtgct ggcgatcgta  12060
aacgcgctgg ccgaaaacag ggccatccgg cccgacgagg ccggcctggt ctacgacgcg  12120
```

```
ctgcttcagc gcgtggctcg ttacaacagc ggcaacgtgc agaccaacct ggaccggctg  12180
gtgggggatg tgcgcgaggc cgtggcgcag cgtgagcgcg cgcagcagca gggcaacctg  12240
ggctccatgg ttgcactaaa cgccttcctg agtacacagc ccgccaacgt gccgcgggga  12300
caggaggact acaccaactt tgtgagcgca ctgcggctaa tggtgactga gacaccgcaa  12360
agtgaggtgt accagtctgg gccagactat tttttccaga ccagtagaca aggcctgcag  12420
accgtaaacc tgagccaggc tttcaaaaac ttgcaggggc tgtggggggt gcgggctccc  12480
acaggcgacc gcgcgaccgt gtctagcttg ctgacgccca actcgcgcct gttgctgctg  12540
ctaatagcgc ccttcacgga cagtggcagc gtgtcccggg acacatacct aggtcacttg  12600
ctgacactgt accgcgaggc cataggtcag gcgcatgtgg acgagcatac tttccaggag  12660
attacaagtg tcagccgcgc gctggggcag gaggacacgg gcagcctgga ggcaacccta  12720
aactacctgc tgaccaaccg gcggcagaag atcccctcgt tgcacagttt aaacagcgag  12780
gaggagcgca ttttgcgcta cgtgcagcag agcgtgagcc ttaacctgat gcgcgacggg  12840
gtaacgccca gcgtggcgct ggacatgacc gcgcgcaaca tggaaccggg catgtatgcc  12900
tcaaaccggc cgtttatcaa ccgcctaatg gactacttgc atcgcgcggc cgccgtgaac  12960
cccgagtatt tcaccaatgc catcttgaac ccgcactggc taccgccccc tggtttctac  13020
accgggggat tcgaggtgcc cgagggtaac gatggattcc tctgggacga catagacgac  13080
agcgtgtttt ccccgcaacc gcagaccctg ctagagttgc aacagcgcga gcaggcagag  13140
gcggcgctgc gaaaggaaag cttccgcagg ccaagcagct tgtccgatct aggcgctgcg  13200
gccccgcggt cagatgctag tagcccattt ccaagcttga tagggtctct taccagcact  13260
cgcaccaccc gcccgcgcct gctgggcgag gaggagtacc taaacaactc gctgctgcag  13320
ccgcagcgcg aaaaaaacct gcctccggca tttcccaaca acgggataga gagcctagtg  13380
gacaagatga gtagatggaa gacgtacgcg caggagcaca gggacgtgcc aggcccgcgc  13440
ccgcccaccc gtcgtcaaag gcacgaccgt cagcggggtc tggtgtggga ggacgatgac  13500
tcggcagacg acagcagcgt cctggatttg ggagggagtg gcaacccgtt tgcgcacctt  13560
cgccccaggc tggggagaat gttttaaaaa aaaaaaagca tgatgcaaaa taaaaaactc  13620
accaaggcca tggcaccgag cgttggtttt cttgtattcc ccttagtatg cggcgcgcgg  13680
cgatgtatga ggaaggtcct cctccctcct acgagagtgt ggtgagcgcg gcgccagtgg  13740
cggcggcgct gggttctccc ttcgatgctc ccctggaccc gccgtttgtg cctccgcggt  13800
acctgcggcc taccgggggg agaaacagca tccgttactc tgagttggca cccctattcg  13860
acaccacccg tgtgtacctg gtggacaaca agtcaacgga tgtggcatcc ctgaactacc  13920
agaacgacca cagcaacttt ctgaccacgg tcattcaaaa caatgactac agcccggggg  13980
aggcaagcac acagaccatc aatcttgacg accggtcgca ctggggcggc gacctgaaaa  14040
ccatcctgca taccaacatg ccaaatgtga acgagttcat gtttaccaat aagtttaagg  14100
cgcgggtgat ggtgtcgcgc ttgcctacta aggacaatca ggtggagctg aaatacgagt  14160
gggtggagtt cacgctgccc gagggcaact actccgagac catgaccata gaccttatga  14220
acaacgcgat cgtggagcac tacttgaaag tgggcagaca gaacggggtt ctggaaagcg  14280
acatcggggt aaagtttgac acccgcaact tcagactggg gtttgacccc gtcactggtc  14340
ttgtcatgcc tggggtatat acaaacgaag ccttccatcc agacatcatt ttgctgccag  14400
gatgcggggt ggacttcacc cacagccgcc tgagcaactt gttgggcatc cgcaagcggc  14460
```

```
aacccttcca ggagggcttt aggatcacct acgatgatct ggagggtggt aacattcccg  14520
cactgttgga tgtggacgcc taccaggcga gcttgaaaga tgacaccgaa cagggcgggg  14580
gtggcgcagg cggcagcaac agcagtggca gcggcgcgga agagaactcc aacgcggcag  14640
ccgcggcaat gcagccggtg gaggacatga acgatcatgc cattcgcggc gacacctttg  14700
ccacacgggc tgaggagaag cgcgctgagg ccgaagcagc ggccgaagct gccgcccccg  14760
ctgcgcaacc cgaggtcgag aagcctcaga agaaaccggt gatcaaaccc ctgacagagg  14820
acagcaagaa acgcagttac aacctaataa gcaatgacag caccttcacc cagtaccgca  14880
gctggtacct tgcatacaac tacggcgacc ctcagaccgg aatccgctca tggaccctgc  14940
tttgcactcc tgacgtaacc tgcggctcgg agcaggtcta ctggtcgttg ccagacatga  15000
tgcaagaccc cgtgaccttc cgctccacgc gccagatcag caactttccg gtggtgggcg  15060
ccgagctgtt gcccgtgcac tccaagagct tctacaacga ccaggccgtc tactcccaac  15120
tcatccgcca gtttacctct ctgacccacg tgttcaatcg ctttcccgag aaccagattt  15180
tggcgcgccc gccagccccc accatcacca ccgtcagtga aaacgttcct gctctcacag  15240
atcacgggac gctaccgctg cgcaacagca tcggaggagt ccagcgagtg accattactg  15300
acgccagacg ccgcacctgc ccctacgttt acaaggccct gggcatagtc tcgccgcgcg  15360
tcctatcgag ccgcactttt tgagcaagca tgtccatcct tatatcgccc agcaataaca  15420
caggctgggg cctgcgcttc ccaagcaaga tgtttggcgg ggccaagaag cgctccgacc  15480
aacacccagt gcgcgtgcgc gggcactacc gcgcgccctg gggcgcgcac aaacgcggcc  15540
gcactgggcg caccaccgtc gatgacgcca tcgacgcggt ggtggaggag gcgcgcaact  15600
acacgcccac gccgccacca gtgtccacag tggacgcggc cattcagacc gtggtgcgcg  15660
gagcccggcg ctatgctaaa atgaagagac ggcggaggcg cgtagcacgt cgccaccgcc  15720
gccgacccgg cactgccgcc caacgcgcgg cggcggccct gcttaaccgc gcacgtcgca  15780
ccggccgacg ggcggccatg cgggccgctc gaaggctggc cgcgggtatt gtcactgtgc  15840
cccccaggtc caggcgacga gcggccgccg cagcagccgc ggccattagt gctatgactc  15900
agggtcgcag gggcaacgtg tattgggtgc gcgactcggt tagcggcctg cgcgtgcccg  15960
tgcgcacccg ccccccgcgc aactagattg caagaaaaaa ctacttagac tcgtactgtt  16020
gtatgtatcc agcggcggcg gcgcgcaacg aagctatgtc caagcgcaaa atcaaagaag  16080
agatgctcca ggtcatcgcg ccggagatct atggcccccc gaagaaggaa gagcaggatt  16140
acaagccccg aaagctaaag cggtcaaaa agaaaaagaa agatgatgat gatgaacttg  16200
acgacgaggt ggaactgctg cacgctaccg cgcccaggcg acgggtacag tggaaaggtc  16260
gacgcgtaaa acgtgttttg cgacccggca ccaccgtagt ctttacgccc ggtgagcgct  16320
ccacccgcac ctacaagcgc gtgtatgatg aggtgtacgg cgacgaggac ctgcttgagc  16380
aggccaacga gcgcctcggg gagtttgcct acggaaagcg gcataaggac atgctggcgt  16440
tgccgctgga cgagggcaac ccaacaccta gcctaaagcc cgtaacactg cagcaggtgc  16500
tgcccgcgct tgcaccgtcc gaagaaaagc gcggcctaaa gcgcgagtct ggtgacttgg  16560
cacccaccgt gcagctgatg gtacccaagc gccagcgact ggaagatgtc ttggaaaaaa  16620
tgaccgtgga acctgggctg gagcccgagg tccgcgtgcg gccaatcaag caggtggcgc  16680
cgggactggg cgtgcagacc gtggacgttc agatacccac taccagtagc accagtattg  16740
ccaccgccac agagggcatg gagacacaaa cgtccccggt tgcctcagcg gtggcggatg  16800
ccgcggtgca ggcggtcgct gcggccgcgt ccaagacctc tacggaggtg caaacggacc  16860
```

cgtggatgtt tcgcgtttca gccccccggc gcccgcgcgg ttcgaggaag tacggcgccg 16920
ccagcgcgct actgcccgaa tatgccctac atccttccat tgcgcctacc cccggctatc 16980
gtggctacac ctaccgcccc agaagacgag caactacccg acgccgaacc accactggaa 17040
cccgccgccg ccgtcgccgt cgccagcccg tgctggcccc gatttccgtg cgcagggtgg 17100
ctcgcgaagg aggcaggacc ctggtgctgc caacagcgcg ctaccacccc agcatcgttt 17160
aaaagccggt ctttgtggtt cttgcagata tggccctcac ctgccgcctc cgtttcccgg 17220
tgccgggatt ccgaggaaga atgcaccgta ggaggggcat ggccggccac ggcctgacgg 17280
gcggcatgcg tcgtgcgcac caccggcggc ggcgcgcgtc gcaccgtcgc atgcgcggcg 17340
gtatcctgcc cctccttatt ccactgatcg ccgcggcgat tggcgccgtg cccggaattg 17400
catccgtggc cttgcaggcg cagagacact gattaaaaac aagttgcatg tggaaaaatc 17460
aaaataaaaa gtctggactc tcacgctcgc ttggtcctgt aactattttg tagaatggaa 17520
gacatcaact ttgcgtctct ggccccgcga cacggctcgc gcccgttcat gggaaactgg 17580
caagatatcg gcaccagcaa tatgagcggt ggcgccttca gctggggctc gctgtggagc 17640
ggcattaaaa atttcggttc caccgttaag aactatggca gcaaggcctg gaacagcagc 17700
acaggccaga tgctgaggga taagttgaaa gagcaaaatt tccaacaaaa ggtggtagat 17760
ggcctggcct ctggcattag cggggtggtg gacctggcca accaggcagt gcaaaataag 17820
attaacagta agcttgatcc ccgccctccc gtagaggagc ctccaccggc cgtggagaca 17880
gtgtctccag aggggcgtgg cgaaaagcgt ccgcgccccg acagggaaga aactctggtg 17940
acgcaaatag acgagcctcc ctcgtacgag gaggcactaa agcaaggcct gcccaccacc 18000
cgtcccatcg cgcccatggc taccggagtg ctgggccagc acacacccgt aacgctggac 18060
ctgcctcccc ccgccgacac ccagcagaaa cctgtgctgc caggcccgac cgccgttgtt 18120
gtaacccgtc ctagccgcgc gtccctgcgc cgcgccgcca gcggtccgcg atcgttgcgg 18180
cccgtagcca gtggcaactg gcaaagcaca ctgaacagca tcgtgggtct gggggtgcaa 18240
tccctgaagc gccgacgatg cttctgaata gctaacgtgt cgtatgtgtg tcatgtatgc 18300
gtccatgtcg ccgccagagg agctgctgag ccgccgcgcg cccgctttcc aagatggcta 18360
ccccttcgat gatgccgcag tggtcttaca tgcacatctc gggccaggac gcctcggagt 18420
acctgagccc cgggctggtg cagtttgccc gcgccaccga gacgtacttc agcctgaata 18480
acaagtttag aaaccccacg gtggcgccta cgcacgacgt gaccacagac cggtcccagc 18540
gtttgacgct gcggttcatc cctgtggacc gtgaggatac tgcgtactcg tacaaggcgc 18600
ggttcaccct agctgtgggt gataaccgtg tgctggacat ggcttccacg tactttgaca 18660
tccgcggcgt gctggacagg ggccctactt ttaagcccta ctctggcact gcctacaacg 18720
ccctggctcc caagggtgcc ccaaatcctt gcgaatggga tgaagctgct actgctcttg 18780
aaataaacct agaagaagag gacgatgaca acgaagacga agtagacgag caagctgagc 18840
agcaaaaaac tcacgtattt gggcaggcgc cttattctgg tataaatatt acaaaggagg 18900
gtattcaaat aggtgtcgaa ggtcaaacac ctaaatatgc cgataaaaca tttcaacctg 18960
aacctcaaat aggagaatct cagtggtacg aaactgaaat taatcatgca gctgggagag 19020
tccttaaaaa gactacccca atgaaaccat gttacggttc atatgcaaaa cccacaaatg 19080
aaaatggagg gcaaggcatt cttgtaaagc aacaaaatgg aaagctagaa agtcaagtgg 19140
aaatgcaatt tttctcaact actgaggcga ccgcaggcaa tggtgataac ttgactccta 19200
aagtggtatt gtacagtgaa gatgtagata tagaaacccc agacactcat atttcttaca 19260
tgcccactat taaggaaggt aactcacgag aactaatggg ccaacaatct atgcccaaca 19320
ggcctaatta cattgctttt agggacaatt ttattggtct aatgtattac aacagcacgg 19380
gtaatatggg tgttctggcg ggccaagcat cgcagttgaa tgctgttgta gatttgcaag 19440
acagaaacac agagctttca taccagcttt tgcttgattc cattggtgat agaaccaggt 19500
acttttctat gtggaatcag gctgttgaca gctatgatcc agatgttaga attattgaaa 19560
atcatggaac tgaagatgaa cttccaaatt actgctttcc actgggaggt gtgattaata 19620
cagagactct taccaaggta aaacctaaaa caggtcagga aaatggatgg gaaaaagatg 19680
ctacagaatt ttcagataaa aatgaaataa gagttggaaa taattttgcc atggaaatca 19740
atctaaatgc caacctgtgg agaaatttcc tgtactccaa catagcgctg tatttgcccg 19800
acaagctaaa gtacagtcct tccaacgtaa aaatttctga taacccaaac acctacgact 19860
acatgaacaa gcgagtggtg gctcccgggt tagtggactg ctacattaac cttggagcac 19920
gctggtccct tgactatatg gacaacgtca acccatttaa ccaccaccgc aatgctggcc 19980
tgcgctaccg ctcaatgttg ctgggcaatg gtcgctatgt gcccttccac atccaggtgc 20040
ctcagaagtt ctttgccatt aaaaacctcc ttctcctgcc gggctcatac acctacgagt 20100
ggaacttcag gaaggatgtt aacatggttc tgcagagctc cctaggaaat gacctaaggg 20160
ttgacggagc cagcattaag tttgatagca tttgccttta cgccaccttc ttccccatgg 20220
cccacaacac cgcctccacg cttgaggcca tgcttagaaa cgacaccaac gaccagtcct 20280
ttaacgacta tctctccgcc gccaacatgc tctaccctat acccgccaac gctaccaacg 20340
tgcccatatc catcccctcc cgcaactggg cggctttccg cggctgggcc ttcacgcgcc 20400
ttaagactaa ggaaacccca tcactgggct cgggctacga cccttattac acctactctg 20460
gctctatacc ctacctagat ggaacctttt acctcaacca cacctttaag aaggtggcca 20520
ttacctttga ctcttctgtc agctggcctg gcaatgaccg cctgcttacc cccaacgagt 20580
ttgaaattaa gcgctcagtt gacggggagg gttacaacgt tgcccagtgt aacatgacca 20640
aagactggtt cctggtacaa atgctagcta actacaacat tggctaccag ggcttctata 20700
tcccagagag ctacaaggac cgcatgtact ccttctttag aaacttccag cccatgagcc 20760
gtcaggtggt ggatgatact aaatacaagg actaccaaca ggtgggcatc ctacaccaac 20820
acaacaactc tggatttgtt ggctaccttg cccccaccat gcgcgaagga caggcctacc 20880
ctgctaactt cccctatccg cttataggca agaccgcagt tgacagcatt acccagaaaa 20940
agtttctttg cgatcgcacc ctttggcgca tcccattctc cagtaacttt atgtccatgg 21000
gcgcactcac agacctgggc caaaaccttc tctacgccaa ctccgcccac gcgctagaca 21060
tgacttttga ggtggatccc atggacgagc ccacccttct ttatgttttg tttgaagtct 21120
ttgacgtggt ccgtgtgcac cggccgcacc gcggcgtcat cgaaaccgtg tacctgcgca 21180
cgcccttctc ggccggcaac gccacaacat aaagaagcaa gcaacatcaa caacagctgc 21240
cgccatgggc tccagtgagc aggaactgaa agccattgtc aaagatcttg gttgtgggcc 21300
atattttttg ggcacctatg acaagcgctt tccaggcttt gtttctccac acaagctcgc 21360
ctgcgccata gtcaatacgg ccggtcgcga gactgggggc gtacactgga tggcctttgc 21420
ctggaacccg cactcaaaaa catgctacct ctttgagccc tttggctttt ctgaccagcg 21480
actcaagcag gtttaccagt ttgagtacga gtcactcctg cgccgtagcg ccattgcttc 21540
ttcccccgac cgctgtataa cgctggaaaa gtccacccaa agcgtacagg ggcccaactc 21600
ggccgcctgt ggactattct gctgcatgtt tctccacgcc tttgccaact ggccccaaac 21660
tcccatggat cacaacccca ccatgaacct tattaccggg gtacccaact ccatgctcaa 21720
cagtccccag gtacagccca ccctgcgtcg caaccaggaa cagctctaca gcttcctgga 21780
gcgccactcg ccctacttcc gcagccacag tgcgcagatt aggagcgcca cttctttttg 21840
tcacttgaaa aacatgtaaa aataatgtac tagagacact ttcaataaag gcaaatgctt 21900
ttatttgtac actctcgggt gattatttac cccccaccctt gccgtctgcg ccgtttaaaa 21960
atcaaagggg ttctgccgcg catcgctatg cgccactggc agggacacgt tgcgatactg 22020
gtgtttagtg ctccacttaa actcaggcac aaccatccgc ggcagctcgg tgaagttttc 22080
actccacagg ctgcgcacca tcaccaacgc gtttagcagg tcgggcgccg atatcttgaa 22140
gtcgcagttg gggcctccgc cctgcgcgcg cgagttgcga tacacagggt tgcagcactg 22200
gaacactatc agcgccgggt ggtgcacgct ggccagcacg ctcttgtcgg agatcagatc 22260
cgcgtccagg tcctccgcgt tgctcagggc gaacggagtc aactttggta gctgccttcc 22320
caaaaagggc gcgtgcccag gctttgagtt gcactcgcac cgtagtggca tcaaaaggtg 22380
accgtgcccg gtctgggcgt taggatacag cgcctgcata aaagccttga tctgcttaaa 22440
agccacctga gcctttgcgc cttcagagaa gaacatgccg caagacttgc cggaaaactg 22500
attggccgga caggccgcgt cgtgcacgca gcaccttgcg tcggtgttgg agatctgcac 22560
cacatttcgg ccccaccggt tcttcacgat cttggccttg ctagactgct ccttcagcgc 22620
gcgctgcccg ttttcgctcg tcacatccat ttcaatcacg tgctccttat ttatcataat 22680
gcttccgtgt agacacttaa gctcgccttc gatctcagcg cagcggtgca gccacaacgc 22740
gcagcccgtg ggctcgtgat gcttgtaggt cacctctgca aacgactgca ggtacgcctg 22800
caggaatcgc cccatcatcg tcacaaaggt cttgttgctg gtgaaggtca gctgcaaccc 22860
gcggtgctcc tcgttcagcc aggtcttgca tacggccgcc agagcttcca cttggtcagg 22920
cagtagtttg aagttcgcct ttagatcgtt atccacgtgg tacttgtcca tcagcgcgcg 22980
cgcagcctcc atgcccttct cccacgcaga cacgatcggc acactcagcg ggttcatcac 23040
cgtaatttca ctttccgctt cgctgggctc ttcctcttcc tcttgcgtcc gcataccacg 23100
cgccactggg tcgtcttcat tcagccgccg cactgtgcgc ttacctcctt tgccatgctt 23160
gattagcacc ggtgggttgc tgaaacccac catttgtagc gccacatctt ctctttcttc 23220
ctcgctgtcc acgattacct ctggtgatgg cgggcgctcg ggcttgggag aagggcgctt 23280
ctttttcttc ttgggcgcaa tggccaaatc cgccgccgag gtcgatggcc gcgggctggg 23340
tgtgcgcggc accagcgcgt cttgtgatga gtcttcctcg tcctcggact cgatacgccg 23400
cctcatccgc ttttttgggg gcgcccgggg aggcggcggc gacggggacg gggacgacac 23460
gtcctccatg gttgggggac gtcgcgccgc accgcgtccg cgctcggggg tggtttcgcg 23520
ctgctcctct tcccgactgg ccatttcctt ctcctatagg cagaaaaaga tcatggagtc 23580
agtcgagaag aaggacagcc taaccgcccc ctctgagttc gccaccaccg cctccaccga 23640
tgccgccaac gcgcctacca ccttccccgt cgaggcaccc ccgcttgagg aggaggaagt 23700
gattatcgag caggacccag gttttgtaag cgaagacgac gaggaccgct cagtaccaac 23760
agaggataaa aagcaagacc aggacaacgc agaggcaaac gaggaacaag tcgggcgggg 23820
ggacgaaagg catggcgact acctagatgt gggagacgac gtgctgttga agcatctgca 23880
gcgccagtgc gccattatct gcgacgcgtt gcaagagcgc agcgatgtgc cctcgccat 23940

```
agcggatgtc agccttgcct acgaacgcca cctattctca ccgcgcgtac cccccaaacg  24000
ccaagaaaac ggcacatgcg agcccaaccc gcgcctcaac ttctaccccg tatttgccgt  24060
gccagaggtg cttgccacct atcacatctt tttccaaaac tgcaagatac ccctatcctg  24120
ccgtgccaac cgcagccgag cggacaagca gctggccttg cggcagggcg ctgtcatacc  24180
tgatatcgcc tcgctcaacg aagtgccaaa aatctttgag ggtcttggac gcgacgagaa  24240
gcgcgcggca aacgctctgc aacaggaaaa cagcgaaaat gaaagtcact ctggagtgtt  24300
ggtggaactc gagggtgaca acgcgcgcct agccgtacta aaacgcagca tcgaggtcac  24360
ccactttgcc tacccggcac ttaacctacc ccccaaggtc atgagcacag tcatgagtga  24420
gctgatcgtg cgccgtgcgc agcccctgga gagggatgca aatttgcaag aacaaacaga  24480
ggagggccta cccgcagttg gcgacgagca gctagcgcgc tggcttcaaa cgcgcgagcc  24540
tgccgacttg gaggagcgac gcaaactaat gatggccgca gtgctcgtta ccgtggagct  24600
tgagtgcatg cagcggttct ttgctgaccc ggagatgcag cgcaagctag aggaaacatt  24660
gcactacacc tttcgacagg gctacgtacg ccaggcctgc aagatctcca acgtggagct  24720
ctgcaacctg gtctcctacc ttggaatttt gcacgaaaac cgccttgggc aaaacgtgct  24780
tcattccacg ctcaagggcg aggcgcgccg cgactacgtc cgcgactgcg tttacttatt  24840
tctatgctac acctggcaga cggccatggg cgtttggcag cagtgcttgg aggagtgcaa  24900
cctcaaggag ctgcagaaac tgctaaagca aaacttgaag gacctatgga cggccttcaa  24960
cgagcgctcc gtggccgcgc acctggcgga catcattttc cccgaacgcc tgcttaaaac  25020
cctgcaacag ggtctgccag acttcaccag tcaaagcatg ttgcagaact ttaggaactt  25080
tatcctagag cgctcaggaa tcttgcccgc cacctgctgt gcacttccta gcgactttgt  25140
gcccattaag taccgcgaat gccctccgcc gctttggggc cactgctacc ttctgcagct  25200
agccaactac cttgcctacc actctgacat aatggaagac gtgagcggtg acggtctact  25260
ggagtgtcac tgtcgctgca acctatgcac cccgcaccgc tccctggttt gcaattcgca  25320
gctgcttaac gaaagtcaaa ttatcggtac ctttgagctg cagggtccct cgcctgacga  25380
aaagtccgcg gctccggggt tgaaactcac tccggggctg tggacgtcgg cttaccttcg  25440
caaatttgta cctgaggact accacgccca cgagattagg ttctacgaag accaatcccg  25500
cccgccaaat gcggagctta ccgcctgcgt cattacccag ggccacattc ttggccaatt  25560
gcaagccatc aacaaagccc gccaagagtt tctgctacga aagggacggg ggtttactt  25620
ggacccccag tccggcgagg agctcaaccc aatccccccg ccgccgcagc cctatcagca  25680
gcagccgcgg gcccttgctt cccaggatgg cacccaaaaa gaagctgcag ctgccgccgc  25740
cacccacgga cgaggaggaa tactgggaca gtcaggcaga ggaggttttg gacgaggagg  25800
aggaggacat gatggaagac tgggagagcc tagacgagga agcttccgag gtcgaagagg  25860
tgtcagacga aacaccgtca ccctcggtcg cattcccctc gccggcgccc cagaaatcgg  25920
caaccggttc cagcatggct acaacctccg ctcctcaggc gccgccggca ctgcccgttc  25980
gccgacccaa ccgtagatgg gacaccactg gaaccagggc cggtaagtcc aagcagccgc  26040
cgccgttagc ccaagagcaa caacagcgcc aaggctaccg ctcatggcgc gggcacaaga  26100
acgccatagt tgcttgcttg caagactgtg ggggcaacat ctccttcgcc cgccgctttc  26160
ttctctacca tcacggcgtg gccttccccc gtaacatcct gcattactac cgtcatctct  26220
acagcccata ctgcaccggc ggcagcggca gcggcagcaa cagcagcggc cacacagaag  26280
caaaggcgac cggatagcaa gactctgaca aagcccaaga aatccacagc ggcggcagca  26340
```

gcaggaggag gagcgctgcg tctggcgccc aacgaacccg tatcgacccg cgagcttaga 26400
aacaggattt ttcccactct gtatgctata tttcaacaga gcaggggcca agaacaagag 26460
ctgaaaataa aaaacaggtc tctgcgatcc ctcacccgca gctgcctgta tcacaaaagc 26520
gaagatcagc ttcggcgcac gctggaagac gcggaggctc tcttcagtaa atactgcgcg 26580
ctgactctta aggactagtt tcgcgccctt tctcaaattt aagcgcgaaa actacgtcat 26640
ctccagcggc cacacccggc gccagcacct gtcgtcagcg ccattatgag caaggaaatt 26700
cccacgccct acatgtggag ttaccagcca caaatgggac ttgcggctgg agctgcccaa 26760
gactactcaa cccgaataaa ctacatgagc gcgggacccc acatgatatc ccgggtcaac 26820
ggaatccgcg cccaccgaaa ccgaattctc ttggaacagg cggctattac caccacacct 26880
cgtaataacc ttaatccccg tagttggccc gctgccctgg tgtaccagga aagtcccgct 26940
cccaccactg tggtacttcc cagagacgcc caggccgaag ttcagatgac taactcaggg 27000
gcgcagcttg cgggcggctt tcgtcacagg gtgcggtcgc ccgggcaggg tataactcac 27060
ctgacaatca gagggcgagg tattcagctc aacgacgagt cggtgagctc ctcgcttggt 27120
ctccgtccgg acgggacatt tcagatcggc ggcgccggcc gtccttcatt cacgcctcgt 27180
caggcaatcc taactctgca gacctcgtcc tctgagccgc gctctggagg cattggaact 27240
ctgcaattta ttgaggagtt tgtgccatcg gtctacttta accccttctc gggacctccc 27300
ggccactatc cggatcaatt tattcctaac tttgacgcgg taaaggactc ggcggacggc 27360
tacgactgaa tgttaagtgg agaggcagag caactgcgcc tgaaacacct ggtccactgt 27420
cgccgccaca agtgctttgc ccgcgactcc ggtgagtttt gctactttga attgcccgag 27480
gatcatatcg agggcccggc gcacggcgtc cggcttaccg cccagggaga gcttgcccgt 27540
agcctgattc gggagtttac ccagcgcccc ctgctagttg agcgggacag gggaccctgt 27600
gttctcactg tgatttgcaa ctgtcctaac cttggattac atcaagatct ttgttgccat 27660
ctctgtgctg agtataataa atacagaaat taaaatatac tggggctcct atcgccatcc 27720
tgtaaacgcc accgtcttca cccgcccaag caaaccaagg cgaaccttac ctggtacttt 27780
taacatctct ccctctgtga tttacaacag tttcaaccca gacggagtga gtctacgaga 27840
gaacctctcc gagctcagct actccatcag aaaaaacacc accctcctta cctgccggga 27900
acgtacgagt gcgtcaccgg ccgctgcacc acacctaccg cctgaccgta aaccagactt 27960
tttccggaca gacctcaata actctgttta ccagaacagg aggtgagctt agaaaaccct 28020
tagggtatta ggccaaaggc gcagctactg tggggtttat gaacaattca agcaactcta 28080
cgggctattc taattcaggt ttctctagaa atggacggaa ttattacaga gcagcgcctg 28140
ctagaaagac gcagggcagc ggccgagcaa cagcgcatga atcaagagct ccaagacatg 28200
gttaacttgc accagtgcaa aaggggtatc ttttgtctgg taaagcaggc caaagtcacc 28260
tacgacagta ataccaccgg acaccgcctt agctacaagt tgccaaccaa gcgtcagaaa 28320
ttggtggtca tggtgggaga aaagcccatt accataactc agcactcggt agaaaccgaa 28380
ggctgcattc actcaccttg tcaaggacct gaggatctct gcacccttat taagaccctg 28440
tgcggtctca aagatcttat tccctttaac taataaaaaa aaataataaa gcatcactta 28500
cttaaaatca gttagcaaat ttctgtccag tttattcagc agcacctcct tgccctcctc 28560
ccagctctgg tattgcagct tcctcctggc tgcaaacttt ctccacaatc taaatggaat 28620
gtcagtttcc tcctgttcct gtccatccgc acccactatc ttcatgaagc gcgcaagacc 28680
gtctgaagat accttcaacc ccgtgtatcc atatgacacg gaaaccggtc ctccaactgt 28740
gccttttctt actcctccct ttgtatcccc caatgggttt caagagagtc cccctggagt 28800
tcttacttta aaatgtttaa ccccactaac aaccacaggc ggatctctac agctaaaagt 28860
gggaggggga cttacagtgg atgacactga tggtacctta caagaaaaca tacgtgctac 28920
agcacccatt actaaaaata atcactctgt agaactatcc attggaaatg gattagaaac 28980
tcaaaacaat aaactatgtg ccaaattggg aaatgggtta aaatttaaca acggtgacat 29040
ttgtataaag gatagtatta acaccttatg gactggaata aaccctccac ctaactgtca 29100
aattgtggaa aacactaata caaatgatgg caaacttact ttagtattag taaaaaacgg 29160
agggcttgtt aatggctacg tgtctctagt tggtgtatca gacactgtga accaaatgtt 29220
cacacaaaag acagcaaaca tccaattaag attatatttt gactcttctg gaaatctatt 29280
aactgatgaa tcagacttaa aaattccact taaaaataaa tcttctacag cgaccagtga 29340
aactgtagcc agcagcaaag cctttatgcc aagtactaca gcttatccct tcaacaccac 29400
tactagggat agtgaaaact acattcatgg aatatgttac tacatgacta gttatgatag 29460
aagtctattt ccccttgaaca tttctataat gctaaacagc cgtatgattt cttccaatgt 29520
tgcctatgcc atacaatttg aatggaatct aaatgcaagt gaatctccag aaagcaacat 29580
agctacgctg accacatccc cctttttctt ttcttacatt acagaagacg acaactaaaa 29640
tgcccaagaa taaagaatcg tttgtgttat gtttcaacgt gtttattttt caattgcaga 29700
aaatttcaag tcatttttca ttcagtagta tagccccacc accacatagc ttatacagat 29760
caccgtacct taatcaaact cacagaaccc tagtattcaa cctgccacct ccctcccaac 29820
acacagagta cacagtcctt tctccccggc tggccttaaa aagcatcata tcatgggtaa 29880
cagacatatt cttaggtgtt atattccaca cggtttcctg tcgagccaaa cgctcatcag 29940
tgatattaat aaactccccg ggcagctcac ttaagttcat gtcgctgtcc agctgctgag 30000
ccacaggctg ctgtccaact tgcggttgct taacgggcgg cgaaggagaa gtccacgcct 30060
acatgggggt agagtcataa tcgtgcatca ggatagggcg gtggtgctgc agcagcgcgc 30120
gaataaactg ctgccgccgc cgctccgtcc tgcaggaata caacatggca gtggtctcct 30180
cagcgatgat tcgcaccgcc cgcagcataa ggcgccttgt cctccgggca cagcagcgca 30240
ccctgatctc acttaaatca gcacagtaac tgcagcacag caccacaata ttgttcaaaa 30300
tcccacagtg caaggcgctg tatccaaagc tcatggcggg gaccacagaa ccccacgtggc 30360
catcatacca caagcgcagg tagattaagt ggcgacccct cataaacacg ctggacataa 30420
acattacctc ttttggcatg ttgtaattca ccacctcccg gtaccatata aacctctgat 30480
taaacatggc gccatccacc accatcctaa accagctggc caaaacctgc ccgccggcta 30540
tacactgcag ggaaccggga ctggaacaat gacagtggag agcccaggac tcgtaaccat 30600
ggatcatcat gctcgtcatg atatcaatgt tggcacaaca caggcacacg tgcatacact 30660
tcctcaggat tacaagctcc tcccgcgtta gaaccatatc ccagggaaca acccattcct 30720
gaatcagcgt aaatcccaca ctgcagggaa gacctcgcac gtaactcacg ttgtgcattg 30780
tcaaagtgtt acattcgggc agcagcggat gatcctccag tatggtagcg cgggtttctg 30840
tctcaaaagg aggtagacga tccctactgt acggagtgcg ccgagacaac cgagatcgtg 30900
ttggtcgtag tgtcatgcca aatggaacgc cggacgtagt catatttcct gaagcaaaac 30960
caggtgcggg cgtgacaaac agatctgcgt ctccggtctc gccgcttaga tcgctctgtg 31020
tagtagttgt agtatatcca ctctctcaaa gcatccaggc gccccctggc ttcgggttct 31080
atgtaaactc cttcatgcgc cgctgccctg ataacatcca ccaccgcaga ataagccaca 31140
cccagccaac ctacacattc gttctgcgag tcacacacgg gaggagcggg aagagctgga 31200
agaaccatgt tttttttttt attccaaaag attatccaaa acctcaaaat gaagatctat 31260
taagtgaacg cgctcccctc cggtggcgtg gtcaaactct acagccaaag aacagataat 31320
ggcatttgta agatgttgca caatggcttc caaaaggcaa acggccctca cgtccaagtg 31380
gacgtaaagg ctaaaccctt cagggtgaat ctcctctata aacattccag caccttcaac 31440
catgcccaaa taattctcat ctcgccacct tctcaatata tctctaagca aatcccgaat 31500
attaagtccg gccattgtaa aaatctgctc cagagcgccc tccaccttca gcctcaagca 31560
gcgaatcatg attgcaaaaa ttcaggttcc tcacagacct gtataagatt caaaagcgga 31620
acattaacaa aaataccgcg atcccgtagg tcccttcgca gggccagctg aacataatcg 31680
tgcaggtctg cacggaccag cgcggccact tccccgccag gaaccttgac aaaagaaccc 31740
acactgatta tgacacgcat actcggagct atgctaacca gcgtagcccc gatgtaagct 31800
ttgttgcatg ggcggcgata taaaatgcaa ggtgctgctc aaaaaatcag gcaaagcctc 31860
gcgcaaaaaa gaaagcacat cgtagtcatg ctcatgcaga taaaggcagg taagctccgg 31920
aaccaccaca gaaaaagaca ccatttttct ctcaaacatg tctgcgggtt tctgcataaa 31980
cacaaaataa aataacaaaa aaacatttaa acattagaag cctgtcttac aacaggaaaa 32040
acaaccctta taagcataag acggactacg gccatgccgg cgtgaccgta aaaaaactgg 32100
tcaccgtgat taaaaagcac caccgacagc tcctcggtca tgtccggagt cataatgtaa 32160
gactcggtaa acacatcagg ttgattcatc ggtcagtgct aaaaagcgac cgaaatagcc 32220
cgggggaata catacccgca ggcgtagaga caacattaca gcccccatag gaggtataac 32280
aaaattaata ggagagaaaa acacataaac acctgaaaaa ccctcctgcc taggcaaaat 32340
agcaccctcc cgctccagaa caacatacag cgcttcacag cggcagccta acagtcagcc 32400
ttaccagtaa aaaagaaaac ctattaaaaa aacaccactc gacacggcac cagctcaatc 32460
agtcacagtg taaaaaaggg ccaagtgcag agcgagtata tataggacta aaaaatgacg 32520
taacggttaa agtccacaaa aaacacccag aaaaccgcac gcgaacctac gcccagaaac 32580
gaaagccaaa aaacccacaa cttcctcaaa tcgtcacttc cgttttccca cgttacgtaa 32640
cttcccattt taagaaaact acaattccca acacatacaa gttactccgc cctaaaacct 32700
acgtcacccg ccccgttccc acgccccgcg ccacgtcaca aactccaccc cctcattatc 32760
atattggctt caatccaaaa taaggtatat tattgatgat gttaat 32806

<210> SEQ ID NO 12
<211> LENGTH: 15
<212> TYPE: PRT
<213> ORGANISM: Plasmodium vivax

<400> SEQUENCE: 12

Asp Tyr Asp Val Val Tyr Leu Lys Pro Leu Ala Gly Met Tyr Lys
1 5 10 15

<210> SEQ ID NO 13
<211> LENGTH: 21
<212> TYPE: PRT
<213> ORGANISM: Plasmodium falciparum

<400> SEQUENCE: 13

Asp Ile Glu Lys Lys Ile Ala Lys Met Glu Lys Ala Ser Ser Val Phe 1 5 10 15

Asn Val Val Asn Ser
20

<210> SEQ ID NO 14
<211> LENGTH: 20
<212> TYPE: PRT
<213> ORGANISM: Plasmodium falciparum

<400> SEQUENCE: 14

Ile Glu Lys Lys Ile Ala Lys Met Glu Lys Ala Ser Ser Val Phe Asn
1 5 10 15

Val Val Asn Ser
20

<210> SEQ ID NO 15
<211> LENGTH: 19
<212> TYPE: PRT
<213> ORGANISM: Plasmodium falciparum

<400> SEQUENCE: 15

Glu Lys Lys Ile Ala Lys Met Glu Lys Ala Ser Ser Val Phe Asn Val
1 5 10 15

Val Asn Ser

<210> SEQ ID NO 16
<211> LENGTH: 20
<212> TYPE: PRT
<213> ORGANISM: Plasmodium falciparum

<400> SEQUENCE: 16

Asp Ile Glu Lys Lys Ile Ala Lys Met Glu Lys Ala Ser Ser Val Phe
1 5 10 15

Asn Val Val Asn
20

<210> SEQ ID NO 17
<211> LENGTH: 19
<212> TYPE: PRT
<213> ORGANISM: Plasmodium falciparum

<400> SEQUENCE: 17

Asp Ile Glu Lys Lys Ile Ala Lys Met Glu Lys Ala Ser Ser Val Phe
1 5 10 15

Asn Val Val

<210> SEQ ID NO 18
<211> LENGTH: 18
<212> TYPE: PRT
<213> ORGANISM: Plasmodium falciparum

<400> SEQUENCE: 18

Asp Ile Glu Lys Lys Ile Ala Lys Met Glu Lys Ala Ser Ser Val Phe
1 5 10 15

Asn Val

<210> SEQ ID NO 19
<211> LENGTH: 15
<212> TYPE: PRT
<213> ORGANISM: Clostridium tetani

<400> SEQUENCE: 19

Gln Tyr Ile Lys Ala Asn Ser Lys Phe Ile Gly Ile Thr Glu Leu
1 5 10 15

<210> SEQ ID NO 20
<211> LENGTH: 21
<212> TYPE: PRT
<213> ORGANISM: Clostridium tetani

<400> SEQUENCE: 20

Phe Asn Asn Phe Thr Val Ser Phe Trp Leu Arg Val Pro Lys Val Ser
1 5 10 15

Ala Ser His Leu Glu
20

<210> SEQ ID NO 21
<211> LENGTH: 14
<212> TYPE: PRT
<213> ORGANISM: Clostridium tetani

<400> SEQUENCE: 21

Thr Lys Ile Tyr Ser Tyr Phe Pro Ser Val Ile Ser Lys Val
1 5 10

<210> SEQ ID NO 22
<211> LENGTH: 15
<212> TYPE: PRT
<213> ORGANISM: Clostridium tetani

<400> SEQUENCE: 22

Val Arg Asp Ile Ile Asp Asp Phe Thr Asn Glu Ser Ser Gln Lys
1 5 10 15

<210> SEQ ID NO 23
<211> LENGTH: 14
<212> TYPE: PRT
<213> ORGANISM: Clostridium tetani

<400> SEQUENCE: 23

Val Ser Thr Ile Val Pro Tyr Ile Gly Pro Ala Leu Asn Ile
1 5 10

<210> SEQ ID NO 24
<211> LENGTH: 14
<212> TYPE: PRT
<213> ORGANISM: Clostridium tetani

<400> SEQUENCE: 24

Gln Tyr Ile Lys Ala Asn Ser Lys Phe Ile Gly Ile Thr Glu
1 5 10

<210> SEQ ID NO 25
<211> LENGTH: 21
<212> TYPE: PRT
<213> ORGANISM: Clostridium tetani

<400> SEQUENCE: 25

Phe Asn Asn Phe Thr Val Ser Phe Trp Leu Arg Val Pro Lys Val Ser
1 5 10 15

Ala Ser His Leu Glu
20

<210> SEQ ID NO 26
<211> LENGTH: 13

<212> TYPE: PRT
<213> ORGANISM: Influenza A virus

<400> SEQUENCE: 26

```
Pro Lys Tyr Val Lys Gln Asn Thr Leu Lys Leu Ala Thr
1               5                   10
```

<210> SEQ ID NO 27
<211> LENGTH: 15
<212> TYPE: PRT
<213> ORGANISM: Enterovirus 71

<400> SEQUENCE: 27

```
Ile Glu Thr Arg Cys Val Leu Asn Ser His Ser Thr Ala Glu Thr
1               5                   10                  15
```

<210> SEQ ID NO 28
<211> LENGTH: 15
<212> TYPE: PRT
<213> ORGANISM: Enterovirus 71

<400> SEQUENCE: 28

```
Glu Val Val Pro Gln Leu Leu Gln Tyr Met Phe Val Pro Pro Gly
1               5                   10                  15
```

<210> SEQ ID NO 29
<211> LENGTH: 15
<212> TYPE: PRT
<213> ORGANISM: Enterovirus 71

<400> SEQUENCE: 29

```
Leu Val Val Arg Ile Tyr Met Arg Met Lys His Val Arg Ala Trp
1               5                   10                  15
```

<210> SEQ ID NO 30
<211> LENGTH: 17
<212> TYPE: PRT
<213> ORGANISM: Epstein-Barr virus

<400> SEQUENCE: 30

```
Tyr Leu Gln Gln Asn Trp Trp Thr Leu Leu Val Asp Leu Leu Trp Leu
1               5                   10                  15

Leu
```

<210> SEQ ID NO 31
<211> LENGTH: 20
<212> TYPE: PRT
<213> ORGANISM: Human immunodeficiency virus

<400> SEQUENCE: 31

```
Asn Tyr Pro Ile Val Gln Asn Ile Gln Gly Gln Met Val His Gln Ala
1               5                   10                  15

Ile Ser Pro Arg
            20
```

<210> SEQ ID NO 32
<211> LENGTH: 20
<212> TYPE: PRT
<213> ORGANISM: Human immunodeficiency virus

<400> SEQUENCE: 32

```
Glu Trp Asp Arg Val His Pro Val His Ala Gly Pro Ile Ala Pro Gly
1               5                   10                  15
```

```
Gln Met Arg Glu
            20


<210> SEQ ID NO 33
<211> LENGTH: 20
<212> TYPE: PRT
<213> ORGANISM: Human immunodeficiency virus

<400> SEQUENCE: 33

Ser Thr Leu Gln Glu Gln Ile Gly Trp Met Thr Asn Asn Pro Pro Ile
1               5                   10                  15

Pro Val Gly Glu
            20


<210> SEQ ID NO 34
<211> LENGTH: 15
<212> TYPE: PRT
<213> ORGANISM: Human immunodeficiency virus

<400> SEQUENCE: 34

Lys Arg Trp Ile Ile Leu Gly Leu Asn Lys Ile Val Arg Met Tyr
1               5                   10                  15


<210> SEQ ID NO 35
<211> LENGTH: 20
<212> TYPE: PRT
<213> ORGANISM: Human immunodeficiency virus

<400> SEQUENCE: 35

Asn Lys Ile Val Arg Met Tyr Ser Pro Thr Ser Ile Leu Asp Ile Arg
1               5                   10                  15

Gln Gly Pro Lys
            20


<210> SEQ ID NO 36
<211> LENGTH: 20
<212> TYPE: PRT
<213> ORGANISM: Human immunodeficiency virus

<400> SEQUENCE: 36

Glu Pro Phe Arg Asp Tyr Val Asp Arg Phe Tyr Lys Thr Leu Arg Ala
1               5                   10                  15

Glu Gln Ala Ser
            20


<210> SEQ ID NO 37
<211> LENGTH: 20
<212> TYPE: PRT
<213> ORGANISM: Human immunodeficiency virus

<400> SEQUENCE: 37

Tyr Lys Thr Leu Arg Ala Glu Gln Ala Ser Gln Glu Val Lys Asn Trp
1               5                   10                  15

Met Thr Glu Thr
            20


<210> SEQ ID NO 38
<211> LENGTH: 20
<212> TYPE: PRT
<213> ORGANISM: Human immunodeficiency virus

<400> SEQUENCE: 38

Leu Leu Val Gln Asn Ala Asn Pro Asp Cys Lys Thr Ile Leu Lys Ala
```

```
1               5                   10                  15

Leu Gly Pro Ala
            20


<210> SEQ ID NO 39
<211> LENGTH: 20
<212> TYPE: PRT
<213> ORGANISM: Human immunodeficiency virus

<400> SEQUENCE: 39

Lys Thr Ile Leu Lys Ala Leu Gly Pro Ala Ala Thr Leu Glu Glu Met
1               5                   10                  15

Met Thr Ala Cys
            20


<210> SEQ ID NO 40
<211> LENGTH: 25
<212> TYPE: PRT
<213> ORGANISM: Human adenovirus type 5

<400> SEQUENCE: 40

Val Pro Phe His Ile Gln Val Pro Gln Lys Phe Phe Ala Ile Lys Asn
1               5                   10                  15

Leu Leu Leu Leu Pro Gly Ser Tyr Thr
            20                  25


<210> SEQ ID NO 41
<211> LENGTH: 25
<212> TYPE: PRT
<213> ORGANISM: Human adenovirus type 5

<400> SEQUENCE: 41

Val Thr Thr Asp Arg Ser Gln Arg Leu Thr Leu Arg Phe Ile Pro Val
1               5                   10                  15

Asp Arg Glu Asp Thr Ala Tyr Ser Tyr
            20                  25


<210> SEQ ID NO 42
<211> LENGTH: 20
<212> TYPE: PRT
<213> ORGANISM: Human adenovirus type 5

<400> SEQUENCE: 42

Gly Gln Gln Ser Met Pro Asn Arg Pro Asn Tyr Ile Ala Phe Arg Asp
1               5                   10                  15

Asn Phe Ile Gly
            20


<210> SEQ ID NO 43
<211> LENGTH: 28
<212> TYPE: PRT
<213> ORGANISM: Human adenovirus type 5

<400> SEQUENCE: 43

Glu Val Asp Pro Met Asp Glu Pro Thr Leu Leu Tyr Val Leu Phe Glu
1               5                   10                  15

Val Phe Asp Val Val Arg Val His Arg Pro His Arg
            20                  25
```